United States Patent
Di Pasqua et al.

(10) Patent No.: US 9,808,543 B2
(45) Date of Patent: Nov. 7, 2017

(54) IRON GARNET NANOPARTICLES FOR CANCER RADIOTHERAPY AND CHEMOTHERAPY

(71) Applicants: UNIVERSITY OF NORTH TEXAS HEALTH SCIENCE CENTER AT FORT WORTH, Fort Worth, TX (US); THE BOARD OF REGENTS OF THE UNIVERSITY OF TEXAS SYSTEM, Austin, TX (US)

(72) Inventors: Anthony J. Di Pasqua, Fort Worth, TX (US); Kenneth J. Balkus, Jr., The Colony, TX (US); Imalka S. Munaweera, Richardson, TX (US); Yi Shi, Fort Worth, TX (US)

(73) Assignees: UNIVERSITY OF NORTH TEXAS HEALTH SCIENCE CENTER AT FORT WORTH, Fort Worth, TX (US); THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 14/600,738

(22) Filed: Jan. 20, 2015

(65) Prior Publication Data
US 2015/0202337 A1 Jul. 23, 2015

Related U.S. Application Data

(60) Provisional application No. 61/929,394, filed on Jan. 20, 2014.

(51) Int. Cl.
| | | |
|---|---|---|
| *A61K 51/12* | (2006.01) |
| *A61K 33/24* | (2006.01) |
| *A61K 31/555* | (2006.01) |
| *A61K 45/06* | (2006.01) |
| *A61K 33/00* | (2006.01) |
| *A61K 33/22* | (2006.01) |
| *A61K 33/26* | (2006.01) |
| *A61K 33/38* | (2006.01) |
| *A61K 38/18* | (2006.01) |
| *A61K 38/19* | (2006.01) |
| *A61K 38/27* | (2006.01) |
| *A61K 38/30* | (2006.01) |
| *A61N 5/10* | (2006.01) |

(52) U.S. Cl.
CPC ........ *A61K 51/1244* (2013.01); *A61K 31/555* (2013.01); *A61K 33/00* (2013.01); *A61K 33/22* (2013.01); *A61K 33/24* (2013.01); *A61K 33/26* (2013.01); *A61K 33/38* (2013.01); *A61K 38/18* (2013.01); *A61K 38/193* (2013.01); *A61K 38/27* (2013.01); *A61K 38/30* (2013.01); *A61K 45/06* (2013.01); *A61K 51/1275* (2013.01); *A61N 5/1029* (2013.01); *A61N 5/1007* (2013.01); *A61N 2005/1021* (2013.01)

(58) Field of Classification Search
CPC ...... A61K 31/555; A61K 33/00; A61K 33/22; A61K 33/24; A61K 33/26; A61K 33/38; A61K 38/18; A61K 38/193; A61K 38/27; A61K 38/30; A61K 45/06; A61K 51/1244; A61K 51/1275; A61N 2005/1021; A61N 5/1007; A61N 5/1029
See application file for complete search history.

(56) References Cited

U.S. PATENT DOCUMENTS

| 3,535,245 A * | 10/1970 | Lindquist | ............... C04B 35/26 252/62.57 |
| 6,120,856 A * | 9/2000 | Liberti | ............... A61K 9/5094 252/62.56 |
| 2011/0200704 A1* | 8/2011 | Rombaut | ............. A01K 61/008 426/2 |

OTHER PUBLICATIONS

MacDonald et al., "The Use of Beta Rays in the Treatment of Chronic Eczema and Psoriasis", 1970, British Journal of Dermatology, vol. 82, pp. 283-286.*
Bult, W. et al. "Holmium Nanoparticles: Preparation and In Vitro Characterization of a New Device for Radioablation of Solid Malignancies" *Pharmaceutical Research*, 2010, vol. 27, pp. 2205-2212.
Cheng, X. et al. "Chemotherapy drug delivery from calcium phosphate nanoparticles" *International Journal of Nanomedicine*, 2007, vol. 2, No. 4, pp. 667-674.
Dash, S. et al. "Kinetic Modeling on Drug Release from Controlled Drug Delivery Systems" *Acta Poloniae Pharmaceutica—Drug Research*, 2010, vol. 67, No. 3, pp. 217-223.

(Continued)

*Primary Examiner* — Michael B Pallay
(74) *Attorney, Agent, or Firm* — Saliwanchik, Lloyd & Eisenschenk

(57) ABSTRACT

Iron garnet nanoparticles and or iron garnet particles containing various activatable nuclides, such as holmium-165 ($^{165}$Ho) and dysprosium-164 ($^{164}$Dy), are disclosed in this application. The iron garnet (e.g., HoIG and DyIG) nanoparticles and iron garnet particles can prepared using hydroxide co-precipitation methods. In some embodiments, radiosensitizers can be loaded on radioactive magnetic nanoparticles or radioactive iron garnet particles and, optionally, coated with suitable lipid bilayers. Methods of using the disclosed nanoparticles and particles for mediating therapeutic benefit in diseases responsive to radiation therapy are also provided. Another aspect of the invention provides films, electrospun fabrics or bandage coverings for the delivery of radiation to the site of a skin lesion amenable to treatment with radiation (e.g., skin cancers or psoriasis).

12 Claims, 39 Drawing Sheets
(16 of 39 Drawing Sheet(s) Filed in Color)

(56) References Cited

OTHER PUBLICATIONS

Di Pasqua, A.J. et al. "Tumor accumulation of neutron-activatable holmium-containing mesoporous silica nanoparticles in an orthotopic non-small cell lung cancer mouse model" *Inorganica Chimica Acta*, 2012, vol. 393, pp. 334-336.
Geldof, A.A. et al. "Radiosensitizing effect of cisplatin in prostate cancer cell lines" *Cancer Letters*, 1996, vol. 101, pp. 233-239.
Hassan, M.I. et al. "Bioactivity Assessment of Poly(ε-caprolactone)/Hydroxyapatite Electrospun Fibers for Bone Tissue Engineering Application" *Journal of Nanomaterials*, 2014, vol. 2014, pp. 1-6.
Lataifeh, M.S. "Magnetic Study of Al-Substituted Holmium Iron Garnet" *Journal of the Physical Society of Japan*, Jul. 2000, vol. 69, No. 7, pp. 2280-2282.
Munaweera, I. et al. "Electrospun Cellulose Acetate-Garnet Nanocomposite Magnetic Fibers for Bioseparations" *ACS Applied Materials & Interfaces*, 2014, vol. 6, pp. 244-251.
Munaweera, I. et al. "Chemoradiotherapeutic wrinkled mesoporous silica nanoparticles for use in cancer therapy," *APL Materials*, 2014, vol. 2, pp. 113315-1-113315-13.
Nguyet, D.T.T. et al. "Magnetization and coercivity of nanocrystalline gadolinium iron garnet" *Journal of Magnetism and Magnetic Materials*, 2013, vol. 332, pp. 180-185.
Nijsen, J.F.W. et al. "Holmium-166 poly lactic acid microspheres applicable for intra-arterial radionuclide therapy of hepatic malignancies: effects of preparation and neutron activation techniques" *European Journal of Nuclear Medicine*, 1999, vol. 26, pp. 699-704.
Rajendran, M. et al. "Size-dependent magnetic properties of nanocrystalline yttrium iron garnet powders" *Journal of Magnetism and Magnetic Materials*, 2006, vol. 301, pp. 212-219.
Rezaee, M. et al. "Cisplatin Enhances the Formation of DNA Single- and Double-Strand Breaks by Hydrated Electrons and Hydroxyl Radicals" *Radiation Research*, 2013, vol. 179, No. 3, pp. 323-331.
Sun, H.W. et al. "Magnetic Poly(PEGMA-MAA) Nanoparticles: Photochemical Preparation and Potential Application in Drug Delivery" *Journal of Biomaterials Science*, 2009, vol. 20, pp. 1675-1686.
Tyagi, P. et al. "Structural aspects of the anti-cancer drug oxaliplatin: A combined theoretical and experimental study" *Polyhedron*, 2008, vol. 27, pp. 3567-3574.
Wysokinski, R. et al. "Electronic structure, Raman and infrared spectra, and vibrational assignment of carboplatin. Density functional theory studies" *Journal of Molecular Structure:THEOCHEM*, 2006, vol. 758, pp. 169-179.
Yan, X. et al. "Cisplatin delivery from poly(acrylic acid-co-methyl methacrylate) microparticles" *Journal of Controlled Release*, 2005, vol. 106, pp. 198-208.

* cited by examiner

FIG. 16A
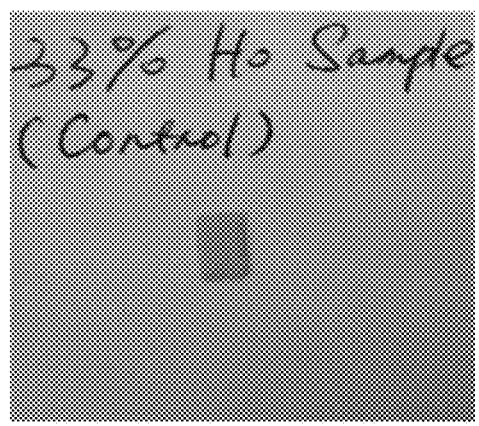
FIG. 16B
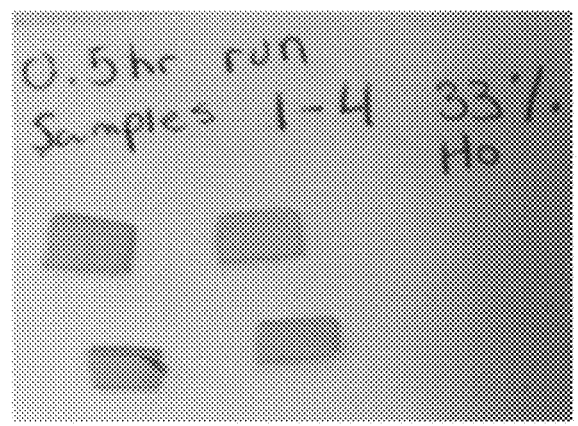
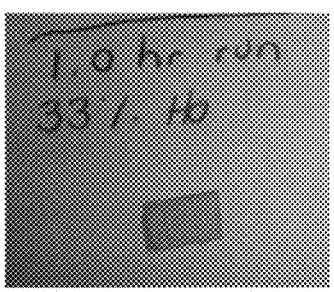
FIG. 16C
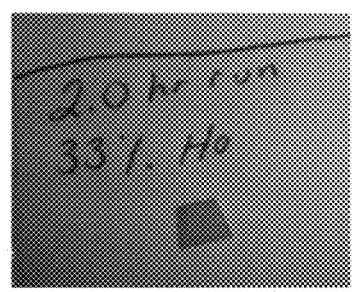
FIG. 16D
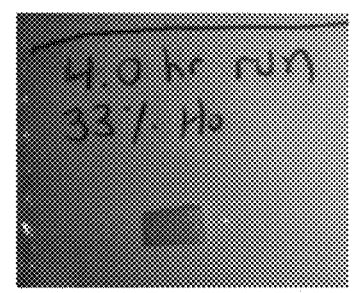
FIG. 16E
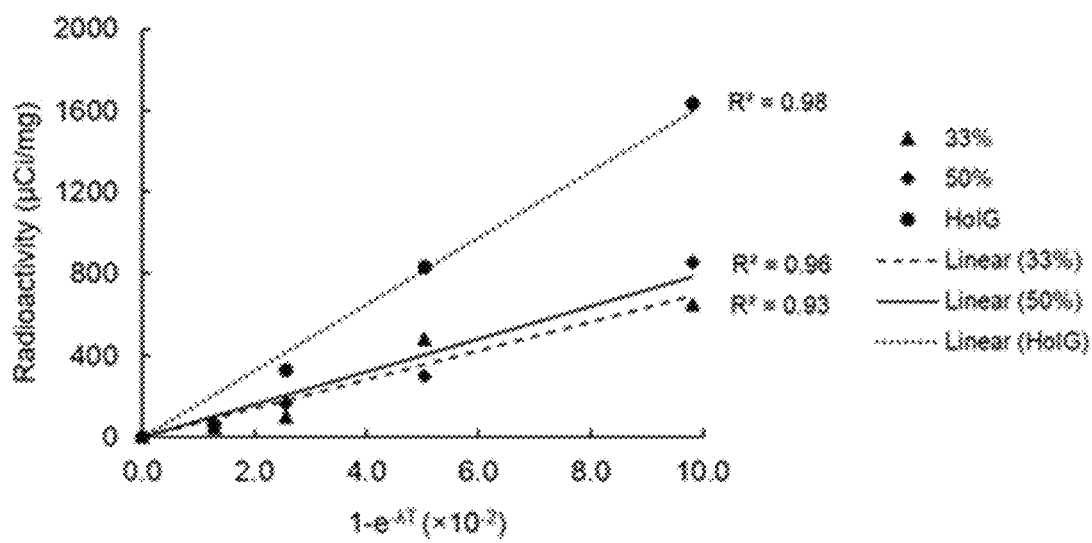
FIG. 16F

IRON GARNET NANOPARTICLES FOR CANCER RADIOTHERAPY AND CHEMOTHERAPY

CROSS-REFERENCE TO RELATED APPLICATION

This application claims the benefit of U.S. Provisional Application Ser. No. 61/929,394, filed Jan. 20, 2014, the disclosure of which is hereby incorporated by reference in its entirety, including all figures, tables and amino acid or nucleic acid sequences.

This invention was funded with monies awarded by the Texas Medical Research Collaborative (grant number RI6058).

BACKGROUND OF THE INVENTION

Although radionuclides have been used therapeutically for several decades, the main concern has been their accumulation in non-target healthy tissues. This problem can be controlled by magnetically targeted delivery of radionuclides' nanoparticle carriers with chemotherapeutic agents. Such chemotherapeutic agent-loaded radionuclide carriers can be injected to a patient and controlled by an external magnetic field for targeted drug delivery and selective radiotherapy. Also, incorporating hazardous radionuclides in these carriers can be challenging, so the process must be amenable to large amounts of radioactivity and radionuclides with short half-lives. Neutron activation of particulates with stable isotopes as a means of producing carriers of radioactive isotopes can overcome these limitations.

Particles for the treatment of cancer in combination with x-ray radiotherapy have been reported. For example a metal oxide such as titanium dioxide, zinc oxide, cerium oxide and mixtures of two or more were doped with rare earth elements. Radioactive holmium-166-loaded poly (L)-lactic acid (PLLA) microspheres have been reported for treatment of liver malignancies. A disadvantage of holmium-loaded PLLA microspheres is the limited loading capacity of holmium. The average holmium loading in these microspheres is ~17% (w/w). $^{165}$Ho and $^{164}$Dy containing magnetic nanoparticles with anticancer drugs can be used for magnetically targeted radiotherapy and chemotherapy at the same time. This application seeks to solve this problem by providing nanoparticles with high drug loading capacity which can provide efficient radiotherapy. In some embodiments, nanoparticles associated with radiosensitizers, as disclosed in this application, are capable of mediating toxic effects when the nanoparticles emit radiation at sub-toxic (subtherapeutic) levels.

BRIEF SUMMARY OF THE INVENTION

Iron garnet particles and iron garnet nanoparticles (np) containing various activatable nuclides, such as holmium-165 ($^{165}$Ho) and dysprosium-164 ($^{164}$Dy), are disclosed in this application. The iron garnet (e.g., HoIG and DyIG) nanoparticles and particles can be prepared using hydroxide co-precipitation methods. In some embodiments, radiosensitizers can be loaded on radioactive magnetic nanoparticles and particles, optionally, coated with suitable lipid bilayers. Methods of using the disclosed particles and nanoparticles for mediating therapeutic benefit in diseases responsive to radiation therapy are also provided. Another aspect of the invention provides films, electrospun fabrics or bandage coverings for the delivery of radiation to the site of a skin lesion amenable to treatment with radiation (e.g., skin cancers or psoriasis).

BRIEF DESCRIPTION OF THE DRAWINGS

The patent or application file contains at least one drawing executed in color. Copies of this patent or patent application publication, with color drawing(s), will be provided by the Office upon request and payment of the necessary fee.

The following terms may be used interchangably within this application: cis-HoIG and HoIG-cisplatin; carbo-HoIG and HoIG-carboplatin; and oxa-HoIG and HoIG-oxaliplatin.

FIGS. 16A-16F. $^{166}$Ho-containing electrospun polymer nanofibrous mats. Pieces cut from one mat (FIG. 16A) before and after neutron activation for (FIG. 16B) 0.5 h, (FIG. 16C) 1.0 h, (FIG. 16D) 2.0 h and (FIG. 16E) 4.0 h in a thermal neutron flux of approximately $3.5 \times 10^{12}$ n/cm$^2$·s in a 1 MW nuclear reactor. FIG. 16F shows radioactivity of $^{166}$Ho-nanoparticles (HoIG) and 33% and 50% (w/w)$^{166}$Ho-containing electrospun polymer nanofibrous mats plotted against $(1-e^{-\lambda T})$.

(FIGS. 24A and 24B) 10% HoYIG loaded electrospun fiber mats.

FIG. 37A shows release of NO from nanoparticles (AMS np) and FIG. 37B shows release of NO from bandages containing $^{165}$Ho (HoIG-AN/VIM). These materials need further optimization and study; however, FIG. 37B does demonstrate that NO and $^{165}$Ho can be incorporated into one construct. Furthermore, NO can be released over the 24 h period that tumors will be exposed to the bandage, FIG. 37B, after heat activation.

DETAILED DISCLOSURE OF THE INVENTION

Figure 1A:
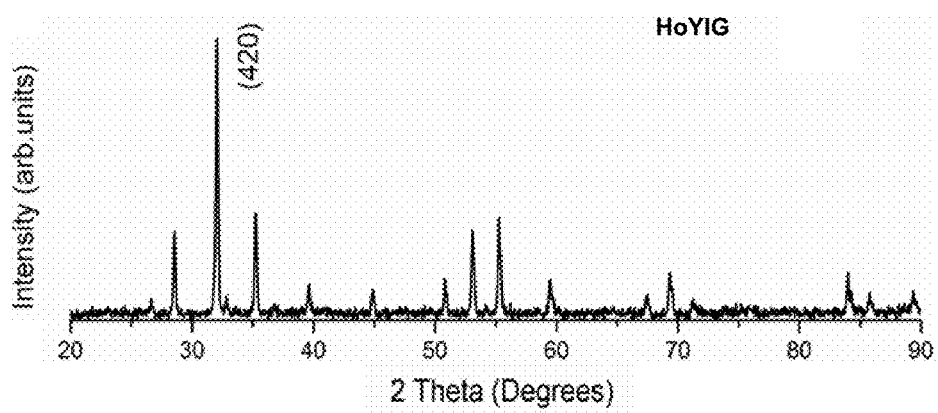
FIGS. 1A-1B. PXRD pattern of (FIG. 1A) HoYIG powder (FIG. 1B) DyYIG powder.

As used herein, the terms "a" or "an" or "the" may refer to one or more than one. For example, "a" marker can mean one marker or a plurality of markers.

As used herein, the term "about," when used in reference to a measurable value such as an amount of mass, dose, time, temperature, and the like, is meant to encompass variations of ±10%, ±5%, ±1%, ±0.5%, or even ±0.1% of the specified amount.

As used herein, the term "activatable nuclide" refers to a non-radioactive atom that may be activated to produce a radionuclide. For example, the disclosed iron garnet nanoparticles and particles can be prepared using nuclides (e.g., holmium dysprosium, lanthanum, praseodymium, samarium and/or rhenium) that become activated by neutron irradiation. Certain embodiments provide for iron garnet nanoparticles and iron garnet particles that contain holmium, dysprosium and yttrium. Other embodiments provide for iron garnet nanoparticles and iron garnet particles that do not contain yttrium (e.g., the iron garnet nanoparticles contain various lanthanides that can be activated by neutron irradiation with the provision that the iron garnet nanoparticles do not contain yttrium). Various other embodiments provide for the omitting one or more of the aforementioned nuclides (e.g., holmium dysprosium, lanthanum, praseodymium, samarium and/or rhenium) from iron garnet particles and nanoparticles formed according to this disclosure where the iron garnets are formed with a combination of lanthanides. The following table provides examples of activatable nuclides and the corresponding radionuclides.

| Activatable nuclide | Radionuclide |
| --- | --- |
| Yttrium-89 | Yttrium-90 |
| Lanthanum-139 | Lanthanum-140 |
| Praseodymium-141 | Praseodymium-142 |
| Samarium-152 | Samarium-153 |
| Dysprosium-164 | Dysprosium-165 |
| Holmium-165 | Holmium-166 |
| Rhenium-185 | Rhenium-186 |
| Rhenium-187 | Rhenium-188 |

As used herein, the term "and/or" refers to and encompasses any and all possible combinations of one or more of the associated listed items, as well as the lack of combinations when interpreted in the alternative ("or").

As used herein, the term "cancer" refers to any benign or malignant abnormal growth of cells. Examples include, without limitation, breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma. In some embodiments, the cancer is selected from the group of tumor-forming cancers.

As used herein, the terms "increase" and "enhance" (and any grammatical variants of these terms) refer to an increase in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 100%, 125%, 150%, 175%, 200%, 250%, 300% or more. For example, radiosensitizers, such as cisplatin, oxaliplatin and carboplatin, increase the toxic effects of activated HoIG nanoparticles disclosed herein.

As used herein, the terms "inhibit" and "reduce" (and any grammatical variants of these terms) refer to a decrease in the specified parameter of at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, 99% or more.

As used herein, the term "nanoparticle" (and any grammatical variant thereof) refers to a particle that is about 0.1 nm to about 200 nm in diameter. The term "particle" (and any grammatical variant thereof) refers to iron garnet particles that are between about 0.1 nm and 1 μm in diameter. In some embodiments, the nanoparticle has a diameter of from about 5 nm to about 100 nm or from about 5 nm to about 200 nm. In some embodiments, the particle or nanoparticle is about 1, 2, 3, 4, 5, 6, 7, 8, 9, 10, 15, 20, 25, 30, 35, 40, 45, 50, 55, 60, 65, 70, 75, 80, 85, 90, 95, 100, 125, 150, 175, 200, 225, 250, 275, 300, 325, 350, 375, 400, 425, 450, 475, 500, 550, 600, 650, 700, 750, 800, 850, 900, 950, 975 or 999 nm in diameter. Particles and nanoparticles disclosed herein refer to iron garnet nanoparticles (IG np) or iron garnet particles into which particular lanthanide nuclides are complexed. These particles and nanoparticles may be made with yttrium, holmium, lanthanum, praseodymium, samarium, rhenium and/or dysprosium dispersed within the iron garnet. Certain embodiments provide for iron garnet nanoparticles or iron garnet particles that contain holmium, dysprosium and yttrium. Other embodiments provide for iron garnet nanoparticles or iron garnet particles that do not contain yttrium (e.g., the iron garnet nanoparticles or iron garnet particles contain various lanthanides that can be activated by neutron irradiation with the provision that the iron garnet nanoparticles do not contain yttrium). Various other embodiments provide for the omitting one or more of the aforementioned activatable nuclides (e.g., holmium, dysprosium, lanthanum, praseodymium, samarium and/or rhenium) from iron garnets formed according to this disclosure where the iron garnets are formed with a combination of lanthanides.

In some embodiments, the disclosed iron garnet nanoparticles or iron garnet particles are treated with materials that are "radiosensitizers". Radiosensitizer compounds are drugs that act in combination with radiation to produce improved response, usually by making DNA more susceptible to radiation, or extending the life of free radicals produced by the radiation. Another type of radiation enhancer includes elements or compounds that interact directly with the radiation to cause more tissue damage by increasing the absorption or scattering of the radiation, causing more local energy deposition by production of secondary electrons, alpha particles, Auger electrons, ionizations, fluorescent photons, and free radicals, for example. For cancer therapy, the purpose is to selectively enhance the dose to the tumor, so these drugs, elements or compounds must be preferentially accumulated in tumor tissue or the tumor tissue must respond in a preferential way, to spare normal tissue. Complexes containing platinum, ruthenium, palladium, iron, cobalt, nickel, copper, rhodium, gold, silver and boron can be used as radiosensitizers in this invention. Some non-limiting examples of radiosensitizers include the platinum complexes cisplatin, oxaliplatin and carboplatin. Iron garnet nanoparticles or iron garnet particles disclosed herein can contain various ratios of radiosensitizers. For example, the particles or nanoparticles can contain the following ranges of activatable nuclide/radionuclide containing IG to radiosensitizer (as a % weight of the nanoparticle): about 40.0% to about 60.0% activatable nuclide/radionuclide containing IG and 0% to about 20% radiosensitizer; about 50.0% to about 60.0% activatable nuclide/radionuclide containing IG and 0% to about 12% radiosensitizer; about 50.0% to about 60.0% activatable nuclide/radionuclide containing IG and about 2.0% to about 7.0% radiosensitizer; and about 50.0% to about 60.0% activatable nuclide/radionuclide containing IG and about 2.0% to about 12.0% radiosensitizer. Certain non-limiting examples of activatable nuclide/radionuclide containing IG to radiosensitizers, such as cisplatin, oxalipiatin and carboplatin, are: HoIG: about 55.6% Ho, 0% Pt; cis-HoIG: about 53.9% Ho, about 10.3% Pt; carbo-HoIG: about 51.2% Ho, about 3.2% Pt; and oxa-HoIG: about 52.9% Ho, about 2.2% Pt. As used in this paragraph, the term "activatable nuclide/radionuclide" is used to indicate the weight percent of a nuclide containing IG or the weight percent of a radionuclide containing IG with respect to a radiosensitizer.

Nanoparticles or particles as disclosed herein can be, optionally, be coated with a lipid or phospholipid. The terms "lipid" and "phospholipid"" (and any grammatical variants thereof), as used herein, refer to any of the numerous lipids that contain a diglyceride, a phosphate group, and a simple organic molecule such as choline. Examples of phospholipids include, but are not limited to, phosphatidic acid (phosphatidate) (PA), phosphatidylethanolamine (cephalin) (PE), phosphatidylcholine (lecithin) (PC), and phosphatidylserine (PS), and phosphoinositides which include, but are not limited to, phosphatidylinositol (PI), phosphatidylinositol phosphate (PIP), phosphatidylinositol bisphosphate (PIP2) and phosphatidylinositol triphosphate (PIP3). Additional examples of PC include DDPC, DLPC, DMPC, DPPC, DSPC, DOPC, POPC, DRPC, and DEPC as defined in the art. Phospholipids or lipids used to coat the disclosed IG nanoparticles can be functionalized with various agents, such as polyethylene glycol (PEG) for form pegylated lipids or pegylated phospholipids. Various targeting agents, as disclosed herein, can then be covalently attached to functionalized lipids and/or phospholipids (e.g., pegylated lipids and/or phospholipids) to facilitate targeting of the IG nanoparticles to a specific cell (e.g., a cancer cell).

In some embodiments, the disclosed iron garnet particles and iron garnet nanoparticles are used at doses that emit "subtherapeutic" levels of radiation. As used herein, the term "subtherapeutic" (and any grammatical variant thereof) refers to levels of radiation that minimally effect the viability of the treated cells. In these embodiments, the viability of the treated cells is reduced by 15% or less. However, when the disclosed IG nanoparticles or IG particles that emit "subtherapeutic" levels of radiation are used in combination with a radiosensitizer, cell viability is decreased by at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or at least 97% and the therapeutic effects of the particles of nanoparticles emitting subtherapeutic levels of radiation is increased or enhanced as described above. Other embodiments provide for a cell viability decrease of between 20% and 80% when IG nanoparticles or IG particles emitting subtherapeutic levels of radiation are used in combination with a radiosensitizer.

As used herein, "pharmaceutically acceptable" means that the material is suitable for administration to a subject and will allow a desired treatment to be carried out without giving rise to unduly deleterious side effects. The severity of the disease and the necessity of the treatment are generally taken into account when determining whether any particular side effect is unduly deleterious.

As used herein, the term "radiotherapeutic nanoparticle" refers to a nanoparticle that emits radiation. As used herein, the term "radiotherapeutic particle" refers to a particle that emits radiation. The term "radionuclide" refers to an atom with an unstable nucleus, which undergoes radioactive decay and emits gamma rays and/or other subatomic particles (e.g., beta particles). $^{166}$Ho and $^{165}$Dy are examples of such radionuclides (see, also, the table provided above for additional examples of radionuclides). In certain embodiments, the radiotherapeutic nanoparticles and/or radiotherapeutic particles are activated by neutron irradiation such that the nanoparticles or particles emit low "subtherapeutic" levels of radiation, and have little to no effect on cells surrounding the location of the nanoparticles. In other embodiments, the radiotherapeutic nanoparticles and/or radiotherapeutic particles are irradiated/activated with neutron irradiation such that therapeutic levels of radiation are emitted by the radiotherapeutic nanoparticle.

As used herein, the term "subject" (and grammatical variants thereof) refers to mammals, avians, reptiles, amphibians, or fish. Mammalian subjects may include, but are not limited to, humans, non-human primates (e.g., monkeys, chimpanzees, baboons, etc.), dogs, cats, mice, hamsters, rats, horses, cows, pigs, rabbits, sheep and goats. Avian subjects may include, but are not limited to, chickens, turkeys, ducks, geese, quail, pheasants, and birds kept as pets (e.g., parakeets, parrots, macaws, cockatoos, and the like). In particular embodiments, the subject is from an endangered species. In particular embodiments, the subject is a laboratory animal. Human subjects may include neonates, infants, juveniles, adults, and geriatric subjects.

As used herein, the term "therapeutically effective" refers to some improvement or benefit to the subject. Alternatively stated, a "therapeutically effective amount" is an amount that will provide some alleviation, mitigation, or decrease in at least one clinical symptom in the subject (e.g., reduced tumor size, decreased incidence of metastasis, etc. for subjects having a form of cancer). Those skilled in the art will appreciate that the therapeutic effects need not be complete or curative, as long as some therapeutic benefit is provided to the subject. The concentration of stable activatable particles (or nanoparticles) and/or radiotherapeutic agent in the pharmaceutical composition may vary widely (i.e., from less than about 0.05% to about 90% or more by weight) in accordance with the particular mode of administration, the disease(s)/disorder(s)/symptom(s) being treated, the age/weight of the subject, etc.

As used herein, the terms "treatment," "treat," and "treating" refer to providing a subject with the particles and/or nanoparticles disclosed herein in an effort to alleviate, mitigate, or decrease at least one clinical symptom in the subject. As is apparent to those skilled in the art, the disclosed iron garnet nanoparticles and iron garnet particles can be guided to a target site by magnetic manipulation.

The present invention provides radiotherapeutic nanoparticles and radiotherapeutic particles. In particular embodiments, the present disclosure provides iron garnet nanoparticles or iron garnet particles that contain an activatable nuclide, such as holmium and/or dysprosium. Thus, one aspect of the invention provides a stable activatable iron garnet nanoparticle or particle comprising, consisting essentially of or consisting of an activatable nuclide precursor. A further aspect of the invention provides a pharmaceutical composition comprising, consisting essentially of or consisting of the disclosed iron garnet nanoparticles and/or iron garnet particles and a pharmaceutically acceptable carrier.

As used herein, the term "pharmaceutically acceptable carrier" refers to any suitable pharmaceutical diluent and/or excipient (for example, phosphate buffered saline and/or isotonic saline solution). Other examples of pharmaceutically acceptable carriers, diluents and excipients may be found, for example, in Ansel's Pharmaceutical Dosage Forms and Drug Delivery Systems (9th Ed., Lippincott Williams and Wilkins (2010)), Pharmaceutical Sciences (18th Ed., Mack Publishing Co. (1990) or Remington: The Science and Practice of Pharmacy (21st Ed., Lippincott Williams & Wilkins (2005)).

The pharmaceutical composition may also contain various other materials, such as pH-adjusting and/or buffering agents, tonicity-adjusting and/or buffering agents and lipid-protective agents (e.g., agents that that protect lipids against free-radical damage, such as alpha-tocopherol). The pharmaceutical composition may be formulated so as to be suitable for administration via any known method, including, but not limited to, oral, intravenous (i.v.), subcutaneous, intramuscular, intrathecal, intraperitoneal (i.p.), intra-arterial, intratumoral, intrarectal, intravaginal, intranasal, intragastric, intratracheal, sublingual, transcutaneous and intrapulmonary.

The present invention provides methods of treating a disorder responsive to radiotherapeutic treatment comprising administering to said subject a therapeutically effective amount of a radiotherapeutic nanoparticle and/or a radiotherapeutic particle (optionally in the form of a pharmaceutical composition) of the present invention. In some embodiments, the radiotherapeutic nanoparticle or radiotherapeutic particle is an iron garnet nanoparticle or particle, such as HoIG or DyIG. The radiotherapeutic nanoparticle or radiotherapeutic particle may be administered using any suitable method known in the art, including, but not limited to, oral, intravenous (i.v.), subcutaneous, intramuscular, intrathecal, intraperitoneal (i.p.), intra-arterial, intratumoral, intrarectal, intravaginal, intranasal, intragastric, intratracheal, intratumoral, sublingual, transcutaneous and intrapulmonary. In some embodiments, the radiotherapeutic agent (radiotherapeutic nanoparticles and/or radiotherapeutic particles) is administered via intraperitoneal injection. In other embodiments, the radiotherapeutic agent is injected directly into a tumor. Yet other embodiments permit the use of a magnet to target or guide the disclosed radiotherapeutic nanoparticles and/or radiotherapeutic particles to a target site. Where targeting agents are associated with the disclosed IG nanoparticles or IG particles, such targeting agents provide a means for guiding the IG nanoparticles and/or IG particles to a target tissue or cell (e.g., an anti-CD20 antibody can be used to guide an HoIG or DyIG nanoparticle to a malignant B-cell for the treatment of Hodgkin's lymphoma).

Methods of the present invention may be used to treat any suitable disorder known in the art, including, but not limited to, bacterial infections, viral infections, cancer, trigeminal neuralgia, severe thyroid eye disease, pterygium, pigmented villonodular synovitis, vascular restenosis, heterotopic ossification, rheumatoid arthritis, synovial osteochondromatosis, synovial chondromatosis and hemathrosis. In some embodiments, the disorder is a hematological cancer, such as acute myeloid leukemia, chronic myeloid leukemia, hairy cell leukemia, lymphoblastic leukemia, lymphocytic leukemia, AIDS-related lymphoma, Burkitt's lymphoma, cutaneous T-cell lymphoma, Hodgkin's lymphoma, Non-Hodgkin's lymphoma, primary central nervous system lymphoma or myeloma. In some embodiments, the disorder is a solid cancer, such as anal cancer, basal cell carcinoma, bile duct cancer, bladder cancer, bone cancer, brain cancer (e.g., cerebellar astrocytoma, ependymoma, glioma, medulloblastoma, neuroblastoma, etc.), breast cancer (e.g., metastatic breast cancer), cervical cancer, colon cancer, endometrial cancer, esophageal cancer, eye cancer (e.g., intraocular melanoma, retinoblastoma, etc.), gallbladder cancer, gastrointestinal cancer, heart cancer, kidney cancer (e.g., renal cell carcinoma), laryngeal cancer, lip cancer, liver cancer, lung cancer (e.g., non-small cell lung cancer, small cell lung cancer, etc.), melanoma, mesothelioma, oral cancer, ovarian cancer, pancreatic cancer, parathyroid cancer, peritoneal carcinomatosis, pharyngeal cancer, prostate cancer, rectal cancer, skin cancer (e.g., Merkel cell carcinoma, squamous cell carcinoma, etc.), stomach cancer, throat cancer, thyroid cancer, urethral cancer, uterine cancer, vaginal cancer or vulvar cancer.

Because holmium and dysprosium are also emitters of beta particles, the disclosed nanoparticles find use in methods of identifying or imaging the presence of one or more sites of various disorders, including, but not limited to, bacterial infections, viral infections, cancer, trigeminal neuralgia, severe thyroid eye disease, pterygium, pigmented villonodular synovitis, vascular restenosis, heterotopic ossification, rheumatoid arthritis, synovial osteochondromatosis, synovial chondromatosis and hemathrosis. In some embodiments, the disorder is a hematological cancer, such as acute myeloid leukemia, chronic myeloid leukemia, hairy cell leukemia, lymphoblastic leukemia, lymphocytic leukemia, AIDS-related lymphoma, Burkitt's lymphoma, cutaneous T-cell lymphoma, Hodgkin's lymphoma, Non-Hodgkin's lymphoma, primary central nervous system lymphoma or myeloma. In some embodiments, the disorder is a solid cancer, such as anal cancer, basal cell carcinoma, bile duct cancer, bladder cancer, bone cancer, brain cancer (e.g., cerebellar astrocytoma, ependymoma, glioma, medulloblastoma, neuroblastoma, etc.), breast cancer (e.g., metastatic breast cancer), cervical cancer, colon cancer, endometrial cancer, esophageal cancer, eye cancer (e.g., intraocular melanoma, retinoblastoma, etc.), gallbladder cancer, gastrointestinal cancer, heart cancer, kidney cancer (e.g., renal cell carcinoma), laryngeal cancer, lip cancer, liver cancer, lung cancer (e.g., non-small cell lung cancer, small cell lung cancer, etc.), melanoma, mesothelioma, oral cancer, ovarian cancer, pancreatic cancer, parathyroid cancer, peritoneal carcinomatosis, pharyngeal cancer, prostate cancer, rectal cancer, skin cancer (e.g., Merkel cell carcinoma, squamous cell carcinoma, etc.), stomach cancer, throat cancer, thyroid cancer, urethral cancer, uterine cancer, vaginal cancer or vulvar cancer. In this aspect of the invention, various known techniques can be used to image a subject, including, but not limited to, magnetic resonance imaging (MRI), X-ray computed tomography (CT), Single Photon Emission Computed Tomography (SPECT) and micro-computed tomography (micro-CT).

As would be apparent to those skilled in the art, the IG nanoparticles disclosed in this application are magnetizable and are suitable materials for magnetic drug delivery. Thus, the disclosed nanoparticles can be delivered to specific targets within the body by use of magnetic fields or stationary magnets outside the body. Magnetic nanoparticles are routinely used for the treatment of shallow tumors and have been tested for safety and efficacy in animal and human clinical trials. Thus, the disclosed nanoparticles can be injected into a subject, distributed by the circulatory system, and then captured and concentrated at a desired tumor location by magnetic fields or magnets located near or around the tumor. The disclosed nanoparticles can also be delivered to deep tissue tumor sites, such as the lungs, intestines, and liver, through the use of magnetic fields, such as those disclosed in U.S. Pat. No. 8,579,787 (the disclosure of which is hereby incorporated by reference in its entirety). The '787 patent discloses systems and methods for using magnetic fields to contain and deliver magnetizable therapeutic, diagnostic or prophylactic agents in a target volume within a patient's body, or to move such magnetizable agents through a target volume within a patient's body. As would be apparent to those skilled in the art, any known technique for delivering magnetizable nanoparticles to a target site can be used to deliver the IG nanoparticles disclosed herein.

Yet another aspect of the invention provides for a film, electospun fabric or bandage that is impregnated with IG nanoparticles disclosed herein. As used herein, the term "bandage" (and any grammatical variants thereof) refers to a wound covering into which the disclosed IG nanoparticles have been impregnated. Such coverings can be a patch or film. In some embodiments of this aspect of the invention, a bandage or film is produced by dissolving the disclosed IG nanoparticles and a polymer in a solvent, applying a stable nuclide solution on a release paper by a coater and drying. The film/patch/bandage may then be irradiated with neutrons in a nuclear reactor. Another embodiment of the disclosed invention provides using an electrospinning technique to prepare $^{165}$Ho and/or $^{164}$Dy nanoparticle-loaded nanofibers that can be electrospun into a bandage with uniform particle distribution. Various other techniques for forming such bandages are known in the art (see, for example, U.S. Pat. Nos. 4,946,435 and 6,350,226, each of which is hereby incorporated by reference in its entirety, and U.S. Patent Application Publication 2013/0337033, which is also hereby incorporated by reference in its entirety). In various embodiments, nanoparticles that are used in the manufacture of a film, electrospun fabric or bandage can have a size of less than about 500 nm, less than about 400 nm, less than about 300 nm, less than about 200 nm, less than about 100 nm, less than about 50 nm or range in size from about 5 nm to about 100 nm or from about 5 nm to about 200 nm.

As used herein, the phrases "relatively uniform distribution of said nanoparticles/particles within said film, electrospun fabric or bandage" and "relatively uniform radiation across the surface area of said film, electrospun fabric or bandage" relate to the distribution of the nanoparticles/particles and the emitted radiation from said nanoparticles/particles within the film, electrospun fabric or bandage. In this regard, the variance with respect to the number of nanoparticles or the amount of emitted radiation for a given surface area of the film, electrospun fabric or bandage varies by less than about 30%, less than about 25%, less than about 15%, less than about 10%, less than about 5% or less than about 1%. In certain embodiments, the variance with respect to the number of nanoparticles/particles or the amount of emitted radiation for a given surface area of the film, electrospun fabric or bandage varies by about 0.01% to about 5%, about 0.01% to about 2.5%, about 0.01% to about 1%, about 0.1% to about 5%, about 0.1% to about 2.5%, about 0.1% to about 1%, about 0.05% to about 5% or about 0.5% to about 2.5%.

Various additional embodiments of this aspect of the invention provide for the inclusion of additional wound-healing agents within the disclosed bandages. For example, nitrous oxide (NO) can be incorporated into a bandage as disclosed in U.S. Patent Application Publication 2013/0337033. As disclosed therein, bandage and gauze materials (herein also referred to as electrospun fabrics) can be prepared from fibers spun from acrylonitrile-based co- and ter-polymers, such as vinylimidazole, butyl acrylate, isoprene, butadiene, and caprolactam (other polymers are also useful in this regard and known in the art; see, for example, Riccio and Schoenfisch, Chem. Soc. Rev., 2012, 41:3731-3741, which is hereby incorporated by reference in its entirety). Once the polymer is spun into fibers, it is exposed to high pressure of NO, allowing the formation of a NO molecular donor group, a diazeniumdiolate (NONOate). These NONOates release two molar equivalents of NO spontaneously upon exposure to physiological conditions. Other agents that can be included within the bandages disclosed herein include antibiotics, anti-microbial agents, dialkylcarbamoylchloride, povidone-iodine, silver and growth factors, such as epidermal growth factor (EGF), platelet-derived growth factor (PDGF), fibroblast growth factor (FGF), transforming growth factor (TGF-$\beta$1), insulin-like growth factor (IGF-1), human growth hormone and granulocyte-macrophage colony-stimulating factor (GM-CSF); see, for example, Boateng et al., J. Pharmaceutical Sciences, 2008, 97:2892-2993, which is hereby incorporated by reference in its entirety, particularly with respect to active ingredients used in wound management at pages 2905-2907. The resulting films, electrospun fabrics and bandages can be used for the treatment of skin conditions amenable to treatment with radiation with the concomitant application of wound-healing agents, such as NO. Skin conditions suitable for such treatment include psoriasis, melanomas and other skin cancers. Where the film, electrospun fabric or bandage is used for the treatment of skin cancer, radiosensitizers, such as platinum, ruthenium, palladium, iron, cobalt, nickel, copper, rhodium, gold, silver and/or boron, can also be incorporated within the film, electrospun fabric or bandage and therapeutic or subtherapeutic levels of radiotherapeutic nanoparticles can be used for the treatment of skin cancer. In addition to platinum, ruthenium, palladium, iron, cobalt, nickel, copper, rhodium, gold, silver and/or boron, NO (which also provides benefits as a wound-healing agent) can function as a radiosensitizer as well. Alternatively, the radiosensitizers can be incorporated into the nanoparticles used in the manufacture of the film, electrospun fabric or bandage.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Nanoparticle Synthesis

Synthesis of holmium yttrium iron garnet (HoYIG), holmium iron garnet (HoIG), dysprosium yttrium iron garnet (DyYIG) and dysprosium iron garnet (DyIG) nanoparticles:

A hydroxide co-precipitation method can be used to synthesize HoYIG, HoIG, DyYIG and DyIG nanoparticles. Water-soluble salts of holmium, dysprosium, yttrium and iron were mixed in the presence of cationic, anionic, or non-ionic surfactant and/or capping agents and a suitable base was used to precipitate HoYIG and DyYIG. The precipitate can be annealed at high temperature in order to get a magnetic crystalline product. The same procedure will be followed without yttrium salt to prepare HoIG and DyIG nanoparticles.

Stoichiometric mixtures (5:1.5:1.5) of 1M nitrates of iron (III) (10 mL), holmium (III) (5 mL), and yttrium (III) (3 mL) were mixed with ethylene glycol (21 mL) at room temperature with stirring. Then 6M NaOH (10 mL) were added dropwise to form the HoYIG precipitate. The product was centrifuged and washed with de-ionized water, then dried at 100° C. overnight. The HoYIG was annealed in air at 900° C. for 3 h. Stoichiometric mixtures (5:1.5:1.5) of 1M nitrates of iron (III) (10 mL), dysprosium (III) (5 mL), and yttrium (III) (3 mL) were used to synthesize DyYIG nanoparticles based on the method described above.

These products were characterized using x-ray diffraction (XRD) on a Rigaku Ultima IV diffractometer using Cu K$\alpha$ radiation. The average crystallite size of the powders was estimated from corresponding XRD data using Scherrer formula. Scanning electron microscopy (SEM) and energy dispersive X-ray spectroscopy (EDX) analysis was carried out on a Zeiss-LEO model 1530 SEM. The magnetic properties of the garnet nanoparticles and fibers were measured using an MPMS-XL superconducting quantum interference device from Quantum Design.

Figure 1B:
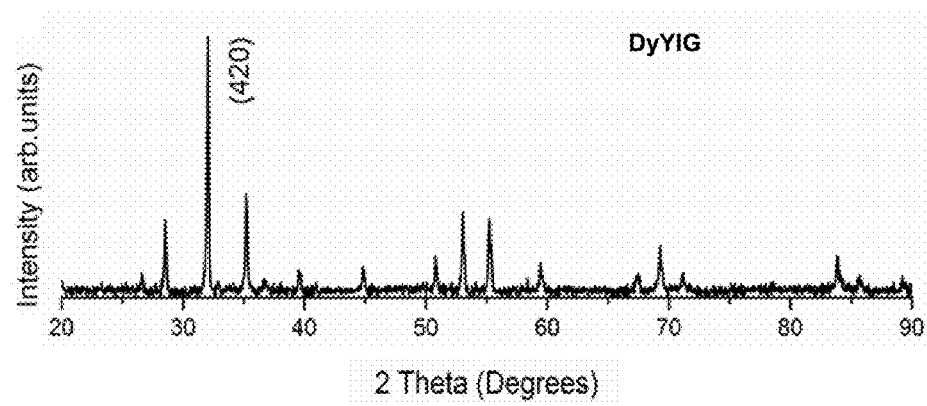
Figure 2A:
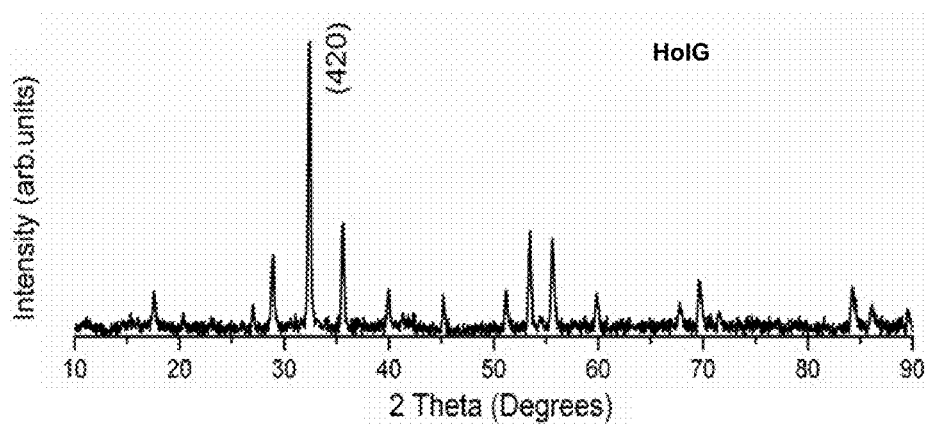
FIGS. 2A-2B. PXRD pattern of (FIG. 2A) HoIG powder (FIG. 2B) $Fe_5Ho_3O_{12}$; JCPDS 00-023-0282.
Figure 2B:
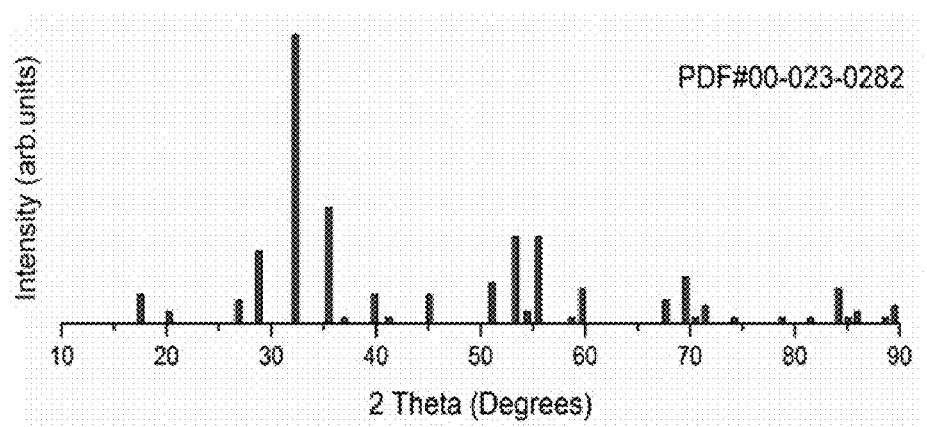
Figure 3A:
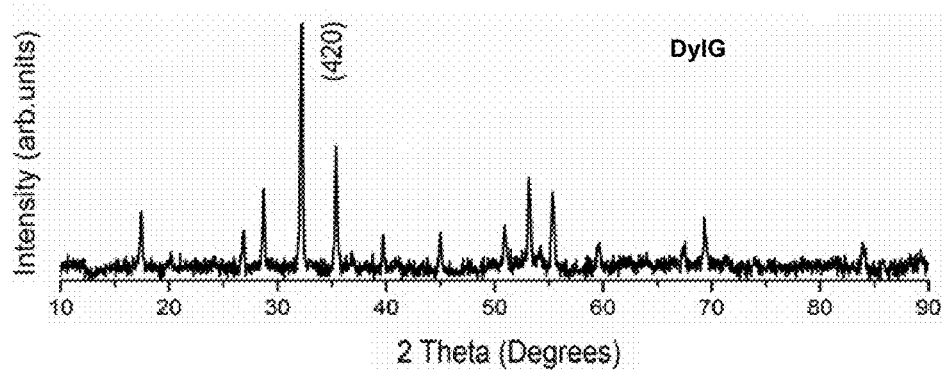
FIGS. 3A-3B. PXRD pattern of (FIG. 3A) DyIG powder (FIG. 3B) $Fe_5Dy_3O_{12}$; JCPDS 01-073-1378.
Figure 3B:
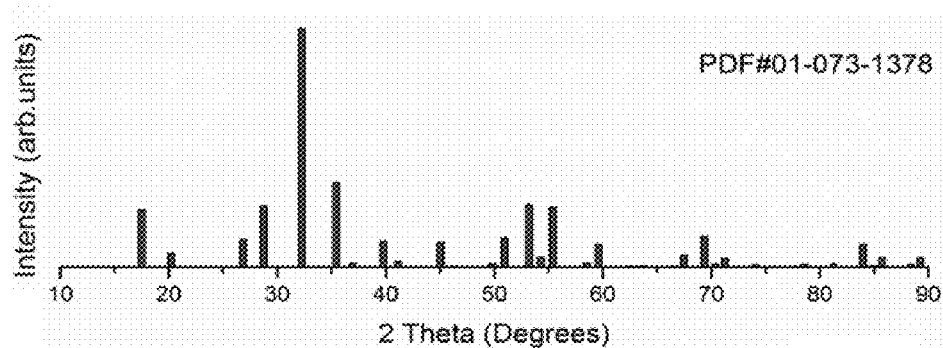
Figure 4:
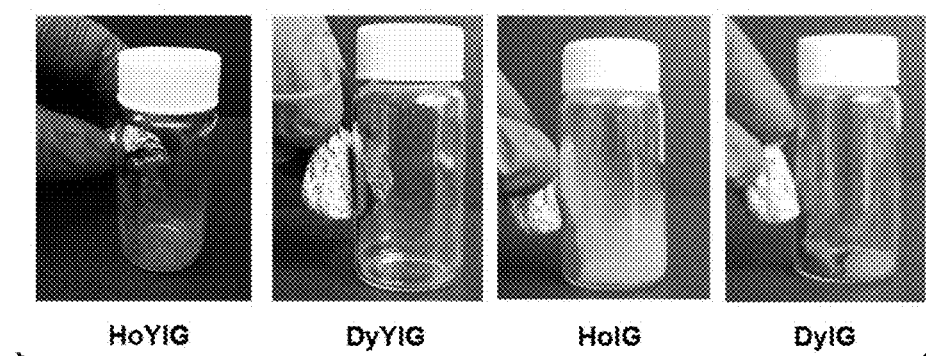
FIG. 4. Digital images of HoYIG, DyYIG, HoIG and DyIG powder attracted to a magnet.

FIGS. 1, 2 and 3 show the PXRD pattern of synthesized HoYIG, DyYIG, HoIG and DyIG. The crystallite sizes were calculated from the PXRD line broadening of the peak (420)

using the Scherrer equation, $D_{hkl}=k\lambda/B\cos\theta$, where $D_{hkl}$ is the particle size in nm, k is a constant (shape factor) with a value of 0.9, B is the width of half maximum, and $\lambda$ is the wavelength of the x-rays. The $D_{hkl}$ values of HoYIG, DyYIG, HoIG and DyIG are about 36, 38, 35 and 38 nm respectively. The synthesized HoYIG, DyYIG, HoIG and DyIG nanoparticles were olive green in color and are magnetic as demonstrated by the attraction of the powder to a magnet as shown in FIG. 4.

Figure 5:
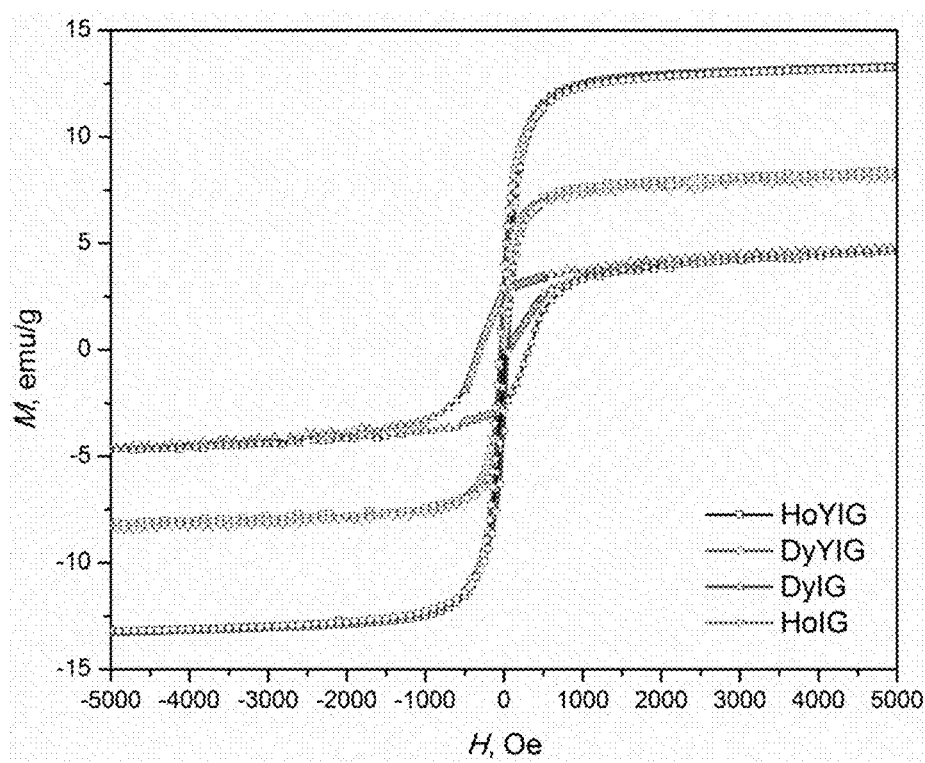
FIG. 5. Magnetic hysteresis loops of the synthesized HoYIG at room temperature.

The magnetization of the synthesized HoYIG, DyYIG, HoIG and DyIG powder was performed at room temperature. Plots of magnetization (M) (normalized to the mass of magnetic material) as a function of magnetic field (H) are shown in FIG. 5. The saturation magnetization (Ms) is defined as the state when an increase in the magnetic field cannot increase the magnetization of the material further and Ms for HoYIG, DyYIG, HoIG and DyIG nanoparticles reached 13, 13, 8, and 4.9 emu/g. Approximately 10 mg of dry HoIG was neutron-activated in a 1 MW TRIGA Mark I nuclear reactor in a thermal neutron flux of approximately $3.5\times10^{12}$ neutrons/cm$^2$·s for 0.5, 1, 2 or 4 h. Gamma radioactivity was then measured, and activities directly after neutron activation were determined to be 56.8, 330.7, 833.8 and 1633.6 µCi mg$^{-1}$, respectively. From this, we calculated that the nanoparticles contained approximately 57.8±26.2% w/w holmium. This correlates with inductively coupled plasma-mass spectrometry (ICP-MS) data, which shows that they contain 35.7% w/w holmium.

Example 2—Platinum (Pt) Drug Loading into Ho-Containing Garnet Nanoparticles

Cisplatin (10 mg) was dissolved in 10 mL simulated body fluid solution (SBF; Marques et al., Dissolution Technologies, 2011, 18:15-28). HoIG nanoparticles (30 mg) were added to cisplatin solution and sonicated for 24 h. The cisplatin-loaded nanoparticles were collected by centrifugation. The amount of remaining cisplatin in the solution was analyzed using UV/Vis and the amount of cisplatin loaded into HoIG nanoparticles was calculated. The cisplatin-loaded HoIG nanoparticles were washed with SBF to remove any unbound cisplatin and the product was dried at 80° C. for 8 h. Cisplatin drug-loaded HoIG nanoparticles were characterized using FTIR-ATR (Table 2).

TABLE 1

FTIR data for cisplatin and cisplatin loaded HoIG nanoparticles

| Wave Number/ cm$^{-1}$ | Cisplatin | Wave Number/ cm$^{-1}$ | Cisplatin_HoIG np |
|---|---|---|---|
| 3201 | N—H stretching (symmetric) | 3140 | N—H stretching (symmetric) |
| 3279 | N—H stretching (asymmetric) | 3245 | N—H stretching (asymmetric) |
| 1538 | N—H bending | 1480 | N—H bending |
| 1294 | Twisting and wagging vibrations of NH$_3$ | 1258 | Twisting and wagging vibrations of NH$_3$ |

Figure 6:
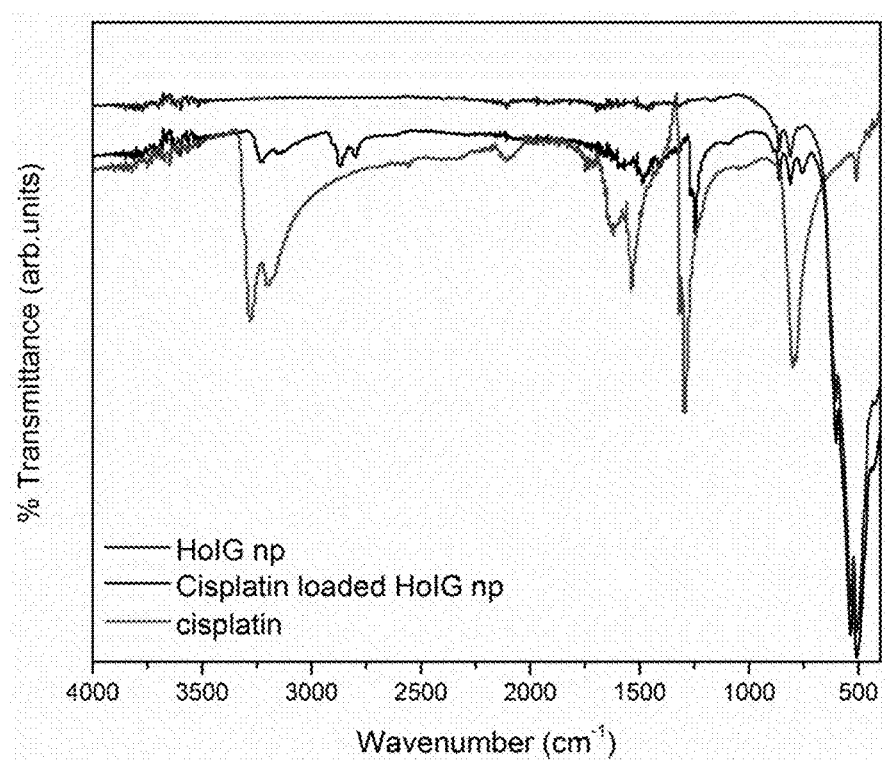
FIG. 6. FTIR spectra of HoIG nanoparticles, cisplatin and cisplatin loaded HoIG nanoparticles.

The red shifts of N—H stretching wave number of cisplatin suggest that bonding of cisplatin to HoIG nanoparticles' surfaces via hydrogen bonding (FIG. 6 and Table 1).

Figure 7:
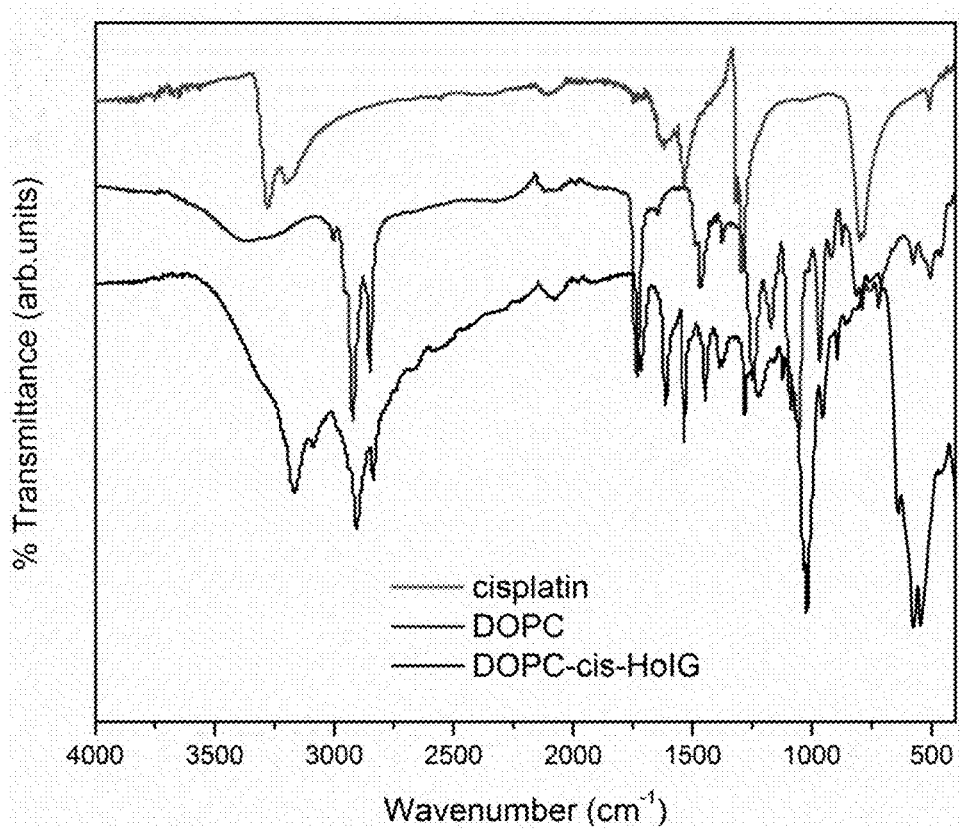
FIG. 7. FTIR spectra of DOPC, cisplatin and cisplatin loaded HoIG nanoparticles.

DOPC lipid coating on cisplatin-loaded HoIG nanoparticles DOPC lipid (30 mg) was dissolved in 5 mL of chloroform. Cisplatin drug-loaded HoYIG nanoparticles (30 mg) were added to DOPC solution and sonicated for 3 h. The solvent was evaporated under slow flow of Ar gas and heated (50° C.). SBF solution (5 mL) was added to the above dried powder and sonicated for another 1 h. The DOPC-coated cisplatin-loaded HoYIG nanoparticles were collected by centrifugation and washed using diethylether to remove excess DOPC. The product was dried at 80° C. for 5 h. DOPC-coated cisplatin drug-loaded HoIG nanoparticles were characterized using FTIR-ATR. The red shifts of P—O and C=O stretching wave number of DOPC suggest that bonding of DOPC to cisplatin via hydrogen bonding (FIG. 7 and Table 2).

TABLE 2

FTIR data for cisplatin, DOPC and DOPC coated cisplatin loaded HoIG nanoparticles

| Wave Number/ cm$^{-1}$ | Cisplatin | Wave Number/ cm$^{-1}$ | DOPC | Wave Number/ cm$^{-1}$ | DOPC-_cisplatin_HoYIG np |
|---|---|---|---|---|---|
| 3201 | N—H stretching (symmetric) | | | 3104 | N—H stretching (symmetric) |
| 3279 | N—H stretching (asymmetric) | | | 3180 | N—H stretching (asymmetric) |
| 1538 | N—H bending | | | 1515 | N—H bending |
| 1294 | Twisting and wagging vibrations of NH$_3$ | | | 1265 | Twisting and wagging vibrations of NH$_3$ |
| | | 1089 | P—O stretching (symmetric) | 1020 | P—O stretching (symmetric) |
| | | 1245 | P—O stretching (asymmetric) | 1220 | P—O stretching (asymmetric) |
| | | 1732 | C=O stretching | 1720 | C=O stretching |

Figure 8:
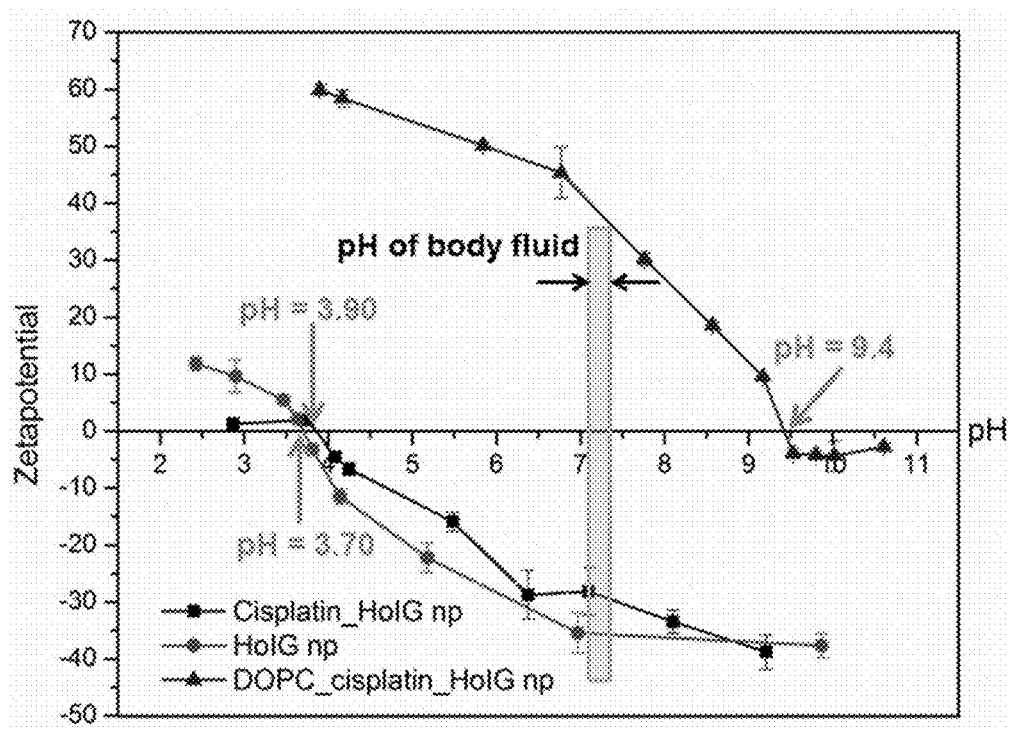
FIG. 8. Zeta potential vs. pH.

FIG. 8 shows the zeta potential vs. pH curves for HoIG, cisplatin-loaded HoIG and DOPC-coated cisplatin-loaded HoIG nanoparticles. The isoelectronic point of HoIG, cisplatin-loaded HoIG and DOPC-coated cisplatin-loaded HoIG are 3.70, 3.90 and 9.40 respectively. The figure also shows that in the pH range of body fluid all these materials are stable since the zeta potential values are above +30 mV and below −30 mV.

Carboplatin (5 mg) was dissolved in simulated body fluid solution (SBF) (10 mL). HoIG nanoparticles (30 mg) were added to carboplatin solution and sonicated for 24 h. The carboplatin-loaded nanoparticles were collected by centrifugation. The amount of remaining carboplatin in the solution was analyzed using UV/Vis and the amount of carboplatin loaded into HoIG nanoparticles was calculated. The carboplatin-loaded HoIG nanoparticles were washed with SBF to remove any unbound carboplatin and the product was dried at 80° C. for 8 h. Carboplatin drug-loaded HoIG nanoparticles were characterized using FTIR-ATR.

Figure 9:
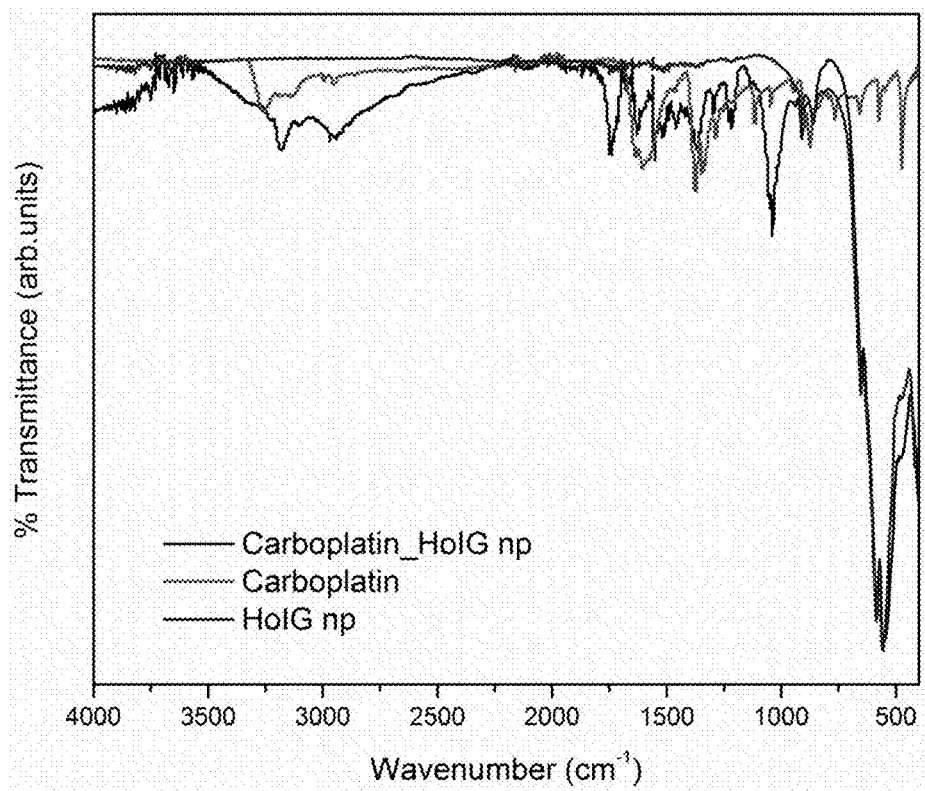
FIG. 9. FTIR spectra of carboplatin, HoIG nanoparticles and carboplatin-loaded HoIG nanoparticles.

The red shifts of N—H stretching wave number of carboplatin suggest that bonding of carboplatin to HoIG nanoparticles' surfaces via hydrogen bonding (FIG. 9 and Table 3). Table 4 provides the weight percentage of Ho and Pt in HoIG, cis-HoIG, carbo-HoIG and oxa-HoIG (determined using inductively coupled plasma-mass spectrometry (ICP-MS)).

TABLE 3

FTIR data for cisplatin and cisplatin loaded HoIG nanoparticles

| Wavenumber/ $cm^{-1}$ | Carboplatin | Wavenumber/ $cm^{-1}$ | Carboplatin_HoYIG np |
|---|---|---|---|
| 3255 | N—H stretching (symmetric) | 3227 | N—H stretching (symmetric) |
| 3134 | N—H stretching (asymmetric) | 3094 | N—H stretching (asymmetric) |

TABLE 4

Weight percentage of Ho and Pt in HoIG, cis-HoIG, carbo-HoIG and oxa-HoIG, determined using inductively coupled plasma-mass spectrometry (ICP-MS)

| Sample | Wt % Pt | Wt % Ho |
|---|---|---|
| HoIG | 0 | 55.6 |
| cis-HoIG | 10.3 | 53.9 |
| carbo-HoIG | 3.2 | 51.2 |
| oxa-HoIG | 2.2 | 52.9 |

DOPC lipid was used to coat carboplatin-loaded HoIG nanoparticles. DOPC lipid (30 mg) was dissolved in 5 mL of chloroform. Carboplatin drug-loaded HoYIG nanoparticles (30 mg) were added to DOPC solution and sonicated for 3 h. The solvent was evaporated under slow flow of Ar gas and heated (50° C.). SBF solution (5 mL) was added to the above dried powder and sonicated for another 1 h. The DOPC-coated carboplatin-loaded HoYIG nanoparticles were collected by centrifugation and washed using diethylether to remove excess DOPC. The product was dried at 80° C. for 5 h. DOPC-coated carboplatin drug-loaded HoIG nanoparticles were characterized using FTIR-ATR (Table 5).

TABLE 5

FTIR data for DOPC and DOPC coated cisplatin loaded HoIG nanoparticles

| Wavenumber/ $cm^{-1}$ | DOPC | Wavenumber/ $cm^{-1}$ | DOPC-_carboplatin_HoYIG np |
|---|---|---|---|
| 1089 | P—O symmetric stretching | 1058 | N—H stretching (symmetric) |
| 1245 | P—O asymmetric stretching | 1219 | N—H stretching (asymmetric) |
| 1732 | C═O stretching | 1714 | N—H stretching (asymmetric) |

Figure 10:
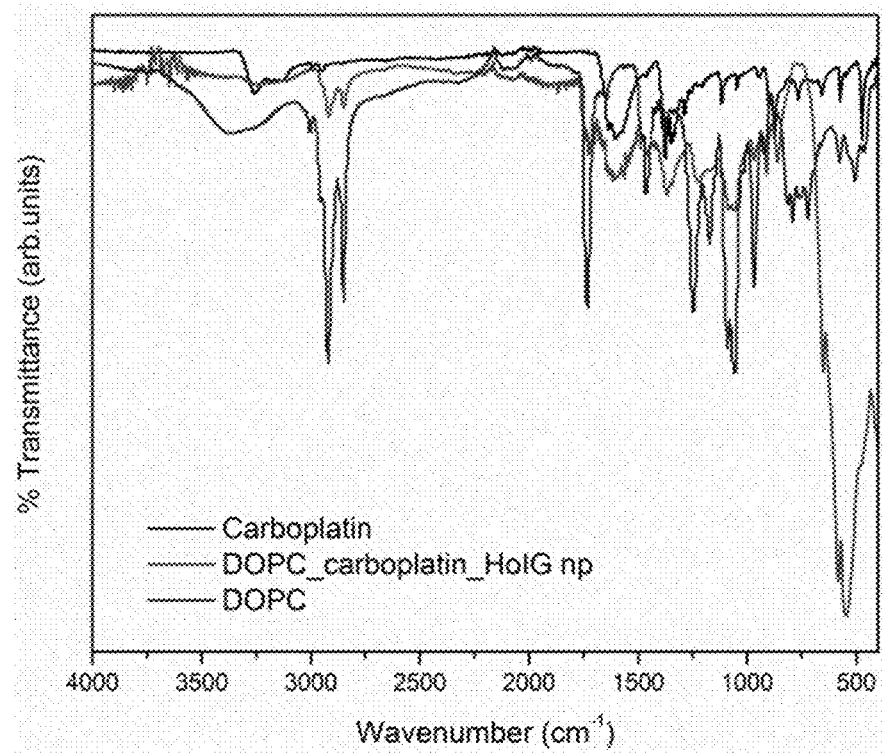
FIG. 10. FTIR spectra of DOPC, carboplatin and carboplatin-loaded HoIG nanoparticles.
Figure 11:
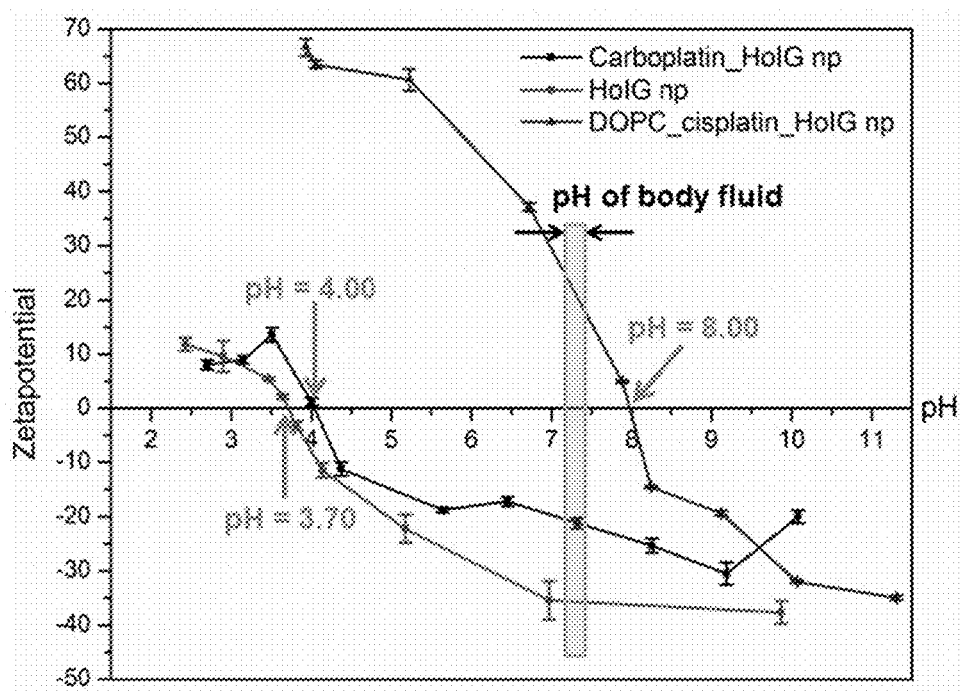
FIG. 11. The zeta potential vs. pH curves for HoIG, carboplatin-loaded HoIG and DOPC coated carboplatin-loaded HoIG nanoparticles.

The red shifts of P—O and C═O stretching wave number of DOPC suggest that bonding of DOPC to carboplatin via hydrogen bonding (FIG. 10 and Table 4). FIG. 11 shows the zeta potential vs. pH curves for HoIG, carboplatin-loaded HoIG and DOPC-coated carboplatin-loaded HoIG nanoparticles. The isoelectronic point of HoIG, carboplatin-loaded HoIG and DOPC-coated cisplatin-loaded HoIG are 3.70, 4.00 and 8.00 respectively. The figure also shows that in the pH range of body fluid all these materials are stable since the zeta potential values are above +20 mV and below −20 mV.

Figure 12A:
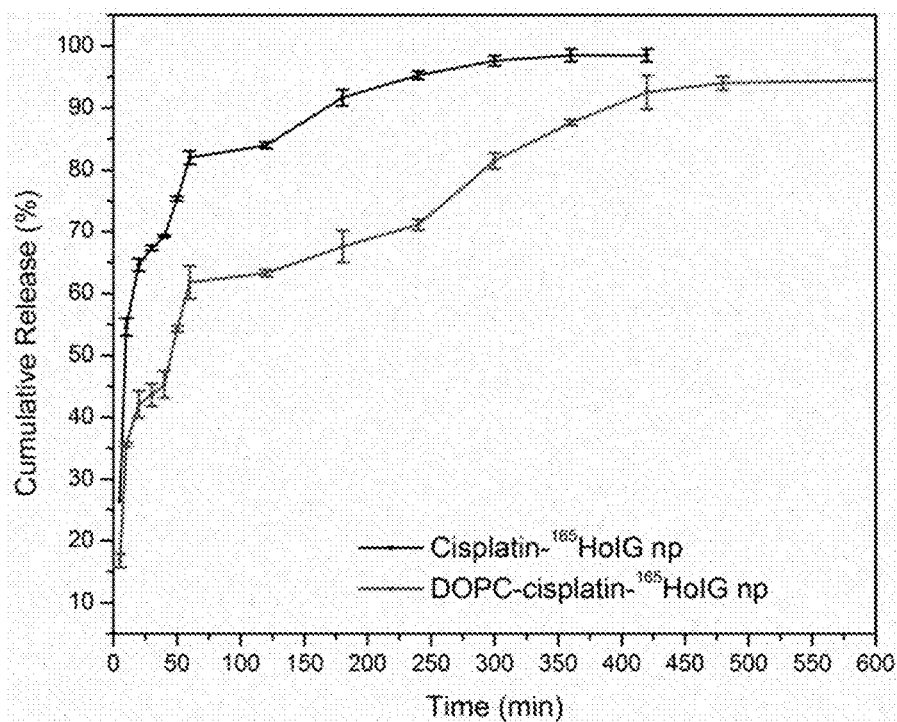
FIGS. 12A-12B. Cumulative release of (FIG. 12A) cisplatin (FIG. 12B) carboplatin.
Figure 12B:
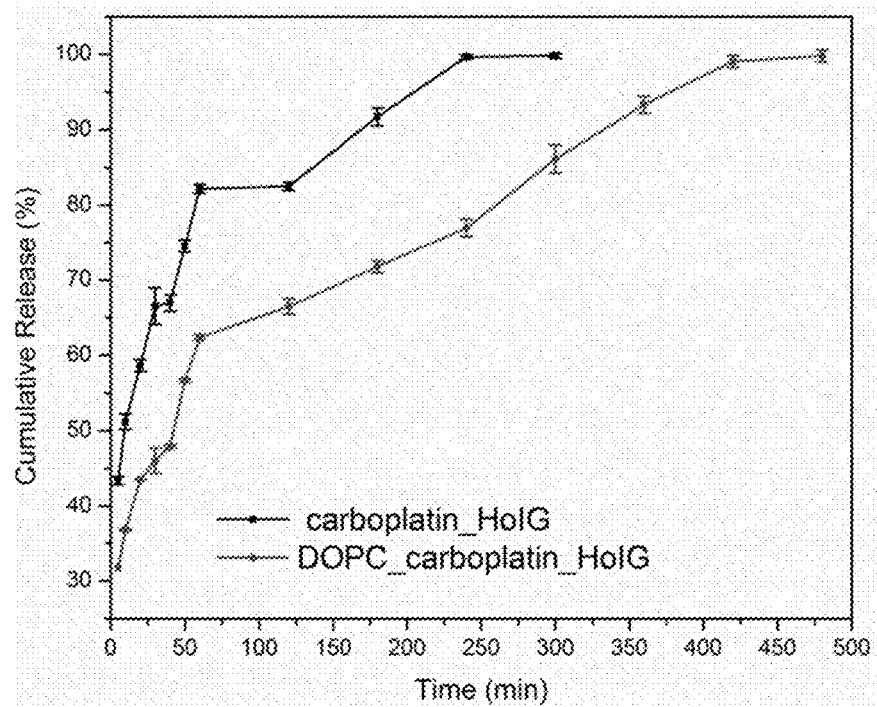
Figure 13A:
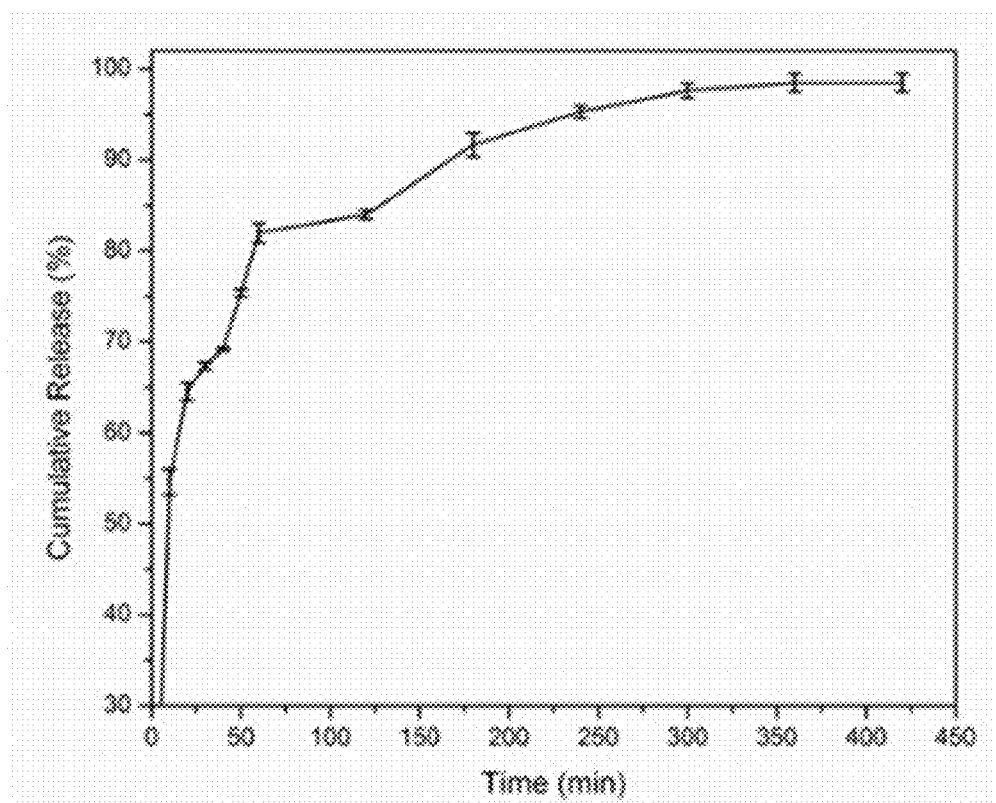
FIGS. 13A-13C. Platinum release profiles from cis-HoIG (FIG. 13A), carbo-HoIG (FIG. 13B) and oxa-HoIG (FIG. 13C).
Figure 13B:
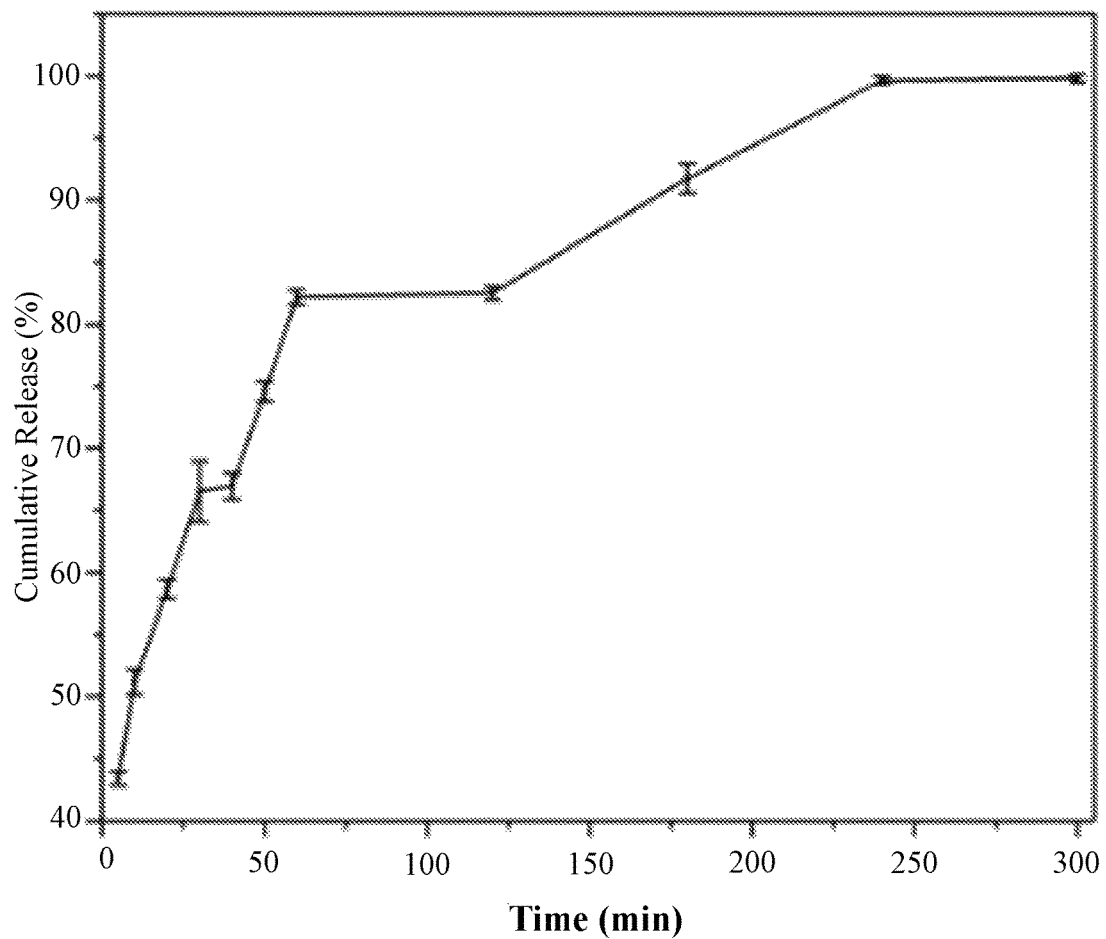
Figure 13C:
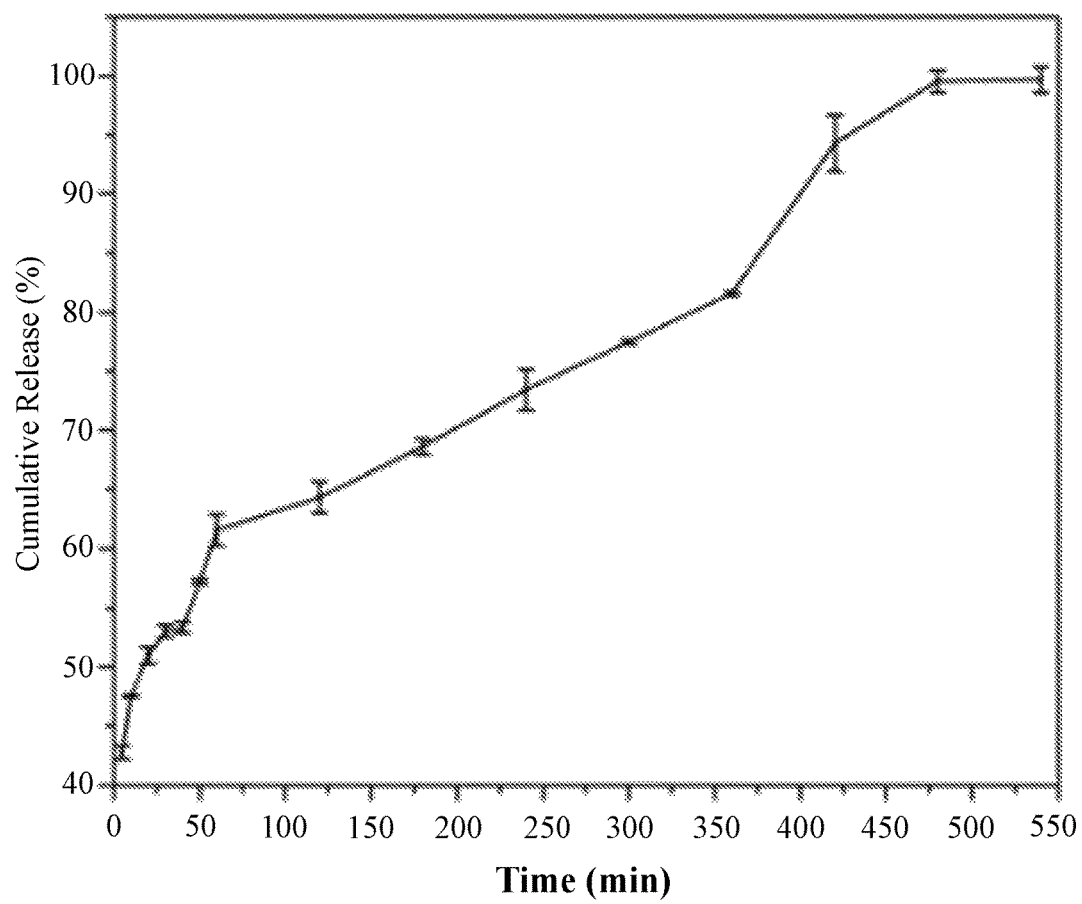
Figure 14A:
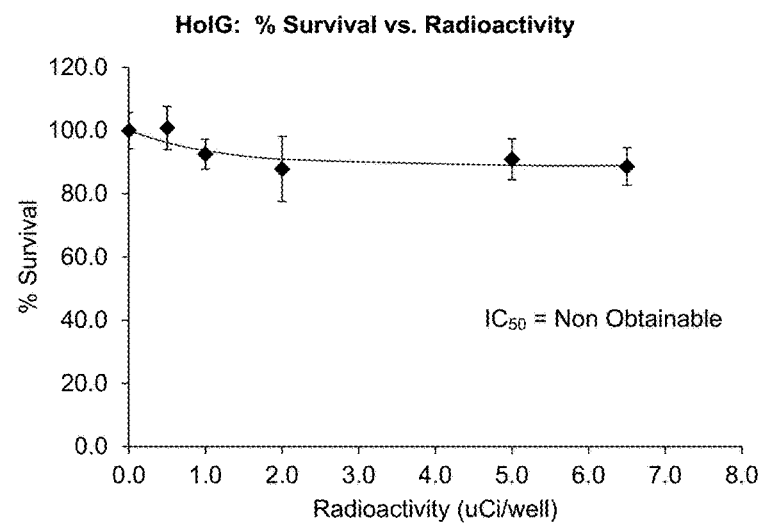
FIGS. 14A-14D. A549 cells treated with HoIG (FIG. 14A), cis-HoIG (FIG. 14B) or cis (FIGS. 14C and 14D) for 24 h at 37° C. in 5% $CO_2$. Each well contained 5,000 cells at t=0, and were treated 24 h later. Nanoparticles were made radioactive prior to treatment via neutron activation. The ratio of [Pt] to radioactivity used in the platinum-containing nanoparticles was ~80 µM/µCi.
Figure 14B:
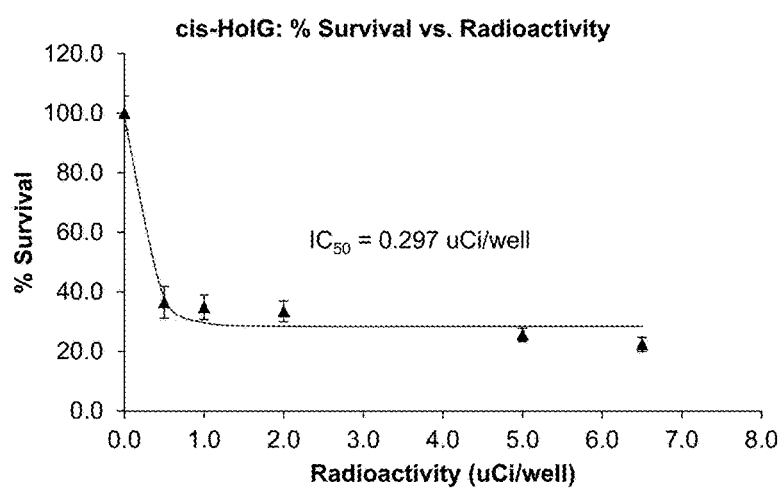
Figure 14C:
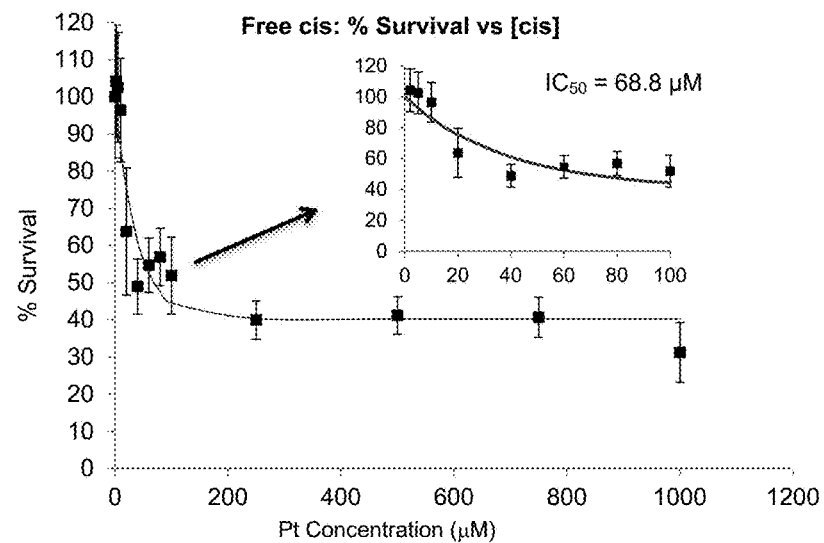
Figure 14D:
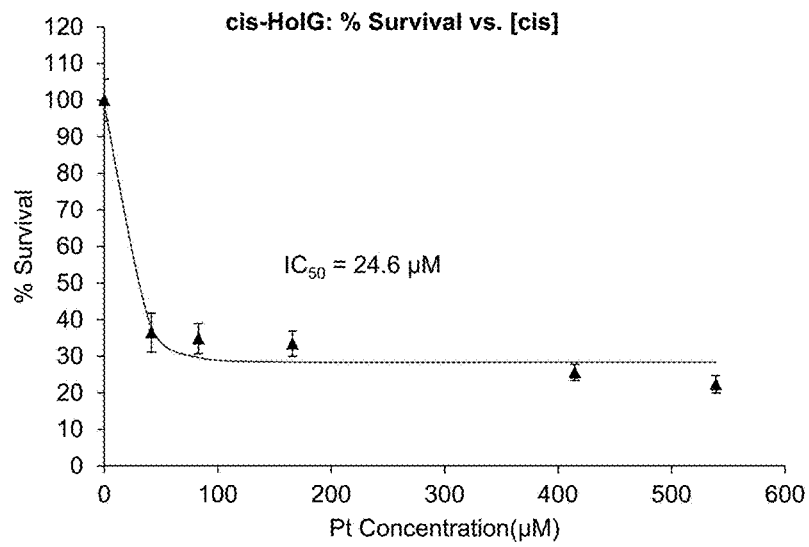
Figure 15A:
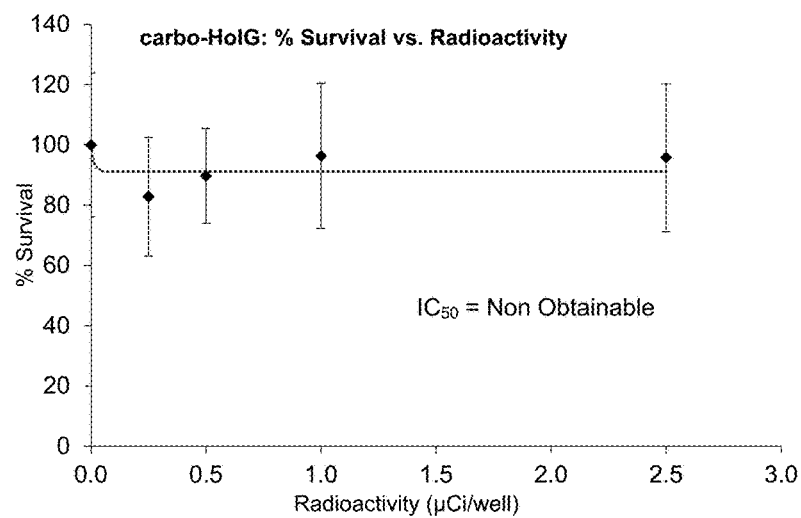
FIGS. 15A-15F. Survival of NSCLC A549 cells treated with carbo-HoIG (FIG. 15A), oxa-HoIG (FIG. 15B), carbo and oxa (FIGS. 15C-15F) for 24 h at 37° C. in 5% $CO_2$. Each well contained 5,000 cells at t=0, and were treated 24 h later. Nanoparticles were made radioactive prior to treatment via neutron activation. The ratio of [Pt] to radioactivity used in the platinum-containing nanoparticles was ~40 µM/µCi.
Figure 15B:
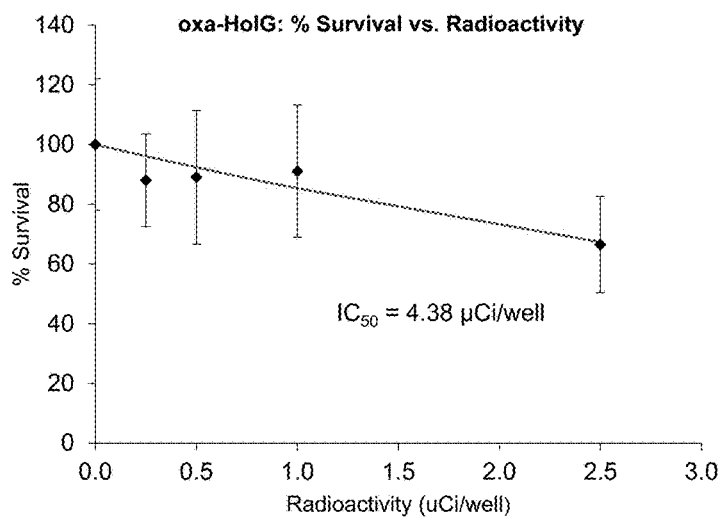
Figure 15C:
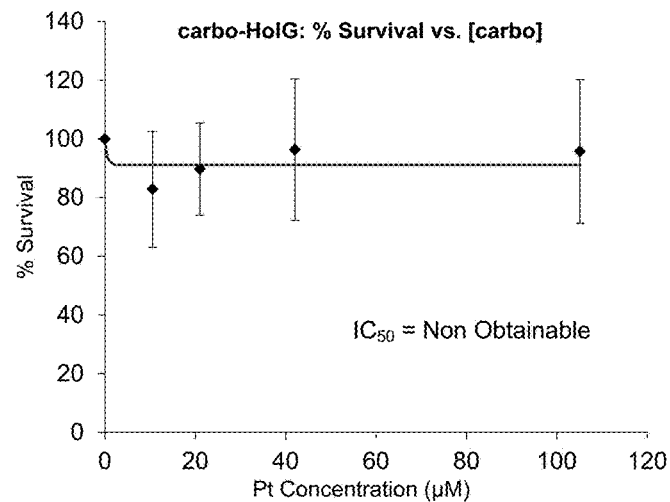
Figure 15D:
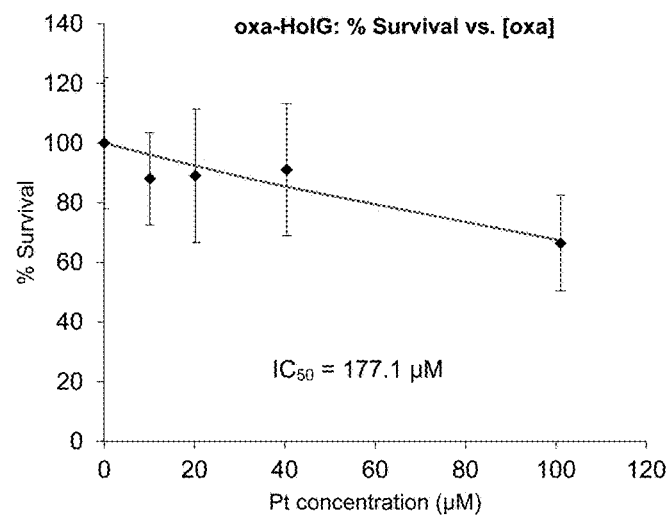
Figure 15E:
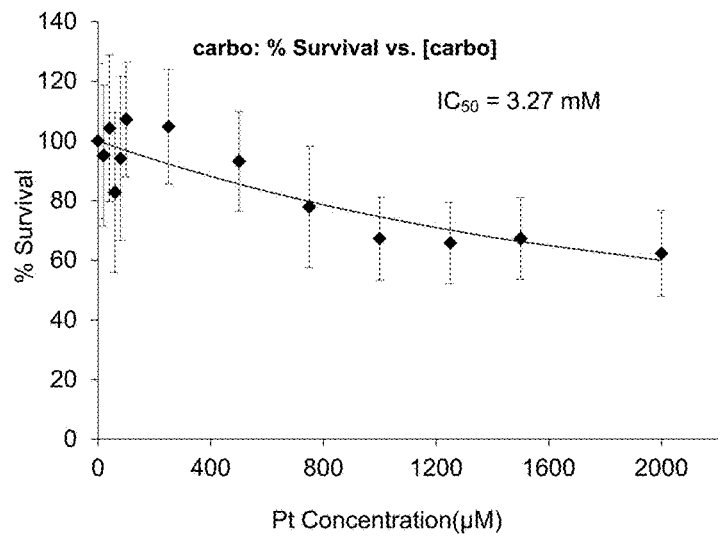
Figure 15F:
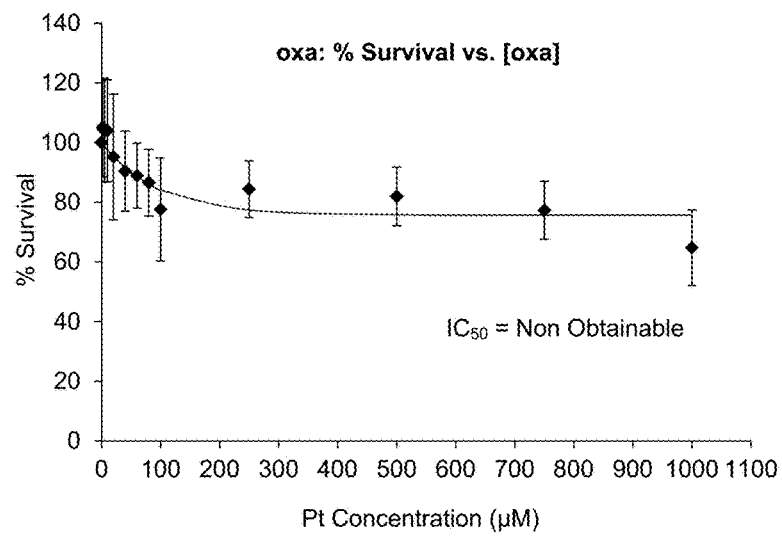

In vitro release of Pt drugs was studied at room temperature in simulated body fluid solution of pH 7.30. FIG. 12 shows the cumulative release of cisplatin and carboplatin with time. DOPC-coated cisplatin/carboplatin drug-loaded HoIG shows slow release as compared to the cisplatin/carboplatin-loaded HoIG nanoparticles. Release profiles are provided in FIG. 13. ICP-MS data was collected before and after modification; before, the nanoparticles contained 33.3% and 8.3% holmium and platinum, respectively, and after modification with DOPC, the nanoparticles contained 13.6% and 3.7% holmium and platinum, respectively.

HoIG with and without platinum complexes (cisplatin (cis); oxaliplatin (oxa); or carboplatin (carbo)) were irradiated in a 1 MW nuclear reactor in a neutron flux of approximately $7.6 \times 10^{12}$ neutrons/$cm^2 \cdot s$. The radioactivity of nanoparticles prior to administration to cells was determined using a 2470 WIZARD 2 automatic gamma counter. Studies involving human NSCLC A549 cells were carried out under standard conditions in a humidified, 37° C., 5% $CO_2$ atmosphere incubator. The culture medium used for A549 cells was minimum essential medium to which had been added 10% fetal calf serum, 100 µg/mL streptomycin, 100 IU/mL penicillin and 2.0 mM L-glutamine. Cells were seeded at $5 \times 10^4$ cells/ml (100 µL/well) in 96-well plates and allowed to grow for 24 h after which time the medium was removed and replaced with medium and drug. After an exposure time of 24 h, the medium with drug was removed and replaced with 100 µL of fresh medium. To each well, 20 µL of CellTiter 96® AQueous One Solution Cell Proliferation Assay (MTS) solution was added. After 2 h incubation with the MTS solution, the absorbance was read at 490 nm using a Synergy™ H1 hybrid multi-mode microplate reader. The percent survival of cells treated by each concentration of drug was calculated using the following equation:

$$\% \text{ survival} = 100 \times \left[\frac{A_d - A_m}{A_c - A_m}\right]$$

where $A_d$ is the absorbance of cells treated with drug, $A_m$ is the absorbance of medium alone and $A_c$ is the absorbance of cells without treatment. The % survival data was fit to exponential regression and $IC_{50}$ values calculated.

After neutron-activation irradiation in a nuclear reactor, cis-HoIG had greater toxicity than HoIG and free cisplatin toward NSCLC A549 cells. Also, oxa-HoIG had greater toxicity than HoIG and oxa toward NSCLC A549 cells. Thus, cis and oxa act synergistically with the radioactive Ho, making nontoxic doses of radiation extremely efficacious and toxic to target cells (see FIGS. 14 and 15).

Example 3—Electrospinning of a Nanofibrous Mat

A $^{165}$Ho-containing polymer nanofibrous mat was prepared via electrospinning using $^{165}$Ho nanoparticles (HoIG) and polyacrylonitrile (PAN). The mat was neutron-activated for 0.5, 1, 2 and 4 h in a thermal neutron flux of approximately $3.5 \times 10^{12}$ n/$cm^2 \cdot s$ in a 1 MW nuclear reactor. In FIG.

16, the bandage can be seen before and after neutron activation for 0.5-4 h; the treated material looks similar in appearance to control (untreated) material after neutron activation (0.5-4 h). Thus, materials can be impregnated with $^{165}$Ho nanoparticles to prepare a "radiotherapeutic bandage" that can withstand the high temperatures associated with neutron activation.

Figure 17:
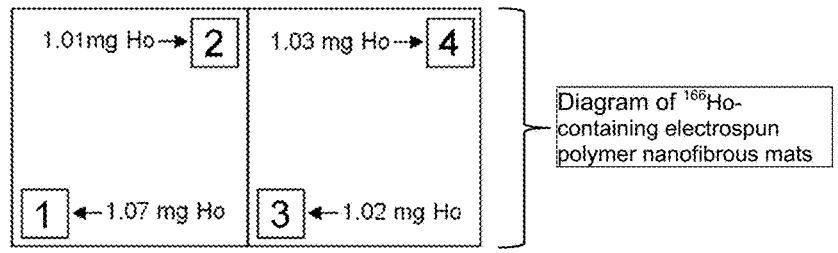
FIG. 17. Diagram showing homogeneity of $^{166}$Ho-containing electrospun polymer nanofibrous mat. The 0.5 h irradiation samples (1-4) obtained from separate locations of the bandage with holmium (Ho) content labeled for each sample.

The radioactivities of the treated samples were also satisfactory and it appears that these materials can withstand greater neutron activation times to achieve even higher radioactivity. For example, after 4 hours of neutron activation, a radioactivity of 650 μCi/mg of mat was produced; each mat was easily cut into small rectangles that were approximately 6 mg in mass. Thus, it is clear that therapeutic levels of radioactivity can easily be reached with $^{165}$Ho nanoparticle-impregnated wound coverings. The electrospun mats were also analyzed to assess the uniformity of radiation emission. Four samples were obtained from different regions of a mat (see FIG. 17, corresponding to those numbered 1-4 in the diagram). After neutron activation for 0.5 h the radioactivity was measured and, from this, $^{166}$Ho content determined. Approximately 1 mg of $^{166}$Ho was contained in each sample, and thus the process can homogeneously distribute $^{165}$Ho nanoparticles throughout the bandage.

Example 4—Synthesis of Holmium Yttrium Iron Garnet (HoYIG) and Dysprosium Yttrium Iron Garnet (DyYIG) Nanoparticles Stoichiometric mixtures (5:1.5:1.5) of 1M nitrates of iron (III) (10 mL), holmium (III) (5 mL), and yttrium (III) (3 mL) were mixed with ethylene glycol (21 mL) at room temperature with stirring. Then 6M NaOH (10 mL) were added dropwise to form the HoYIG precipitate. The product was centrifuged and washed with de-ionized water, then dried at 100° C. overnight. The HoYIG was annealed in air at 900° C. for 3 h. Stoichiometric mixtures (5:1.5:1.5) of 1M nitrates of iron (III) (10 mL), dysprosium (III) (5 mL), and yttrium (III) (3 mL) were used to synthesize DyYIG nanoparticles based on the method described above.

Figure 18A:
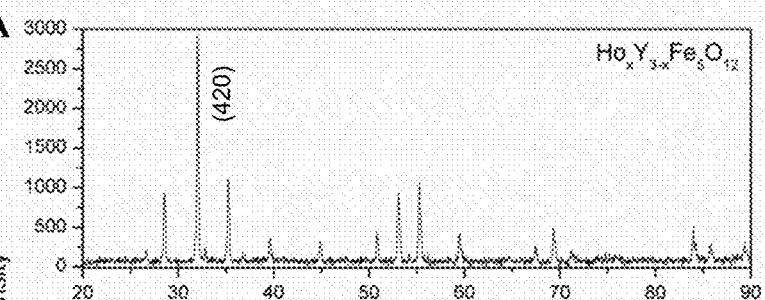
FIGS. 18A-18B. PXRD pattern of (FIG. 18A) HoYIG powder (FIG. 18B) $Y_3Fe_5O_{12}$; JCPDS 00-033-0693.
Figure 18B:
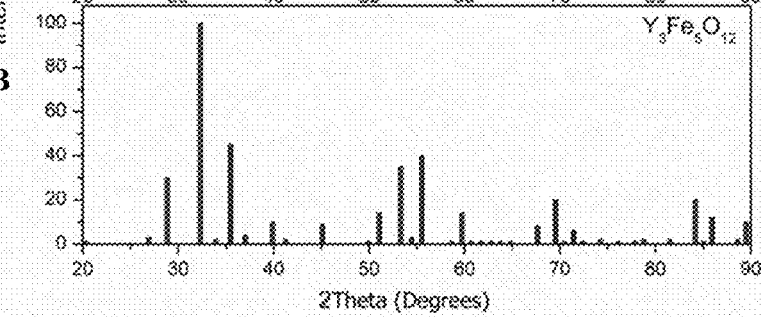

These products were characterized using x-ray diffraction (XRD) on a Rigaku Ultima IV diffractometer using Cu Kα radiation. The average crystallite size of the powders was estimated from corresponding XRD data using Scherrer formula. Scanning electron microscopy (SEM) and energy dispersive X-ray spectroscopy (EDX) analysis was carried out on a Zeiss-LEO model 1530 SEM. The magnetic properties of the garnet nanoparticles and fibers were measured using an MPMS-XL superconducting quantum interference device from Quantum Design. FIG. 18 shows the PXRD pattern of synthesized HoYIG. As compared to YIG the simulated pattern peak positions of HoYIG are mostly similar. The crystallite sizes were calculated from the PXRD line broadening of the peak (420) using the Scherrer equation, $D_{hkl}=k\lambda/B \cos \theta$, where $D_{hkl}$ is the particle size in nm, k is a constant (shape factor) with a value of 0.9, B is the width of half maximum, and $\lambda$ is the wavelength of the x-rays. The $D_{hkl}$ value of HoYIG is about 36 nm.

Figure 19:
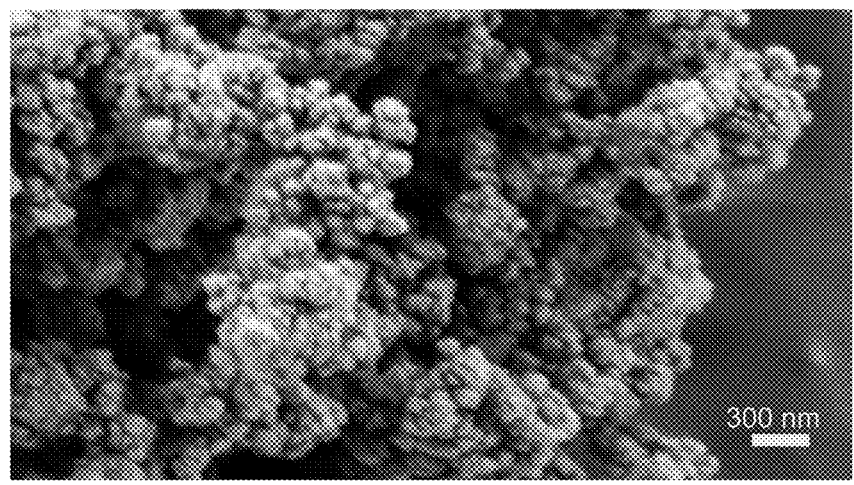
FIG. 19. SEM images of synthesized HoYIG.
Figure 20:
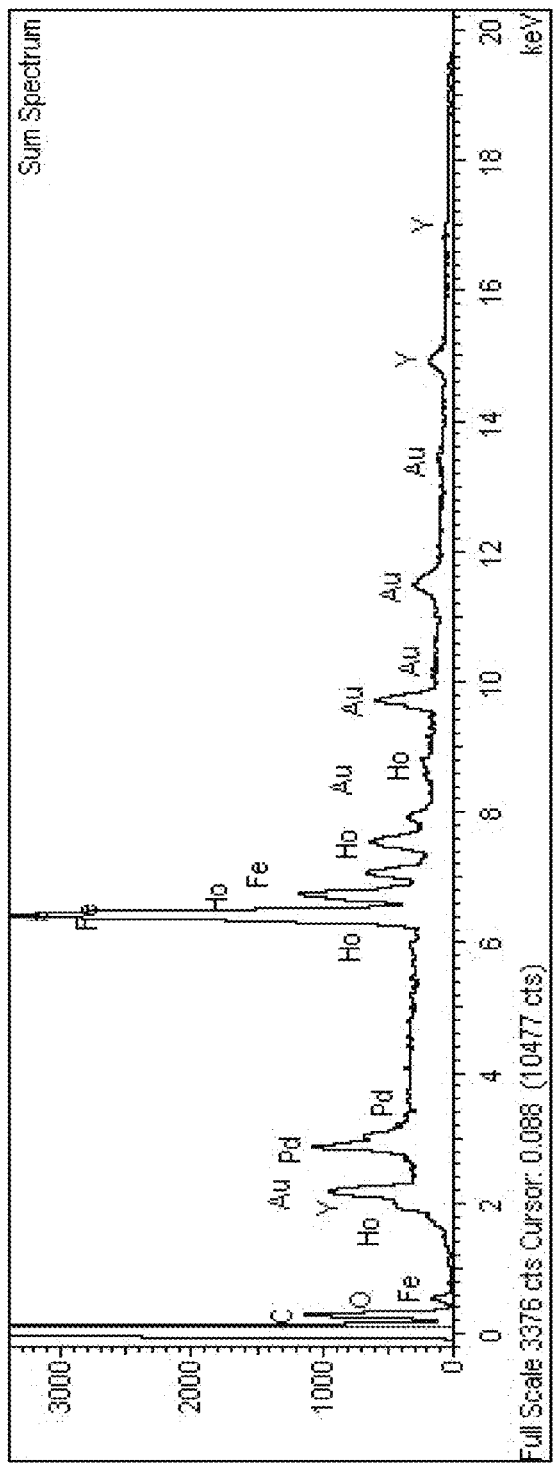
FIG. 20. The EDS sum spectrum of Au/Pd coated HoYIG. Based on the EDS results the synthesized HoYIG consists of 15.94% Fe, 4.72% Ho, 78.39% 0, and 0.95% Y. Therefore the formulation of the synthesized HoYIG is $Ho_{2.6}Y_{0.4}Fe_5O_{12}$.

FIG. 19 shows the SEM image of synthesized HoYIG nanoparticles. The particles have nearly a uniform size distribution and also contained some agglomeration and FIG. 20 shows the EDS sum spectrum of Au/Pd-coated HoYIG. Based on the EDS results the synthesized HoYIG consists of 15.94% Fe, 4.72% Ho, 78.39% 0, and 0.95% Y. Therefore the formulation of the synthesized HoYIG is $Ho_{2.6}Y_{0.4}Fe_5O_{12}$.

Figure 21:
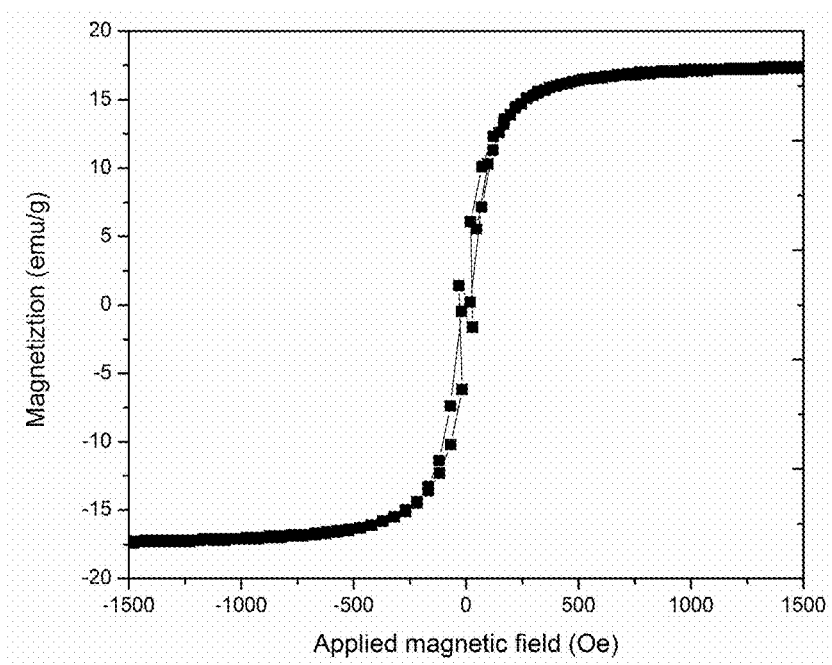
FIG. 21. Magnetic hysteresis loops of the synthesized HoYIG at room temperature.

The magnetization of the synthesized HoYIG powder was performed at room temperature. Plots of magnetization (M) (normalized to the mass of magnetic material) as a function of magnetic field (H) are shown in FIG. 21. The saturation magnetization (Ms) is defined as the state when an increase in the magnetic field cannot increase the magnetization of the material further and Ms for HoYIG nanoparticles reached 17.5 emu/g.

Figure 22A:
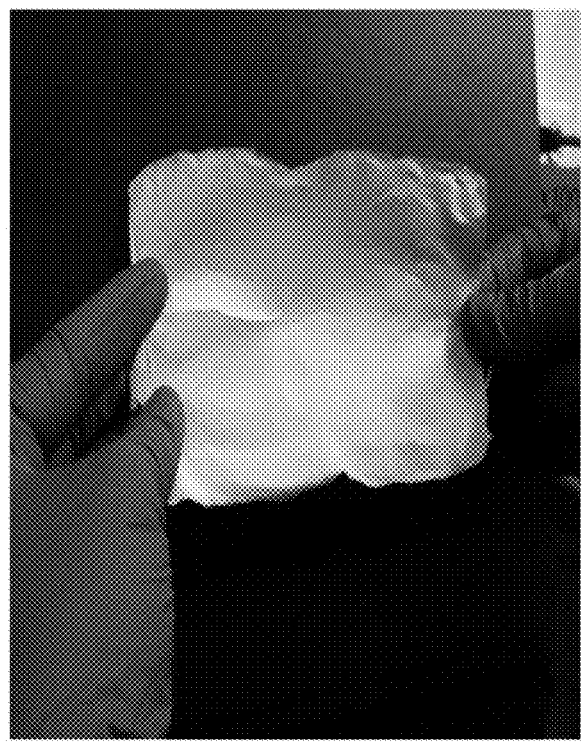
FIGS. 22A-22B. Digital image of (FIG. 22A) 10% PAN/ 5% HoYIG electrospun bandage (FIG. 22B) electrospun bandage pickup by a magnet.
Figure 22B:
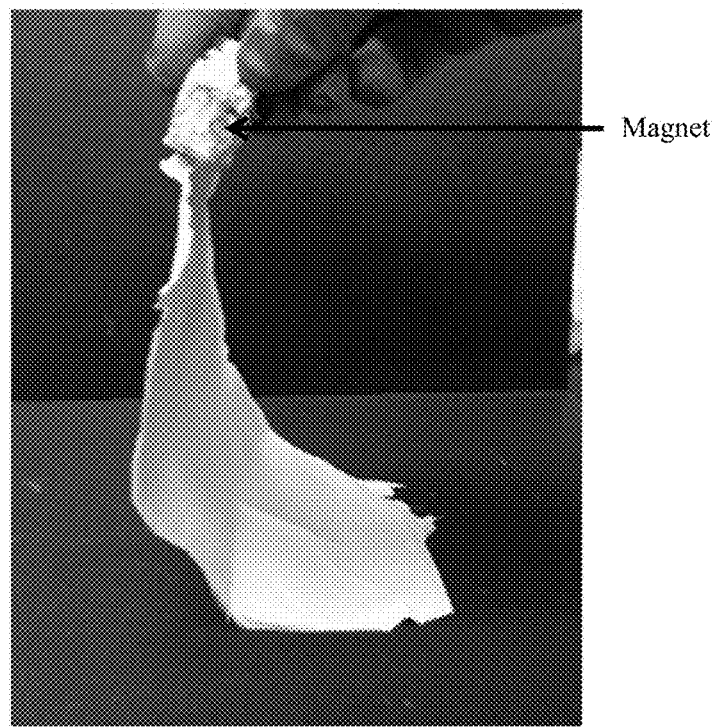

Example 5—Electrospinning of Polymer Solutions with HoYIG and DyYIG Nanoparticles Acrylonitrile (AN)-based polymers can be made into non-woven fiber mats by use of electrospinning. HoYIG nanoparticles were dispersed in dimethylformamide (DMF) at room temperature. Polyacrylonitrile (PAN) was dissolved in 8 mL of DMF. Two solutions were mixed together for electrospinning. A solution with nanoparticles in the range of 5-20% weight/volume was prepared. The solution was then loaded into a syringe with a spinneret needle gauge of 18 to 22. A voltage in the range of 8-20 kV (e.g., 13 kV) is applied to the spinneret. The fibers were collected on a rotating drum. As illustrated in FIG. 22, the bandage is flexible and magnetic (the electrospun bandages can be picked up by a magnet).

Figure 23A:
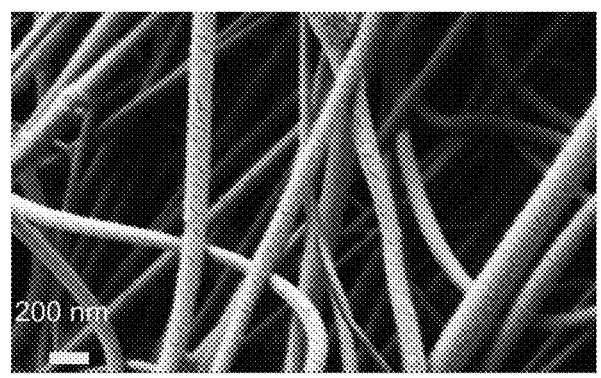
FIGS. 23A-23B and 24A-24B. SEM images (FIGS. 23A and 23B) and fiber diameter distributions of 5% HoYIG loaded.
Figure 23B:
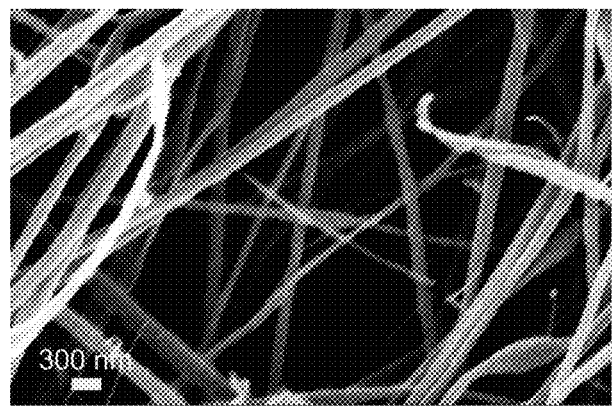
Figure 24A:
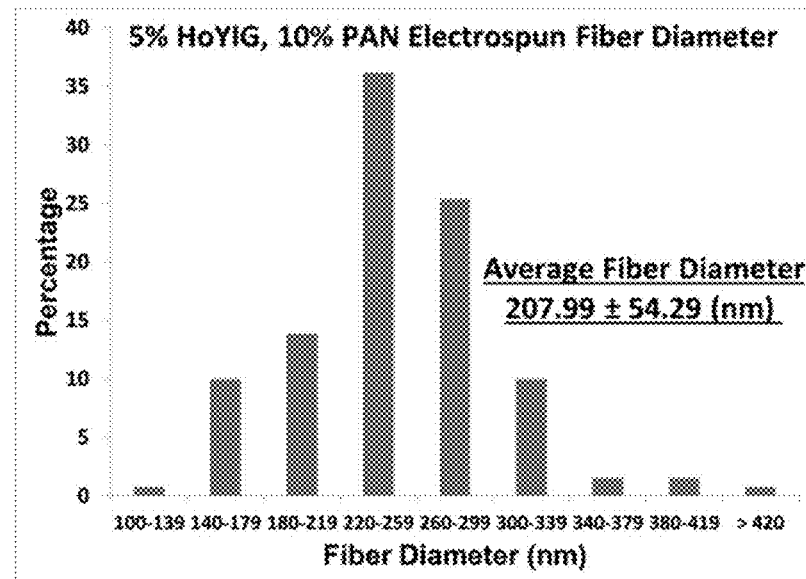
Figure 24B:
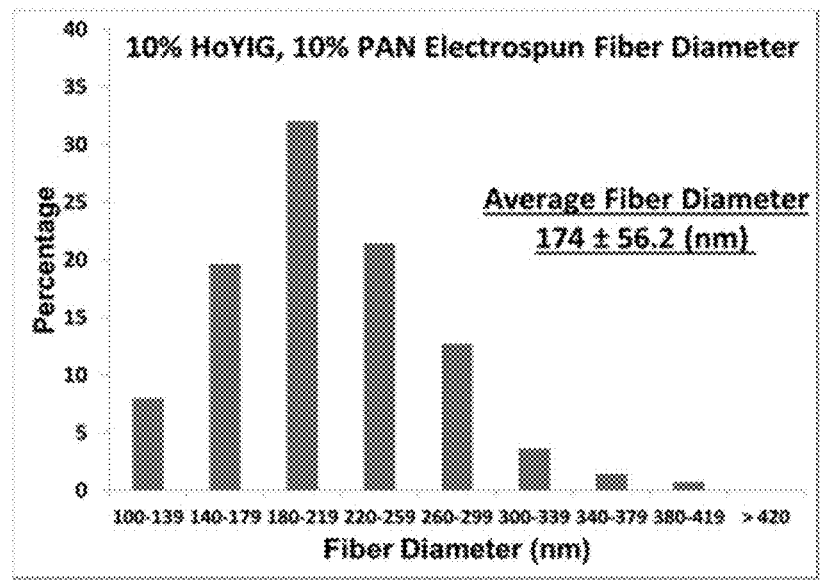
Figure 25A:
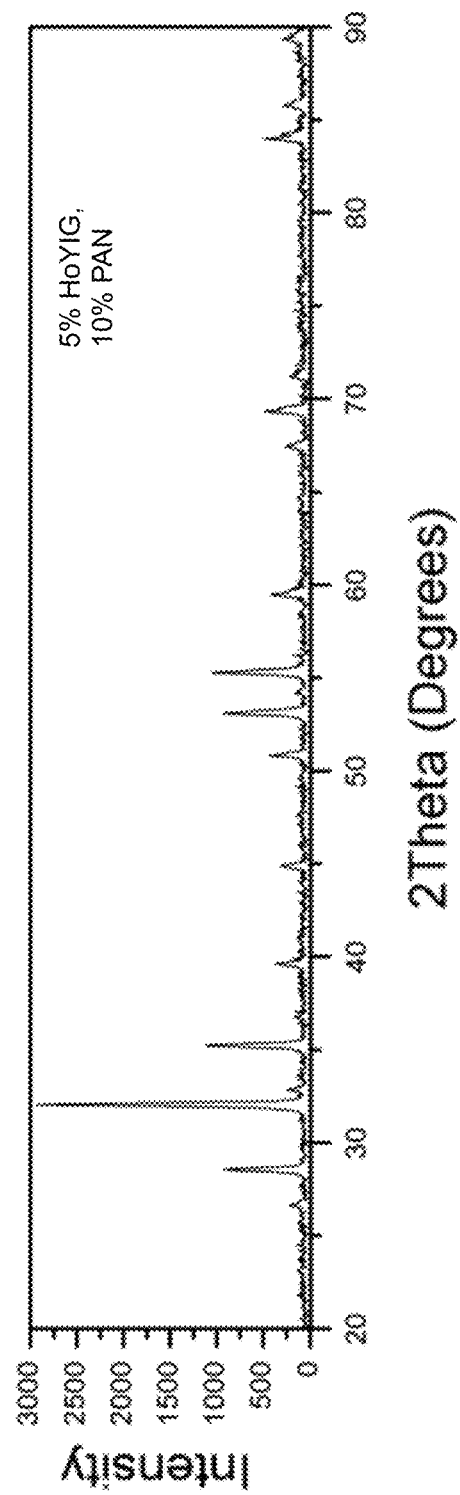
FIGS. 25A-25C. PXRD pattern of (FIG. 25A) HoYIG powder, (FIG. 25B) 10% PAN/5% HoYIG electrospun fiber, and (FIG. 25C) $Y_3Fe_5O_{12}$; JCPDS 00-033-0693.
Figure 25B:
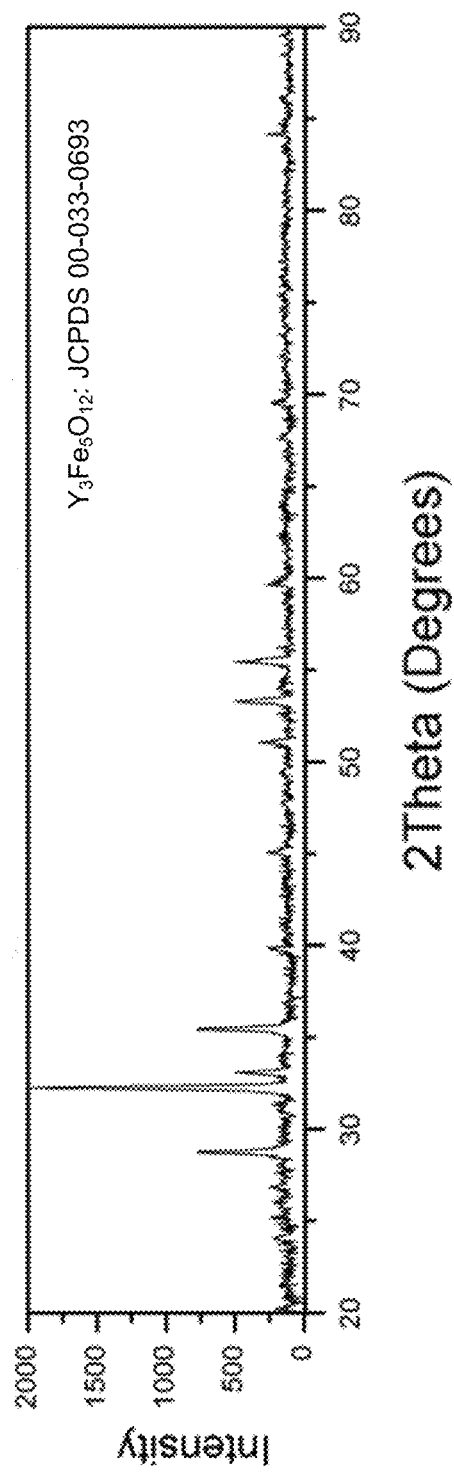
Figure 25C:
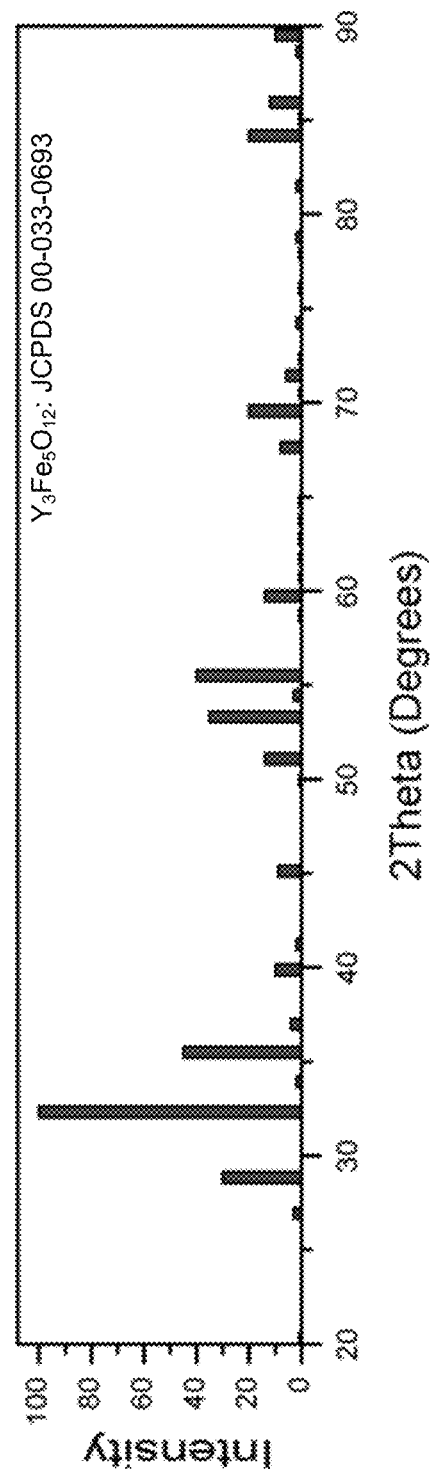
Figure 26:
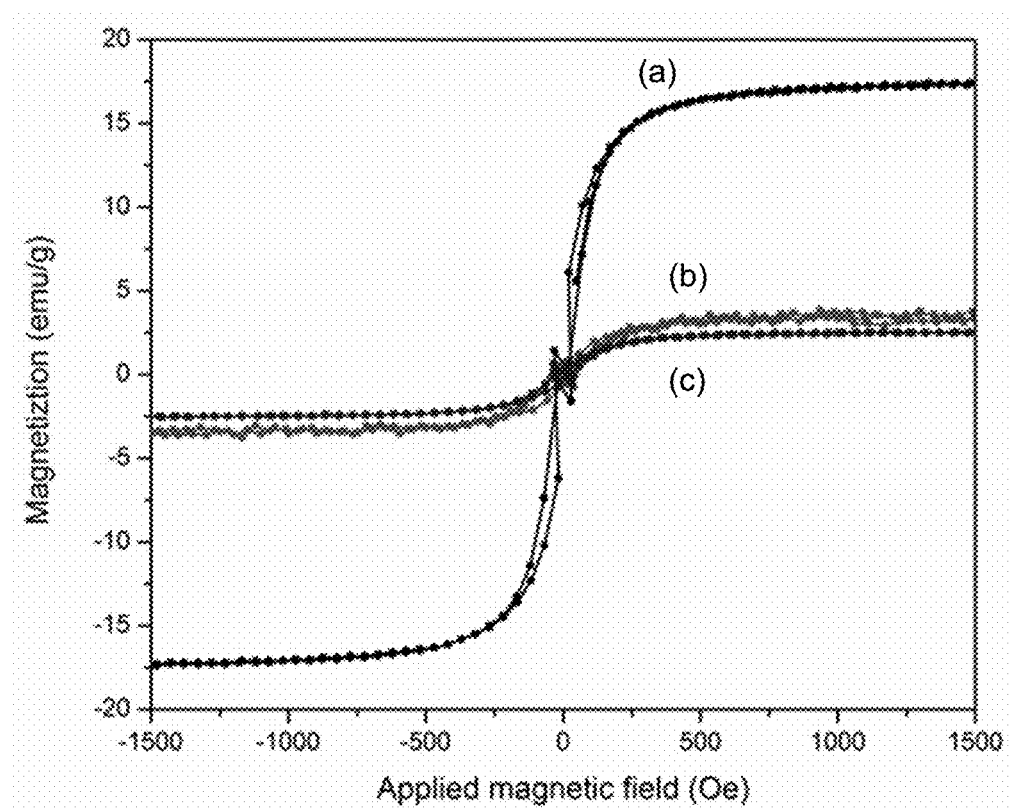
FIG. 26. The room temperature magnetic hysteresis loops of the electrospun bandages. Magnetization values have been normalized to the mass of magnetic material. The saturation magnetization ($M_s$) increases as the loading of HoYIG nanoparticle increases. The $M_s$ values are 2.5 and 3 emu/g for 5% and 10% HoYIG loaded electrospun bandages respectively (FIG. 7). The noticeably lower values in the saturation magnetization relative to the bulk powder could be ascribed to the low concentration of the garnet magnetic material inside the fibers.

SEM images of the electrospun fiber mats with different HoYIG nanoparticle loadings are shown in FIGS. 23A and B. As shown in the histogram the average diameter of nanofibers with standard error values is 208±54 nm and 174±56 nm when the HoYIG loadings are 5% and 10% (FIGS. 24A and B). The XRD patterns of the electrospun fibers with 5% loading of HoYIG nanoparticles are shown in FIG. 25 and confirm the presence of HoYIG nanoparticles in nanofibers. FIG. 26 shows the room temperature magnetic hysteresis loops of the electrospun bandages. Magnetization values have been normalized to the mass of magnetic material. The saturation magnetization ($M_s$) increases as the loading of HoYIG nanoparticles increases. The $M_s$ values are 2.5 and 3 emu/g for 5% and 10% HoYIG-loaded electrospun bandages, respectively. The noticeably lower values in the saturation magnetization relative to the bulk powder could be ascribed to the low concentration of the garnet magnetic material inside the fibers.

Example 6

Experimental Section

Chemicals.

Holmium (III) nitrate hexahydrate, sodium hydroxide, ethylene glycol, cisplatin, carboplatin, oxaliplatin were purchased from the Aldrich Chemical Co. Iron (III) nitrate hexahydrate was purchased from Acros Organics. All reagents were used as received.

Synthesis of Holmium Iron Garnet Nanoparticles (HoIG).

HoIG was synthesized by modifying a reported procedure (Munaweera et al., 2014). Stoichiometric mixtures (5:3) of 1 M nitrates of iron (III) (5 mL) and holmium (III) (3 mL) were mixed with ethylene glycol (21 mL) at room temperature with stirring. Then, 6 M NaOH (10 mL) was added dropwise to form the HoIG precipitate. The product was centrifuged and washed with de-ionized water, then dried at 100° C. overnight. The HoIG was annealed in air at 900° C. for 3 h.

Platinum Drug-Loaded HoIG Nanoparticles (HoIG-Pt).

HoIG-Pt, i.e., cisplatin, carboplatin and oxaliplatin-loaded HoIG (HoIG-cisplatin, HoIG-carboplatin and HoIG-oxaliplatin), were prepared using the same manner as described for HoIG. Then, to a solution containing one of the platinum drugs (5 mg) in water (10 mL) was added HoIG (30 mg), and the mixture was sonicated for 3 h. The Pt drug-loaded nanoparticles were then collected by centrifugation. The amount of remaining platinum drug in the solution was analyzed using ultraviolet-visible spectrophotometry (UV/Vis, Shimadzu UV-1601PC), and the amount of drug loaded calculated. The product was then dried at 80° C. for 8 h. The dry HoIG-Pt was then digested in nitric acid at 70° C. for 48 h and Pt content analyzed using inductively coupled plasma-mass spectrometry (ICP-MS, NexION 300D from PerkinElmer).

Study of In Vitro Release of Platinum Drugs from HoIG-Pt.

HoIG-Pt (30 mg) was dispersed in simulated body fluid (SBF, pH 7.3) (50 mL) and kept at 37° C. with stirring at 600 rpm. An aliquot (3 mL) was withdrawn after centrifugation of the suspension at each specified time period and was replaced with an equal volume of fresh SBF. The concentrations of the released Pt drugs were measured using a UV/Vis spectrometer.

Neutron Activation of HoIG, HoIG-Pt.

Dry $^{166}$HoIG and $^{166}$HoIG-Pt were neutron-activated in a 1 MW TRIGA Mark I nuclear reactor at the Texas A&M Nuclear Science Center in a thermal neutron flux of approximately $7 \times 10^{12}$ neutrons/cm$^2 \cdot$s for ≥0.2 h. Gamma radioactivity was measured before shipment to UNTHSC and again directly prior to performing cell studies using a calibrated WIZARD2 Automatic Gamma Counter (PerkinElmer).

Cytotoxicity Studies.

The studies involving human NSCLC A549 cells were carried out under standard conditions in a humidified, 37° C., 5% CO$_2$ atmosphere incubator. The culture medium used for A549 was Roswell Park Memorial Institute with 10% fetal calf serum (FCS), 100 µg/mL streptomycin, 100 IU/mL penicillin and 2.0 mM L-glutamine (RPMI).

Suspensions of each type of neutron-activated nanoparticle were prepared in RPMI. Two control groups, RPMI alone and RPMI with cells not exposed to $^{166}$Ho nanoparticles, were included in each 96-well plate. At least four replicates were done for each concentration and each control group. The cells were seeded at $5 \times 10^4$ cells/mL (100 µL/well) in 96-well plates and allowed to grow for 24 h after which time the RPMI was removed and replaced with 100 µL of RPMI that contained blank $^{166}$HoIG or $^{166}$HoIG-Pt. After an exposure time of 24 h on a microplate shaker in the incubator, the RPMI was removed and replaced with 100 µL of fresh RPMI. To each well, 20 µL of CellTiter 96® AQueous One Solution Cell Proliferation (MTS) assay solution was added. After 1 h incubation with the MTS solution, the absorbance was read at 490 nm using a Synergy™ H1 hybrid multi-mode microplate reader. The percent survival of cells treated by each concentration of nanoparticles was calculated using the following equation:

$$\% \text{ survival} = 100 \times \left[\frac{A_d - A_m}{A_c - A_m}\right] \quad (1)$$

where $A_d$ is the absorbance of cells treated with nanoparticles, $A_m$ is the absorbance of medium alone and $A_c$ is the absorbance of cells without treatment. The % survival data was fit to exponential regressions using Excel Solver, and IC$_{50}$ values calculated.

Cytotoxicity studies involving free cisplatin, carboplatin and oxaliplatin were done in the same manner. The only difference was that the microplate shaker was not used, as all three drugs can be dissolved in RPMI.

Animal Studies

Cells and Animals.

A549 human lung adenocarcinoma cells were obtained from the American Type Culture Collection (ATCC). Female T cell-deficient athymic nude mice were obtained from Harlan Laboratories. All animal procedures were performed following a protocol approved by the University of North Texas Health Science Center Institutional Animal Care and Use Committee in accordance with the NIH Guidelines.

Subcutaneous A549 Xenograft Model.

A549 human lung adenocarcinoma cells ($5 \times 10^6$) resuspended in a total volume of 100 µL of PBS and Matrigel (1:1) were injected into the flank of the left hind leg of each mouse. Tumor volumes were monitored twice a week by measuring two perpendicular diameters with calipers. Tumor volume (V) was calculated using the following equation:

$$V = (L \times W^2)/2 \quad (2)$$

where L is the length (large diameter), and W is the width of the tumor (small diameter), both in millimeters. Each magnet used in this study was 2.5 g and 12,000 Gauss; it was placed on the top of the tumor and kept in place using Nexcare Steri-strip skin adhesive surgical tape strips. HoIG-cisplatin and $^{166}$HoIG-cisplatin suspensions were prepared using phosphate-buffered saline (PBS) containing 10% of polyethylene glycol 1500 (PEG 1500). The dose of cisplatin incorporated in HoIG or $^{166}$HoIG, which was injected into each mouse, was 5 mg/kg.

Ratio of Percent Weight Metal in Tumor to Liver after i.v. Injection of HoIG-Cisplatin.

Five million A549 cells were injected subcutaneously into the flank of the left hind leg of each mouse and when tumor size was approximately 50 mm$^3$, mice were randomized into two groups (n=4 each). To the first group, a magnet was taped on the top of the tumor as described earlier and 100 µL of HoIG-cisplatin suspension was injected via tail vein; mice were exposed to magnets during and 5 h after injection of HoIG-cisplatin. The second group received the same injection at the same time without an attached magnet. Both groups were sacrificed immediately after the 5 h duration and tumors and livers harvested and digested using 70% nitric acid at 70° C. The Pt and Ho contents in tumor and liver samples were characterized using ICP-MS.

Efficacy Study.

To female athymic nude mice, 5 million A549 cells were injected subcutaneously into the flank of the left hind leg of each and when tumor size was approximately 50-100 mm$^3$, mice were randomized into groups (n≥6 per group each). Magnets were applied to Groups 1-3 but not Group 4. To Groups 1 and 2, a magnet was taped on top of the tumor and injected with 100 µL of radioactive $^{166}$HoIG-cisplatin (Group 1) or HoIG-cisplatin (Group 2) suspension through the tail vein; mice were exposed to magnets during and 5 h after injection. To Group 3, a magnet was taped in the same manner but without nanoparticle injection; mice were exposed to magnets for 5 h. Group 4 was a control group without magnet or injection. Tumor growth was monitored once every five days for up to 35 days.

Nanoparticle Characterization.

The x-ray diffraction patterns were collected on a Rigaku Ultima IV x-ray diffractometer using Cu Kα radiation. The morphology of the synthesized HoIG was analyzed using transmission electron microscopy (TEM). TEM analysis was performed on a JEOL 2100 analytical TEM with an accelerating voltage of 200 kV. EDX analyses of carbon-coated samples were carried out using a Zeiss-LEO model 1530 SEM. The magnetic properties of the nanoparticles was measured using a superconducting quantum interference device (MPMS-XL from Quantum Design), and the saturation magnetization ($M_s$), remnance ($M_r$) and coercivity ($H_c$) were determined from the hysteresis loops. Magnetic susceptibility ($\chi_m$) and relative permeability ($\mu_r$) were calculated from the linear slope of the M(H) curve. The zetapotential measurements of nanoparticles were determined using a Malvern Zetasizer Nano ZS.

Results and Discussion

Holmium Iron Garnet Nanoparticles (HoIG).

Figure 27A:
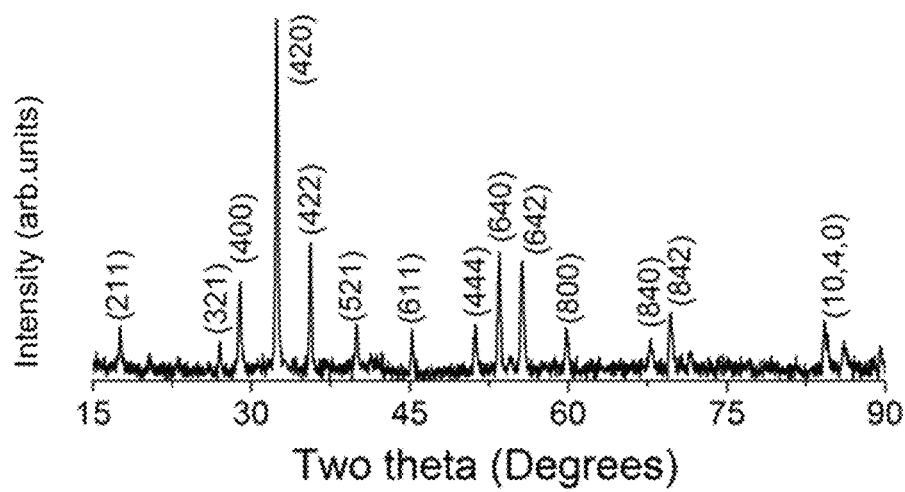
FIGS. 27A-27B. PXRD pattern of (A) HoIG powder (B) $Fe_5Ho_3O_{12}$; JCPDS 00-023-0282.
Figure 27B:
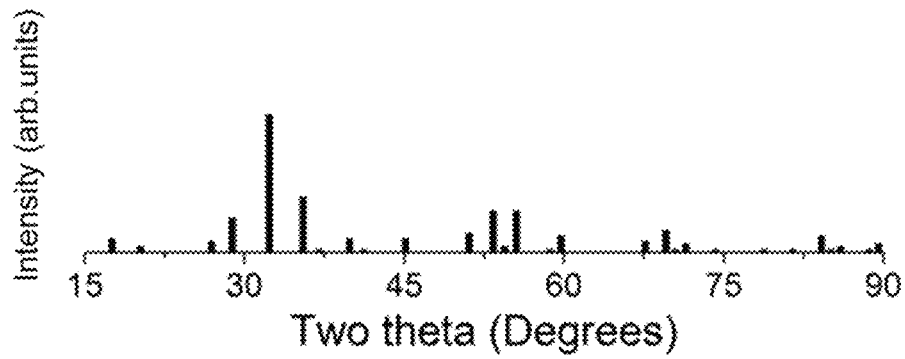

HoIG was synthesized using a hydroxide co-precipitation method. FIGS. 27A and 27B show the PXRD pattern for the as-synthesized HoIG samples. The phase matches well with $Fe_5Ho_3O_{12}$ (JCPDS 00-023-0282). The crystal size was calculated from the PXRD line broadening of the (420) peak using the Scherrer equation, $D_{hkl}=k\lambda/B \cos\theta$, where $D_{hkl}$ is the particle size in nm, k is a constant (shape factor) with a value of 0.9, B is the width of half maximum, and $\lambda$ is the wavelength of the x-rays. The $D_{hkl}$ value of HoIG was approximately 52 nm.

The TEM image of synthesized HoIG (FIG. 28A) exhibits a rounded irregular shape. The average size of the nanoparticles is 40.7±16.4 nm in length and 26.9±8.0 nm in width. The interplanar distance of HoIG in FIG. 28B is 0.28 nm, which corresponds to the (420) plane d=0.27670 nm in FIGS. 27A and 27B. These results indicate that nanocrystalline HoIG powder was successfully prepared by the hydroxide co-precipitation method. The synthesized HoIG is olive green in color and shows magnetic properties. The magnetization of the synthesized HoIG powder was performed at room temperature. The plot of magnetization (M) (normalized to the mass of magnetic material) as a function of magnetic field (H) is shown in FIG. 29.

The saturation magnetization ($M_s$) is defined as the state at which an increase in the magnetic field does not lead to further increase in the magnetization of the material. $M_s$ reached 8.9 emu/g with the average particle size of 50 nm. The coercive field ($H_c$, the external magnetic field required to bring the magnetization to zero) was 50 Oe. The reported saturation magnetization of YIG particles with an average 25 nm size was 20.6 emu/g and the coercivity is 51 Oe (Rajendran et al., 2006). The principal magnetic interaction in HoIG is the superexchange in the $(Fe^{3+})_A—O^{2-}—(Fe^{3+})_D$ triads. This interaction forms two antiparallel iron sublattices with the easy axis along the (111) direction. The rare earth moments are antiparallel to the iron spins owing to the (C-D) exchange interaction (Lataifeh et al., 2000). In the case of YIG there is no magnetic contribution from $Y^{3+}$ due to the closed shell yttrium ions. But there is a magnetic contribution from $Ho^{3+}$ ions antiparallel to the iron spin in HoIG which results in low saturate magnetization for HoIG as compared to the YIG nanoparticles. The remnant magnetization ($M_r$) was 2.8 emu/g for HoIG. The calculated magnetic susceptibility ($\chi_m$) using the linear part of the magnetization slope (Nguyet et al., 2013) was 2.08 and relative permeability ($\mu_r=1+\chi_m$) was 3.08. These results are consistent with the room temperature soft ferromagnetic behavior of these materials (Rajendran et al., 2006).

Platinum Drug-Loaded HoIG Nanoparticles (HoIG-Pt).

Figure 30:
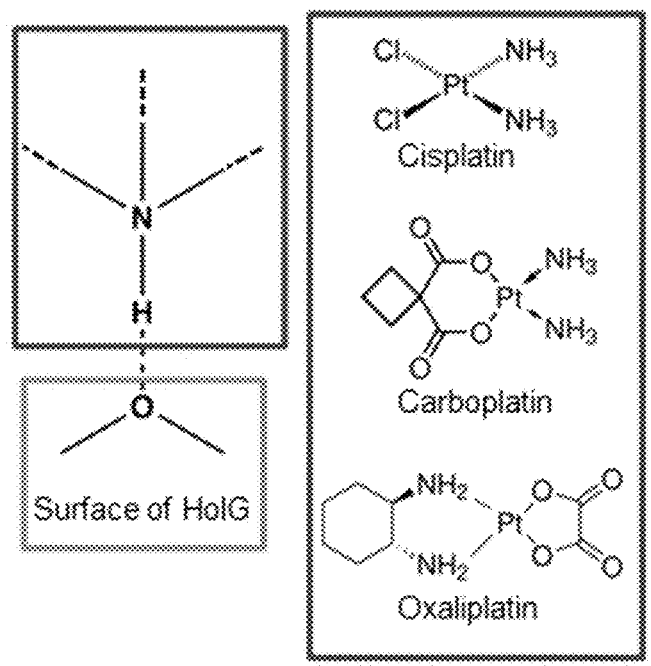
FIG. 30. The platinum drugs and possible ligand interaction with the HoIG.

The FTIR spectrum showed the successful loading of platinum drugs onto HoIG. The ATR-FTIR spectrum of cisplatin showed the characteristic amine stretching in the range of 3400-3200 $cm^{-1}$, the asymmetric amine bending in the range of 1600-1500 $cm^{-1}$ and the symmetric amine bending in the range of 1300-1200 $cm^{-1}$ (Yan et al., 2005). The characteristic asymmetric amine stretching in the range of 3145-3268 $cm^{-1}$ of carboplatin was also observed (Wysoninski et al., 2006) as was the characteristic asymmetric amine stretching band in the range of 3346-3460 $cm^{-1}$, the degenerate deformation vibration of amino group at 1610 $cm^1$ and wagging mode of the amino group at 1609 and 1620 $cm^{-1}$ for oxaliplatin (Tyagi et al., 2008). It has been reported that when the oxide materials are dehydroxylated by increasing the temperature, there is an increase in ammonia hydrogen bonding to the oxygen atoms of the material (Pugh et al., 1994). Therefore, annealed HoIG at high temperature shows no characteristic hydroxyl stretching in the FTIR. Thus, the surface of HoIG is dehydroxylated and there is a tendency for binding of amine groups of platinum drugs to the oxygen atoms of the HoIG through hydrogen bonding. The red shift of the characteristic amine stretching and bending bands of cisplatin, carboplatin and oxaliplatin are ascribed to the hydrogen bonding of platinum drug molecules with surface oxide groups of the HoIG (FIG. 30). Energy-dispersive x-ray spectroscopy (EDX) further confirmed the presence of the platinum drugs on HoIG.

The weight percent of Ho and Pt, determined using ICP-MS, are shown in Table 6.

TABLE 6

Weight percentage of Ho and Pt in HoIG and HoIG-Pt derivatives

| Sample | Wt % Pt | Wt % Ho |
| --- | --- | --- |
| HoIG | — | 55.6 |
| HoIG-cisplatin[1] | 6.2 | 47.1 |
| HoIG-carboplatin | 3.2 | 51.2 |
| HoIG-oxaliplatin | 2.2 | 52.9 |

[1]HoIG-cisplatin Pt ± 3.5 and Ho ± 6.1.

Figure 31:
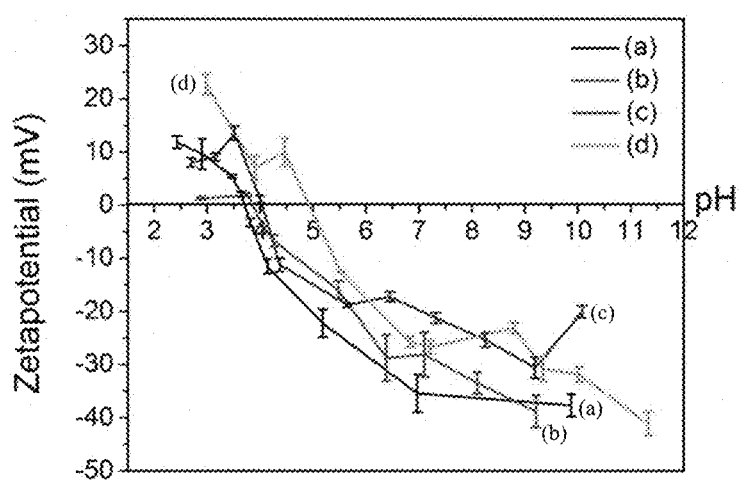
FIG. 31. Zetapotential measurements of (a) HoIG, (b) HoIG-cisplatin, (c) HoIG-carboplatin and (d) HoIG-oxaliplatin.

The stability of HoIG-Pt at different pH values is shown in FIG. 31. The isoelectric point of HoIG is 3.7, and the isoelectric points of cisplatin, carboplatin and oxaliplatin-loaded HoIG are 3.9, 4.0 and 4.9, respectively. When the pH value of the solution is less than the isoelectronic point, the HoIG and HoIG-Pt are positively charged, and they are negatively charged when the pH is above the isoelectronic point. The zeta potential of HoIG in neutral aqueous media was determined to be −35.4 mV. This negative potential is due to the negatively charged oxide surface of HoIG. However the zeta potential of platinum drug-loaded HoIG was higher than that of HoIG. The zeta potentials of HoIG-cisplatin, HoIG-carboplatin and HoIG-oxaliplatin were −28.1, −20.2 and −26.7, respectively. This may reflect a decrease in negative surface charge of HoIG after the platinum drug was conjugated with the HoIG. It has been reported that cisplatin-loaded poly(acrylic acid-co-methyl methacrylate) (p(AA-MMA)) microparticles are less electronegative (~−40 mV) than the blank (p(AA-MMA)) microparticles (~−42 mV) (Yan et al., 2005a). Cisplatin-conjugated calcium phosphate nanoparticles (CaPNPs) are also less electronegative (−27.9 mV) than blank CaPNPs (−45.59 mV) (Cheng et al., 2007). Cisplatin-, carboplatin- and oxaliplatin-loaded HoIG are approximately −30 mV, −23 mV and −26 mV, respectively, at pH 7.35-7.45, which is a predictor for stability in the blood. It has been reported that superparamagnetic nanoparticles showed a zeta potential of −18.3 mV at physiological pH 7.2, and had a high stability in vitro (Sun et al., 2009).

In Vitro Release of Platinum Drugs from HoIG-Pt.

Figure 32:
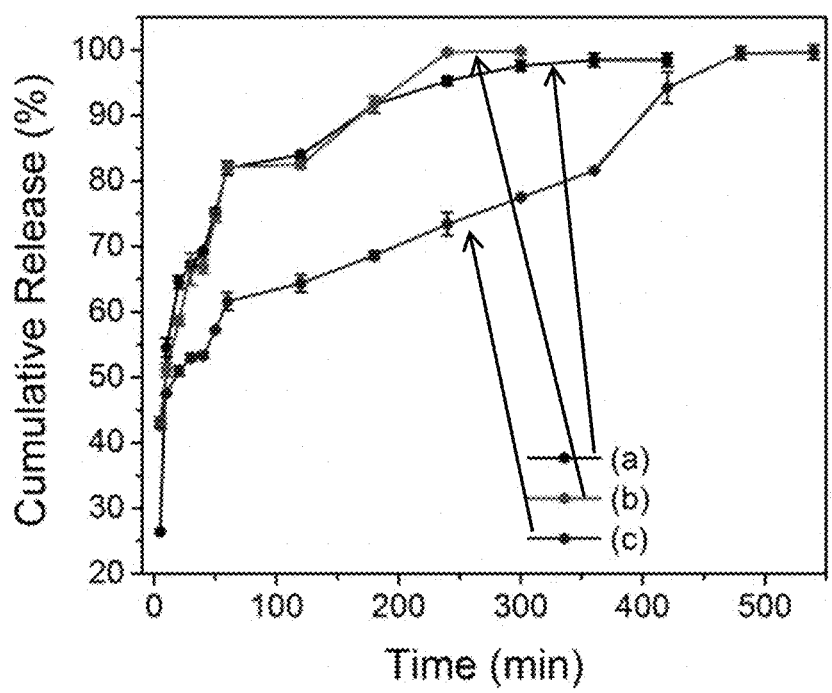
FIG. 32. In vitro release kinetics of encapsulated Pt(IV) compounds (a) HoIG-cisplatin, (b) HoIG-carboplatin and (c) HoIG-oxaliplatin in SBF (pH 7.3).

The amount of Pt released from the nanoparticles over time was measured by UV/Vis spectroscopy. The controlled release of platinum drugs from the nanoparticles is shown in FIGS. 32A-32C. 80% of cisplatin and carboplatin and 60% of oxaliplatin were released after 1 h (FIGS. 32A-32C). Thereafter, a period of controlled platinum release occurred, reaching a value of 99% after 400, 250 and 500 min for HoIG-cisplatin, HoIG-carboplatin and HoIG-oxaliplatin, respectively.

To further analyze the in vitro release data, various kinetic models were used to describe the release kinetics. The zero order rate describes the systems where the drug release rate is independent of its concentration. A first order describes the release from the system where the release rate is concentration-dependent. Higuchi describes the release of drugs from an insoluble matrix as a square root of time-dependent process based on Fickian diffusion. The Hixson-Crowell cube root law describes the release from systems where there is a change in surface area and diameter of particles or tablets (Munaweera et al., 2004a; Dash et al., 2010).

The linear plots of cumulative % drug release vs. time (zero order kinetic model), log cumulative of % drug remaining vs. time (first order kinetic model), cumulative % drug release vs. square root of time (Higuchi model), log cumulative % drug release vs. log time (Korsmeyer-Peppas model), and cube root of drug % remaining in matrix vs. time (Hixson-Crowell model) (Munaweera et al., 2014a) were plotted and compared.

TABLE 7

$R^2$ values of linear plots of different kinetic models for drug release from Pt-HoIG

| Kinetic model | HoIG-cisplatin | HoIG-carboplatin | HoIG-oxaliplatin |
| --- | --- | --- | --- |
| Zero order | 0.800 | 0.837 | 0.960 |
| First order | 0.988 | 0.981 | 0.985 |
| Higuchi | 0.912 | 0.927 | 0.983 |
| Korsmeyer-Peppas | 0.970 | 0.966 | 0.973 |
| Hixson-Crowell | 0.944 | 0.964 | 0.962 |

Table 7 shows the $R^2$ values of linear plots of different kinetic models for platinum drugs' release from HoIG-Pt. According to the $R^2$ values the best linearity can be found in first order models ($R^2$=0.988, 0.981 and 0.985), indicating the release rate is concentration-dependent.

Neutron Activation of HoIG and HoIG-Pt.

Dry HoIG and HoIG-Pt were neutron activated in a 1 MW TRIGA Mark I nuclear reactor at the Texas A&M Nuclear Science Center. When HoIG was neutron activated in a thermal neutron flux of approximately $7 \times 10^{12}$ neutrons $cm^{-2}$ $s^{-1}$ for 0.45 h, the radioactivity directly afterwards was approximately 250 µCi $mg^{-1}$. By quantifying the 81 keV photons emitted, the $^{166}$HoIG prepared here has a $^{166}$Ho content of approximately 49% w/w, which corroborates our ICP-MS data.

Ho-incorporated mesoporous silica nanoparticles, $^{166}$Ho-MSNs (size 80-100 nm), with a radioactivity of 327 µCi $mg^{-1}$ after 2.2 h neutron activation in a thermal neutron flux of $5.5 \times 10^{12}$ neutron $cm^{-2}$ $s^{-1}$, and $^{166}$Ho-incorporated mesoporous silica MCM-41 nanoparticles, $^{166}$Ho-MCM-41 (size 400 nm), with a radioactivity of 150 µCi $mg^{-1}$ after 2 h neutron activation in the same thermal neutron flux, were previously prepared (Di Pasqua et al., 2013; Di Pasqua et al., 2012). Holmium acetylacetonate nanoparticles (78 nm) prepared for radioablation of solid malignancies resulted in 324 µCi $mg^{-1}$ after 1 h neutron activation in a thermal neutron flux of $5 \times 10^{12}$ neutron $cm^{-2}s^{-1}$ (Bult et al., 2010). Also, polylactic acid (PLA) microspheres with an average diameter of 37 µm and labeled with $^{166}$Ho for internal radionuclide therapy of liver metastases were 1351 µCi $mg^{-1}$ after 1 h exposure to a neutron flux of $5 \times 10^{13}$ neutrons $cm^{-2}$ $s^{-1}$ (Nijsen et al., 1999).

Cytotoxicity Studies of HoIG and HoIG-Pt.

Figure 33A:
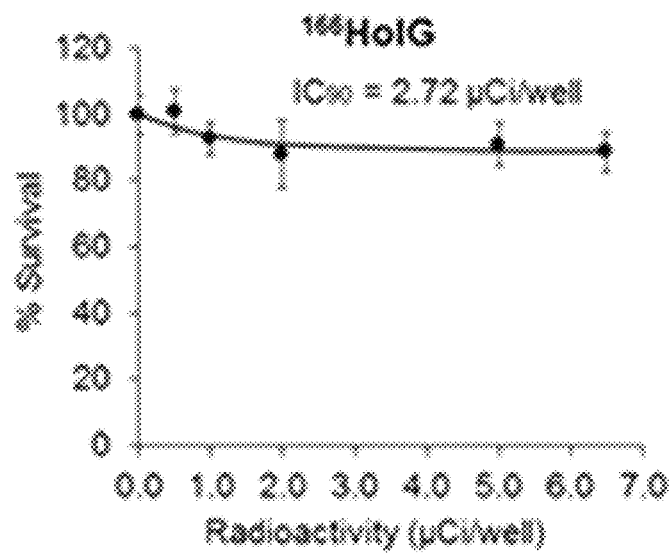
FIGS. 33A-33E. Percent cell survival versus radioactivity or Pt concentration in NSCLC A549 cells. The cells were exposed to free Pt drugs (cisplatin (FIG. 33B) or oxaliplatin (FIG. 33C)), blank $^{166}$HoIG (FIG. 33A) or Pt drug-loaded radioactive nanoparticles (FIGS. 33D-E) for 24 h. The ratio of [Pt] to radioactivity used in all the platinum-containing nanoparticles was ~80 µM Pt/µCi.
Figure 33B:
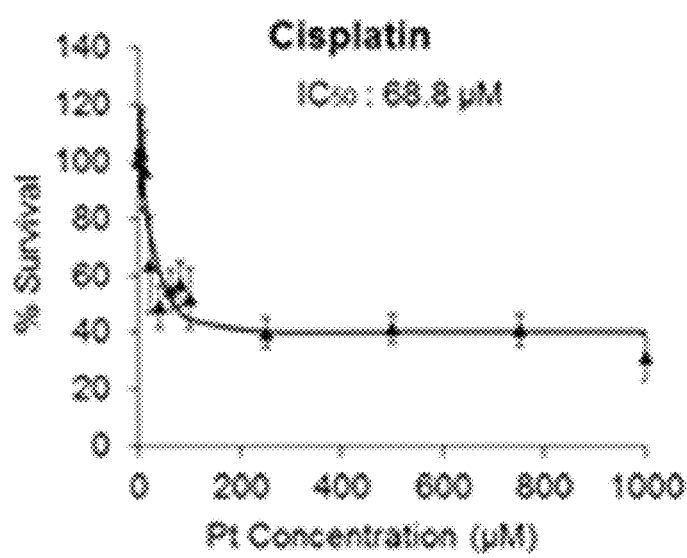
Figure 33C:
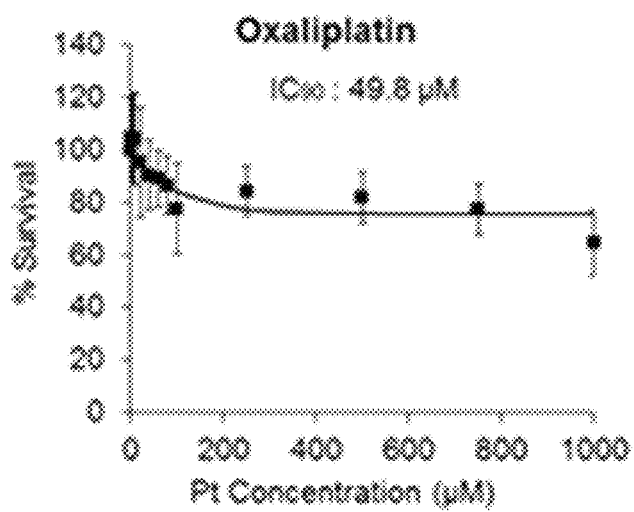
Figure 33D:
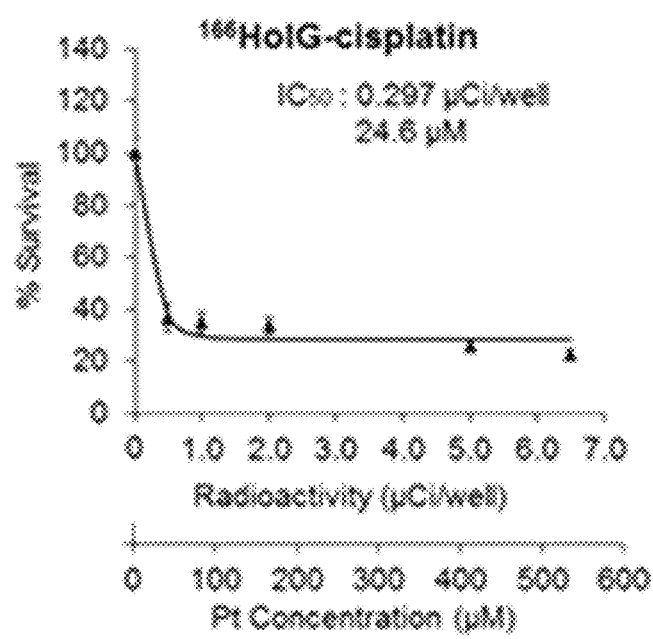
Figure 33E:
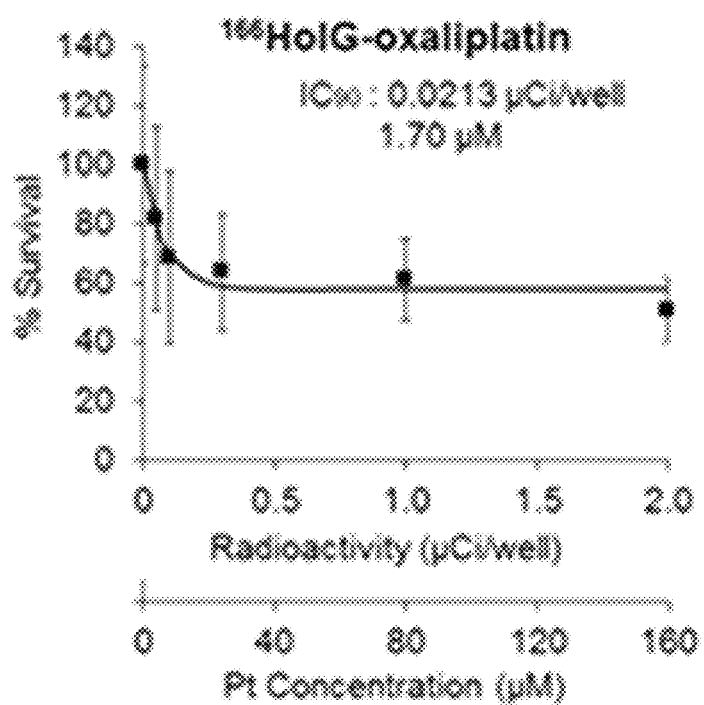
Figure 34:
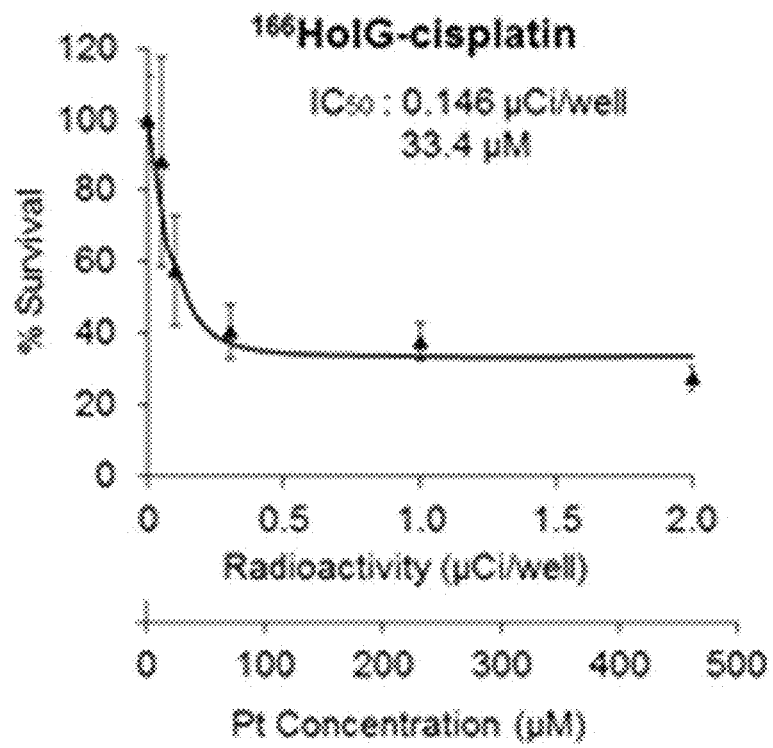
FIG. 34. Percent cell survival versus radioactivity or Pt concentration in NSCLC A549 cells with a higher Pt concentration to radioactivity ratio. The cells were exposed to $^{166}$HoIG-cisplatin for 24 h. The ratio of [Pt] to radioactivity used in the platinum-containing nanoparticles was ~230 µM/µCi.

Human NSCLC A549 cells were treated with blank $^{166}$HoIG, free-cisplatin, -carboplatin, or -oxaliplatin, $^{166}$HoIG-cisplatin, $^{166}$HoIG-carboplatin or $^{166}$HoIG-oxaliplatin (FIG. 33A-E) for 24 h at 37° C. As is shown in FIG. 33A, at the radioactivities used, the blank magnetic nanoparticle formulation, $^{166}$HoIG, was only slightly toxic toward NSCLC A549 cells. The studies involving the Pt drug-loaded nanoparticles, $^{166}$HoIG-cisplatin, $^{166}$HoIG-carboplatin and $^{166}$HoIG-oxaliplatin, were performed using approximately the same Pt to radiation ratio (~80 µM/µCi). $^{166}$HoIG-cisplatin and $^{166}$HoIG-oxaliplatin exhibited much higher levels of toxicity toward A549 cells (FIGS. 33D and E) than $^{166}$HoIG and free cisplatin and oxaliplatin (FIGS. 33B and C), respectively. Free carboplatin, however, did not act synergistically with radiation (data not shown). To further investigate its cytotoxicity in vitro, another $^{166}$HoIG-cisplatin study was performed, this time with a higher ratio of Pt to radiation (~230 µM/µCi, FIG. 34). This study confirmed that low amounts of radiation act synergistically with cisplatin.

Platinum-derived drugs have been used as radiosensitizers (Geldof et al., 1996). Preclinical studies have shown that the combination of the drug with radiation increases toxicity toward tumor cells, but the mechanism remains unclear (Rezaee et al., 2013). It was reported that the yield of DNA strand breaks increased during radiotherapy when cisplatin was present (Rezaee et al., 2013). A distinct advantage of the present system is that the Pt-based chemotherapeutic and $^{166}$Ho can be delivered together via a magnetic field and act synergistically.

Animal Studies.

Figure 35:
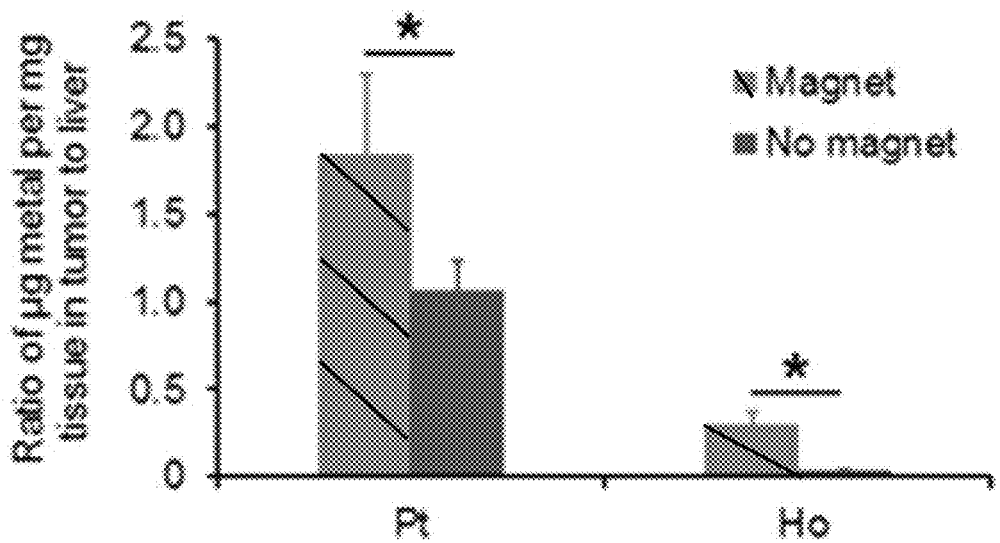
FIG. 35. Ratio of percent weight metal in tumor to liver after i.v. injection of HoIG-cisplatin.

Distribution of HoIG-cisplatin in tumors and livers was investigated using a subcutaneous NSCLC A549 xenograft athymic nude mouse model. Five million A549 cells were injected subcutaneously into each mouse; when tumor size reached approximately 50 $mm^3$, one group of mice were exposed to an external magnetic field and received HoIG-cisplatin injection via the tail vein, while the other group received the same injection without exposure to an external magnetic field. After the first group had been exposed to a magnetic field for 5 h, tumor and liver tissues of both groups were harvested. Using ICP-MS, Pt and Ho contents in tumor and liver samples were measured. As illustrated in FIG. 35, for Pt, the ratio of metal contents in tumor to liver was 1.84±0.46 with magnet and 1.06±0.17 without magnet; for Ho, the values were 0.29±0.08 with magnet and 0.03±0.01 without magnet. In both cases, the differences were significant ($p<0.05$). This indicates that when an external magnetic field is applied, HoIG-cisplatin localizes in tumors, more so than when no magnet is applied, which suggests that magnetic targeting was achieved using this system.

Figure 36:
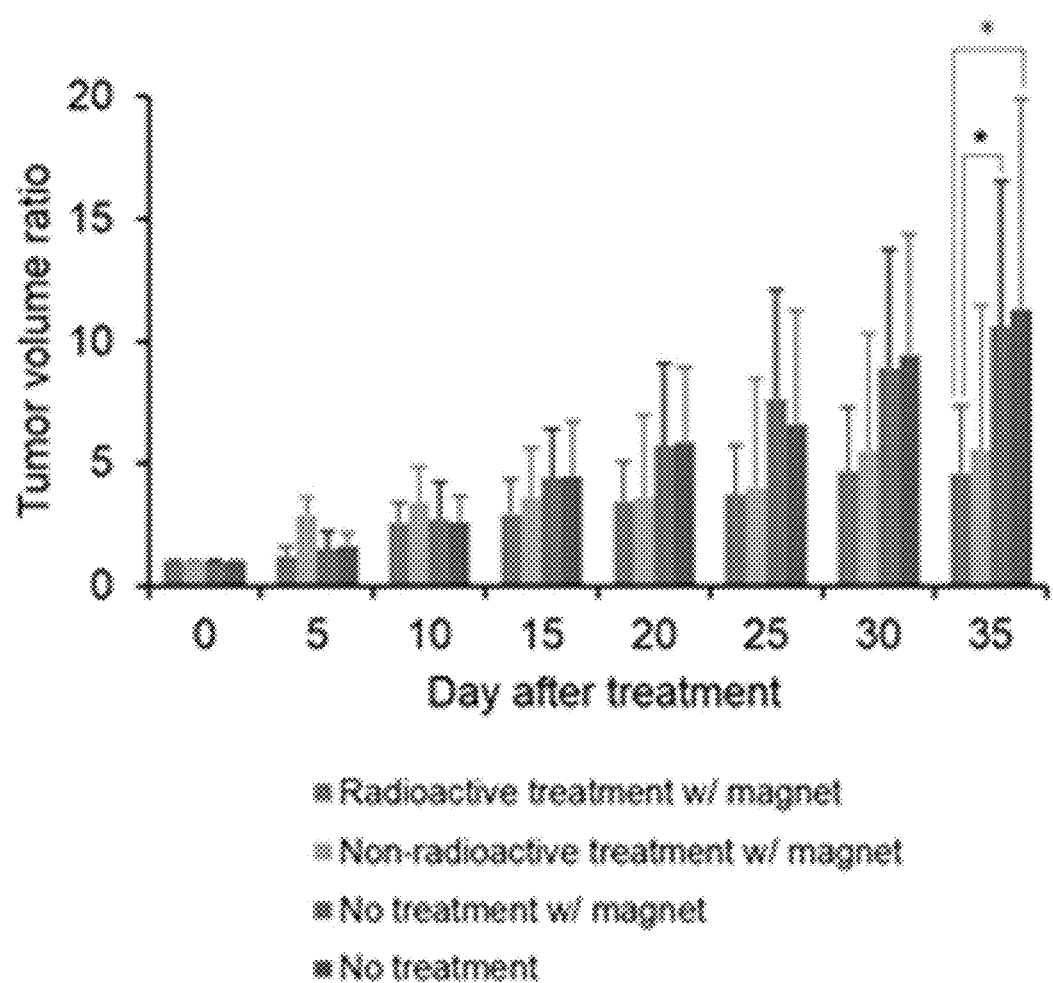
FIG. 36. Tumor volume ratio after i.v. injection of $^{166}$HoIG-cisplatin and HoIG-cisplatin with magnets.
Figure 37A:
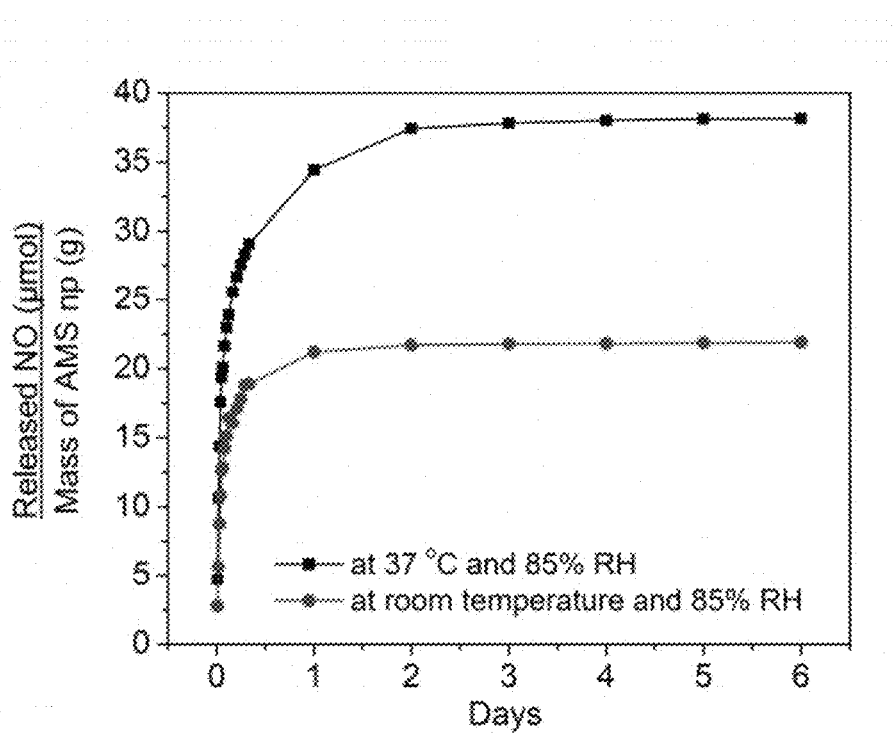
FIGS. 37A-37B. Nitric oxide (NO) release from (FIG. 37A) nanoparticles and (FIG. 37B) mats containing $^{165}$Ho. Temperature-controlled NO-releasing materials have been constructed.
Figure 37B:
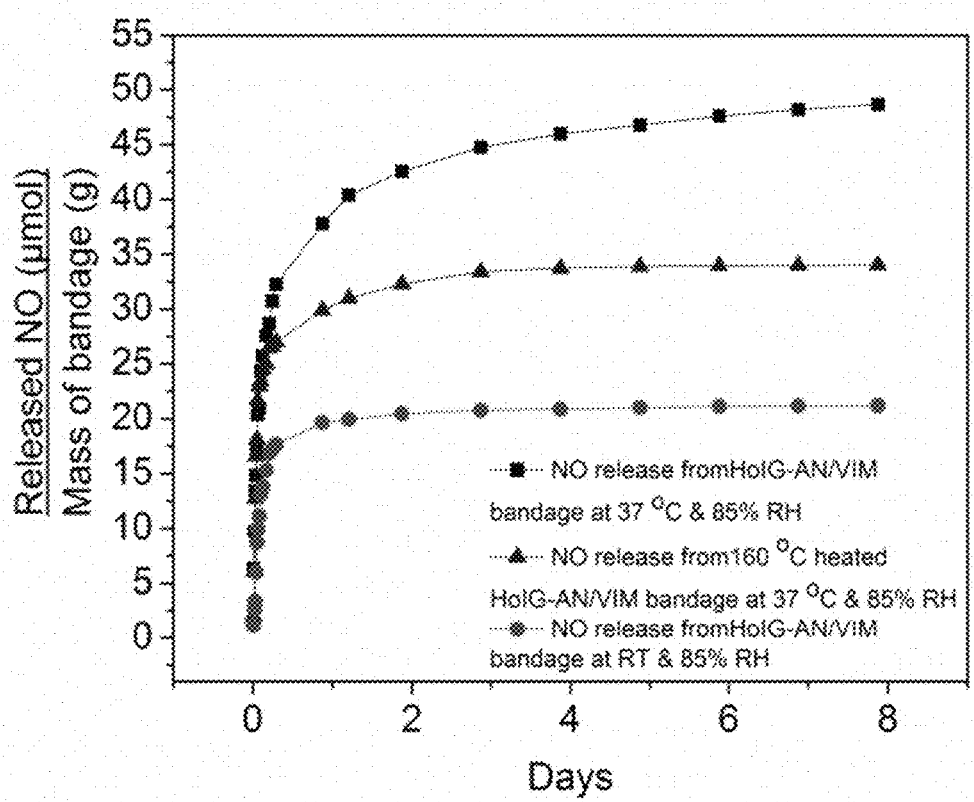

In the efficacy study, the same magnetic targeting system was used. Five million NSCLC A549 cells were injected subcutaneously into each mouse; when tumor volumes reached approximately 50-100 $mm^3$, Groups 1-3, which are blue, green and light red, respectively, in FIG. 36, were exposed to an external magnetic field and received radioactive $^{166}$HoIG-cisplatin, non-radioactive HoIG-cisplatin and no treatment, respectively. A control group, Group 4, which is grey in FIG. 36, was given no treatment and was not exposed to a magnet. Magnets applied in Groups 1-3 were removed after 5 h exposure and tumor growth monitored once every five days for 35 days after treatment. Tumor volumes were measured and tumor volume ratios calculated using tumor volume on the day of measurement divided by tumor volume on the day of treatment (Day 0). As is shown in FIG. 36, after 35 days, the tumor volume ratio for Group 3 and that for Group 4 were very similar, which indicates that the applied external magnetic field by itself has no impact on tumor growth.

Thirty-five days after radioactive $^{166}$HoIG-cisplatin injection, the tumor volume ratio of Group 1 was significantly lower than that of Group 3 and Group 4, with $p<0.05$ in both cases, demonstrating the inhibition of tumor growth by this chemoradiotherapeutic magnetic nanoparticle compared to no-treatment controls. Group 2, treated with HoIG cisplatin, was lower than no-treatment controls, but not significantly; thus, radiation (200 µCi per mouse) contributed to the tumor growth inhibition.

Example 7

Here we describe a new and improved strategy for the radiotherapeutic treatment of squamous cell carcinoma (SCC). $^{165}$Ho-containing nanoparticles and NO-releasing nanozeolites will be homogeneously incorporated into electrospun polymer nanofibrous mats; after being made radioactive via neutron activation, the bandage will conform to the cancer site and treat the covered area. The $\beta^-$ energy of $^{166}$Ho will be sufficient to damage DNA in cancer cells just beneath the outermost layer of the epidermis, and the bandage will store and release NO, a radiosensitizer that will allow for lower doses of radiation to be used. Because radiation can be both beneficial, in regards to treatment, and detrimental, in regards to healthy tissues, lower doses with the same efficacy as higher doses are preferable. Unlike a tumor lesion, the surrounding healthy skin has a stratum corneum, which will offer protection from low doses of radiation. This combination should help patients achieve optimized cosmetic and/or functional outcomes without the use of cumbersome equipment and specialized instrumentation and facilities.

The "radiotherapeutic bandage" described herein comprises a radiotherapeutic nuclide, e.g., $^{166}$Ho, as well as a nanozeolite that releases NO, a radiosensitizer that will allow for lower doses of radiation to be used in therapy. The bandage can be prepared via electrospinning, a simple approach that uses electrostatic forces to produce nanofibrous materials and allows for nanoparticles to be homogenously distributed throughout. The thickness of these materials can be varied by controlling parameters such as spinning duration, polymer concentration, applied voltage, temperature and humidity. The electrospinning method is attractive because of its low cost and suitability for mass production. Furthermore, after being incorporated, nanoparticles are not released during application. The bandage is also easily manipulatable to fit the specific size and location of the tumor lesion.

Methods:
1) Prepare stable electrospun polymer nanofibrous mats containing $^{166}$Ho-nanoparticles and NO-releasing nanozeolites. A hydroxide co-precipitation method will be used to prepare the $^{165}$Ho nanoparticles ($^{165}$HoIG). $^{165}$Ho nitrate will be stirred in ethylene glycol and 6 M sodium hydroxide used to precipitate $^{165}$Ho-nanoparticles; these nanoparticles will then be annealed at 900° C. for 3 h to obtain a crystalline product. The nanozeolites can be prepared as follows. Aluminum isopropoxide, trimethylammonium hydroxide, 1 M sodium hydroxide solution and water will be stirred at 40° C. until clear. Separately, 30% silica sol will be combined with water and stirred at 40° C. until clear. These will then be combined and placed in an oven for 24 h at 80° C., and the resulting nanozeolites washed, collected and dried. Both of these nanomaterials will be characterized with dynamic light scattering (DLS), X-ray diffraction (XRD) spectroscopy and transmission electron microscopy (TEM), and the $^{165}$Ho content of the nanoparticles determined using inductively coupled plasma-mass spectrometry (ICP-MS). The $^{165}$Ho nanoparticles and nanozeolites will be incorporated into a nanofibrous mat via electrospinning. Briefly, the nanomaterials will be dispersed in dimethylformamide (DMF) at room temperature, as will polyacrylonitrile (PAN), separately. The two solutions will then be mixed with continuous stirring until a homogeneous suspension is obtained, which will then be passed through a syringe with a spinneret needle using a syringe pump and a voltage of approximately 13 kV applied to the needle. The nanozeolites in the blend will be made to adsorb NO by induction of NO in a purged heated oven. Modulation of the rate and extent of NO release can be easily accomplished by modifying the nanozeolites and the fiber porosity of the mat. Neutron activation in a thermal neutron flux of approximately $3.5\times 10^{12}$ n/cm$^2$·s in a 1 MW nuclear reactor will produce $^{166}$Ho nanoparticles in the mat. After production of this "radiotherapeutic bandage", its radioactivity will be determined by quantifying the photons emitted using a PerkinElmer γ spectrometer and release of NO assessed with Griess reagent and UV-visible spectroscopy. Its overall stability after various neutron-activation times will be determined by visual inspection and scanning electron microscopy (SEM).

Polymer blends containing $^{166}$Ho nanoparticles and NO-releasing nanozeolites will be evaluated in SCC cell lines, i.e., SRB-1, SRB-12, Colo-16 and UT-SCC-14, and an optimized ratio of $^{166}$Ho radioactivity to NO concentration in the mat will be determined for use in the final blend of the "radiotherapeutic bandage". Cells will be maintained in DMEM growth medium with 10% fetal bovine serum and 1% penicillin/streptomycin, and grown in a 37° C., 5% CO$_2$ incubator. Mats with various ratios of $^{166}$Ho radioactivity to NO concentration will be placed in culture medium over monolayers of SCC cells for 24 h and apoptosis determined using an Annexin V FITC assay. Percent cell apoptosis will be used as the measure of a therapy's efficacy. No nanoparticles are expected to be released from the mat when immersed in solution and controls, including non-radioactive bandages with no NO, will be tested to rule out any effect of the polymers; thus, only the effects of radiation and NO from the intact bandage will be studied. Prior to the aforementioned cell studies, the release profile of NO from the mats will be determined using the Griess reagent and UV-visible spectroscopy, so the concentrations of NO that cells are exposed to over the 24 h period can be determined. Animal studies will also be performed following a protocol approved by the University of North Texas Health Science Center Institutional Animal Care and Use Committee (IACUC) in accordance with the NIH Guidelines. Based on its sensitivity to the $^{166}$Ho/NO combination therapy, a human SCC cell line from Aim 2 will be selected; approximately 4 week old female athymic nude mice will be used and five million cells injected subcutaneously into the left hind leg of each. When tumors are approximately 50 mm$^3$ in diameter, the optimized "radiotherapeutic bandage" and controls will be applied with Nexcare Steri-Strip surgical tape for 24 h.

The following groups will be studied: 1) No treatment, 2) Non-radioactive bandage with no NO, 3) NO-releasing non-radioactive bandage, 4) $^{166}$Ho-containing bandage with no NO, and 5) NO-releasing $^{166}$Ho-containing bandage, i.e., "radiotherapeutic bandage". NO is capable of diffusing through the skin and the β⁻ energy of $^{166}$Ho is sufficient to penetrate the xenograft; thus, this animal model is appropriate for the study of our "radiotherapeutic bandage". Before and then three times a week after treatment, tumor sizes will be measured using a caliper; this will be done for 30 days post-therapy, which is sufficient to observe the inhibition of tumor growth after a one-time treatment, and inhibition of tumor growth will be compared among all five groups to determine efficacy. Mice will then be sacrificed for pathologic evaluations to determine if any damage to muscles or internal organs resulted from therapy, and to compare damage, if any, between groups.

An electrospun polymer nanofibrous mat containing $^{165}$Ho nanoparticles has been made and remains completely intact after neutron activation. Furthermore, $^{166}$Ho is homogenously distributed throughout the mat, which is critical for efficient radiotherapy. We have also prepared a prototype "radiotherapeutic bandage" that contains $^{165}$Ho and releases NO.

Example 8

Materials.

Holmium (III) nitrate hexahydrate, sodium hydroxide, ethylene glycol, and polyacrylonitrile (Molecular weight: 150,000 mol/g) were purchased from Aldrich Chemical Co. Iron (III) nitrate hexahydrate was purchased from Acros Organics. Dimethylformamide (DMF) was purchased from Fisher Scientific. All reagents were used as received.

Synthesis of HoIG Nanoparticles.

$^{165}$HoIG nanoparticles were synthesized by modifying a reported procedure (Munaweera et al., 2014). Stoichiometric mixtures (5:3) of 1 M iron (III) nitrate (5 mL) and 1 M holmium (III) nitrate (3 mL) were mixed with ethylene glycol (21 mL) at room temperature with stirring. Then 6 M NaOH (10 mL) was added dropwise to form the $^{165}$HoIG nanoparticle precipitate. The product was centrifuged and washed with de-ionized water, then dried at 100° C. overnight. The $^{165}$HoIG was annealed in air at 900° C. for 3 h.

Electrospinning of Polyacrylonitrile Polymer Solutions with $^{165}$HoIG Nanoparticles ($^{165}$HoIG/PAN).

Polyacrylonitrile (PAN) (1.0 g) was dispersed in dimethylformamide (DMF) (5 mL), with gentle heating and stirring. $^{165}$HoIG nanoparticles were dispersed in DMF (5 mL) and mixed with the PAN solution at room temperature to prepare 33 and 50% w/w dispersions (Table 8). The PAN solutions containing $^{165}$HoIG nanoparticles were drawn into a 12 mL syringe equipped with a 20 gauge needle and electrospun on an aluminum foil substrate wrapped around a rotating drum. The electrospinning conditions are listed in Table 8.

TABLE 8

| Sample | PAN (g) | $^{165}$HoIG nano-particles (g) | Volume of DMF (mL) | Rate (mL/h) | Voltage (kV) | Electrode separation distance (cm) |
|---|---|---|---|---|---|---|
| 33% (w/w) $^{165}$HoIG | 1.0 | 0.5 | 10 | 0.05 | 14 | 6 |

TABLE 8-continued

| Sample | PAN (g) | $^{165}$HoIG nano-particles (g) | Volume of DMF (mL) | Rate (mL/h) | Voltage (kV) | Electrode separation distance (cm) |
|---|---|---|---|---|---|---|
| 50% (w/w) $^{165}$HoIG | 1.0 | 1.0 | 10 | 0.05 | 14 | 6 |

Neutron Activation of $^{165}$HoIG and $^{165}$HoIG/PAN.

$^{165}$HoIG nanoparticles (5 mg) and approximately 0.5×0.5 cm² (6 mg) $^{165}$Ho-containing polymer nanofibrous mats cut from both the 33% (w/w) and 50% (w/w) $^{165}$HoIG/PAN were neutron-activated in a 1 MW TRIGA Mark I nuclear reactor at the Texas A&M Nuclear Science Center in a thermal neutron flux of approximately $3.5 \times 10^{12}$ neutrons/cm²·s for 0.5, 1.0, 2.0 or 4.0 h. Radioactivities were determined by quantifying the photons emitted using a gamma spectrometer. The radioactivities directly after neutron activation are reported.

Characterization.

X-ray diffraction patterns were collected on a Rigaku Ultima IV x-ray diffractometer using Cu Kα radiation. The morphology of the synthesized $^{165}$HoIG nanoparticles and electrospun fibers were analyzed using scanning electron microscopy (SEM) and transmission electron microscopy (TEM). SEM analyses of Au/Pd coated samples were carried out using a Zeiss-LEO model 1530 SEM. TEM analysis was performed on JEOL 2100 analytical TEM with an accelerating voltage of 200 kV. Fourier Transform Infrared Spectroscopy (FTIR) analyses of $^{165}$HoIG nanoparticles and bandages were carried out using a Nicolet 380 spectrometer equipped with an Attenuated Total Reflectance (ATR) attachment. TGA analysis was performed using TA Instruments SDT Q600. Inductively coupled plasma-mass spectrometry (ICP-MS) was performed to determine the $^{165}$Ho content in $^{165}$HoIG using NexION 300D from PerkinElmer. Gamma radiation of neutron-activated samples was measured using a Canberra Industries HPGe GC3518.

$^{165}$HoIG Nanoparticles.

FIGS. 27A and B show the PXRD patterns for the as-synthesized $^{165}$HoIG nanoparticles. The phase matches well with $Fe_5Ho_3O_{12}$ (JCPDS 00-023-0282). The crystallite sizes were calculated from the PXRD line broadening of the 420 reflection using the Scherrer equation, $D_{hkl} = k\lambda/B \cos\theta$, where $D_{hkl}$ is the particle size in nm, k is a constant (shape factor) with a value of 0.9, B is the width of half maximum, and λ is the wavelength of the x-rays. The $D_{hkl}$ value of $^{165}$HoIG is about 52 nm.

Figure 28A:
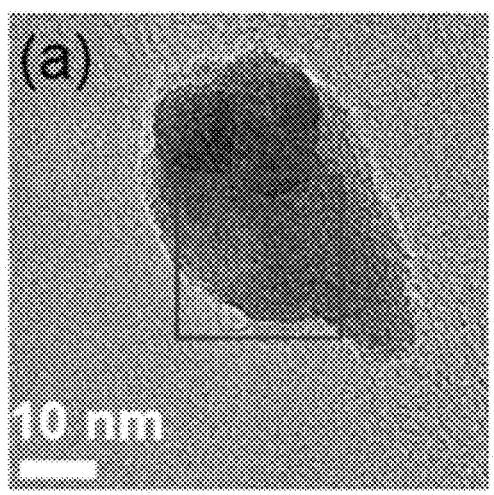
FIGS. 28A-28B. TEM images of a synthesized HoIG nanoparticle. The TEM image of synthesized HoIG (FIG. 28A) exhibits a rounded irregular shape. The average size of the nanoparticles is 40.7±16.4 nm in length and 26.9±8.0 nm in width. The interplanar distance of HoIG in FIG. 28B is 0.28 nm, which corresponds to the (420) plane d=0.27670 nm in FIGS. 27A and 27B FIG. 29. M-H hysteresis loop of the synthesized HoIG.
Figure 28B:
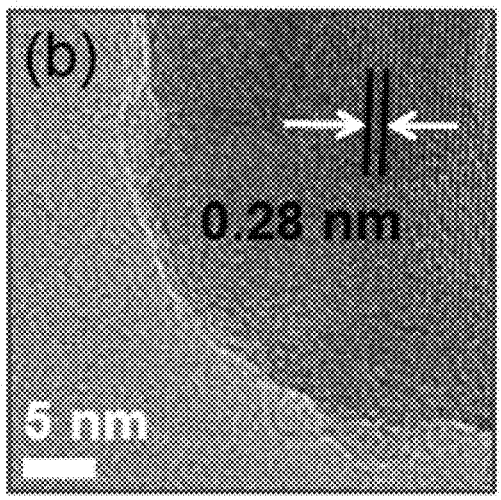
Figure 29:
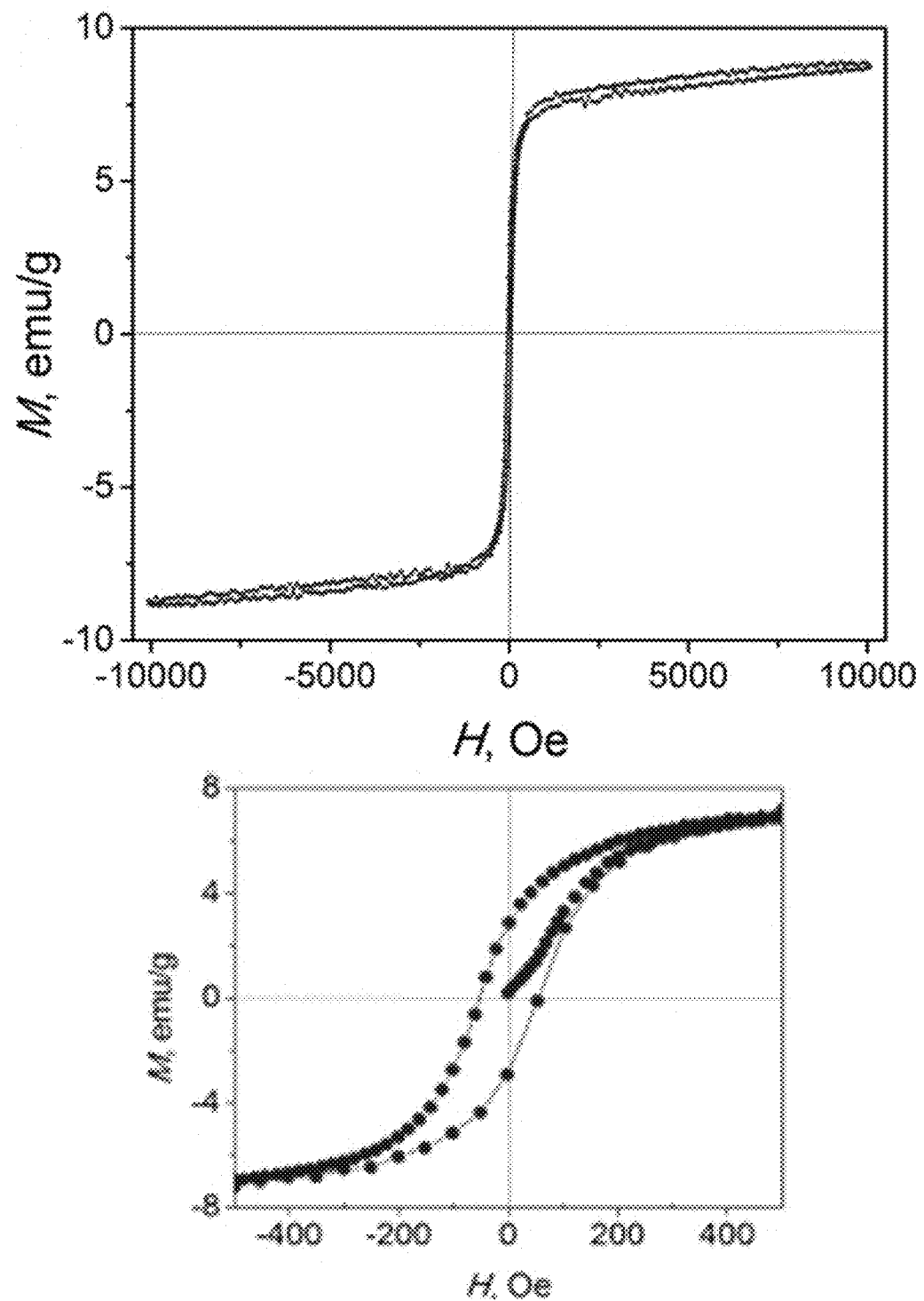

TEM images of the as-synthesized $^{165}$HoIG nanoparticles are shown in FIGS. 28A and B. The nanoparticles generally exhibited a rounded irregular-shaped morphology. The length of $^{165}$HoIG is 55 nm and the width is 28 nm. The interplanar distance of $^{165}$HoIG is 0.28 nm (FIG. 28 (B) which corresponds to the (420) plane is d=0.278 nm in FIG. 27. Using ICP-MS, the $^{165}$HoIG was determined to contain 55.6% (w/w) holmium.

Electrospinning of PAN-Containing HoIG Nanoparticles.

SEM images of the electrospun fiber mats with different $^{165}$HoIG nanoparticle loadings are shown in FIGS. 23A and B. As shown in the histogram 90% of fibers are below 300 nm. The average diameter of nanofibers is 174±56 nm and 208±54 nm when the $^{165}$HoIG loadings were 33% and 50% (w/w). The increase in the fiber diameter with increasing $^{165}$HoIG content may reflect the size of the garnet nanoparticles as well as agglomeration (Munaweera et al., 2014; Hassan et al., 2014).

Radiotherapeutic bandages (before and after neutron activation) were soaked in simulated body fluid (SBF) and DI water for 4 and 8 h and samples from SBF and water were analyzed using TEM to check whether there is any loss of the embedded nanoparticles from the PAN fibers. There were no free nanoparticles detected in the samples. These results confirm that radioactive particles do not leach out from the radiotherapeutic bandage.

Neutron Activation of $^{165}$HoIG Nanoparticles and $^{165}$HoIG/PAN Bandages.

$^{165}$HoIG and rectangles of $^{165}$HoIG/PAN were neutron activated for 0.5, 1, 2 and 4 h. Radioactivities of 56.8, 330.7, 833.8 and 1633.6 µCi/mg were obtained for $^{166}$HoIG nanoparticles after approximately 0.5, 1, 2 and 4 h neutron activation, respectively. From these data, we can calculate that $^{166}$HoIG nanoparticles contain 57.8±26.2% (w/w) $^{166}$Ho, which corroborates the ICP-MS data.

It is critical for the $^{166}$HoIG/PAN bandage to emit radiation uniformly during therapy; thus, four rectangular pieces were cut from a 33% $^{165}$HoIG/PAN in four different locations and neutron-activated for 0.5 h. The same was done for the 50% HoIG/PAN bandage. After neutron activation, the radioactivities were measured and $^{166}$Ho content determined; 17.1±0.7% and 22.7±1.9% of $^{166}$Ho was contained in electrospun fibers with 33% (w/w) HoIG and 50% (w/w) HoIG, respectively. This is consistent with a uniform dispersion of $^{166}$HoIG throughout the bandage after electrospinning, as well as efficient loading of HoIG into the bandage.

Radioactivities of 48.1, 101.1, 479.2 and 650.3 µCi/mg were produced for 33% HoIG/PAN, and 63.7, 163.3, 300.0 and 854.7 µCi/mg for 50% HoIG/PAN, after 0.5, 1, 2 and 4 h neutron activation, respectively. Thus, radioactivities of $6.420 \times 10^2$, $1.675 \times 10^3$, $1.917 \times 10^4$ and $2.016 \times 10^4$ µCi/cm$^2$ were produced for 33% HoIG/PAN bandages, and $1.411 \times 10^3$, $6.532 \times 10^3$, $4.501 \times 10^3$ and $2.607 \times 10^4$ µCi/cm$^2$ were produced for 50% HoIG/PAN bandages.

Radioactivity can be calculated using the following formula:

$$A = nfs(1-e^{-\lambda T})e^{-\lambda t},$$

where A is radioactivity produced (Bq/mg, which is $2.7 \times 10^{-11}$ Ci/mg), n is number of atoms per mg, f is neutron flux density (n/cm$^2$.\$), s is thermal neutron capture cross section (cm$^2$), $\lambda$ is decay constant ($0.693/t_{1/2}$), T is irradiation time and t is decay time. Here, nfs is a constant, and immediately after neutron activation, t is 0. Thus, A should be proportional to $1-e^{-\lambda T}$. We here plot radioactivity (A) in µCi/mg against $1-e^{-\lambda T}$ (FIG. 16F). Least-squares linear fits give R$^2$ values of 0.93, 0.96 and 0.98 for the 33 and 50% HoIG/PAN and HoIG data sets, respectively.

This example demonstrates that $^{166}$Ho-containing bandages with different amounts of radioactivity can be prepared by varying the neutron-activation time and the amount of neutron-activatable nuclide incorporated. Preparing and handling large amounts of hazardous, highly radioactive materials with short half-lives can be cumbersome and, thus, is here avoided using neutron-activatable $^{165}$Ho. The β$^-$ energy of $^{166}$Ho should be sufficient to damage DNA in cancer cells just beneath the outermost layer of the epidermis, and it is expected that the stratum corneum will protect any normal skin surrounding the tumor lesion from radiation damage. Thus, this approach could help patients achieve optimized cosmetic and/or functional outcomes without the use of specialized instrumentation or facilities. It is envisioned that a lead wrap could be placed around the bandage during treatment while sitting in a physician's office.

REFERENCES

Munaweera, I.; Aliev, A.; Balkus, K. J. "Electrospun Cellulose Acetate-Garnet Nanocomposite Magnetic Fibers for Bioseparations" ACS Appl. Mater. Interfaces 2014, 6, 244.

Rajendran, M.; Deka, S.; Joy, P. A.; Bhattacharya, A. K. J. Magn. Magn. Mater. 2006, 301, 212.

Lataifeh, M. S. J. Phys. Soc. Jpn. 2000, 69, 2280.

Nguyet, D. T. T.; Duong, N. P.; Satoh, T.; Anh, L. N.; Hien, T. D. J. Magn. Magn. Mater. 2013, 332, 180.

Yan, X.; Gemeinhart, R. A. J. Controlled Release 2005, 106, 198.

Wysokiński, R.; Kuduk-Jaworska, J.; Michalska, D. J. Mol. Struct.: THEOCHEM 2006, 758, 169.

Tyagi, P.; Gahlot, P.; Kakkar, R. Polyhedron 2008, 27, 3567.

Pugh, R. J.; Bergstrom, L. "Surface and Colloid Chemistry" in Advanced Ceramic Processing, Surfactant Science Series; Marcel Dekker: New York, 1994.

Yan, X.; Gemeinhart, R. A. J. Controlled Release 2005a, 106, 198.

Cheng, X.; Kuhn, L. Int. J. Nanomed. 2007, 2, 667.

Sun, H.-W.; Zhang, L.-Y; Zhu, X.-J.; Wang, X.-F. J. Biomater. Sci., Polym. Ed. 2009, 20, 1675.

Munaweera, I.; Koneru, B.; Shi, Y.; Di Pasqua, A. J.; Balkus, Jr. K. J. APL Mater. 2014a, 2, 113315.

Dash, S.; Murthy, P. N.; Nath, L.; Chowdhury, P. Acta Pol. Pharm. Drug Res. 2010, 67, 217.

Di Pasqua, A. J.; Miller, M. L.; Lu, X.; Peng, L.; Jay, M. Inorg. Chim. Acta 2012, 393, 334.

Bult, W.; Varkevisser, R.; Soulimani, F.; Seevinck, P. R.; De Leeuw, H.; Bakker, C. J. G.; Luijten, P. R.; Van Het Schip, A. D.; Hennink, W. E.; Nijsen, J. F. W. Pharm. Res. 2010, 27, 2205.

Nijsen, J. F. W.; Zonnenberg, B. A.; Woittiez, J. R. W.; Rook, D. W.; Swildens-Van Woudenberg, I. A.; Van Rijk, P. P.; Van het Schip, A. D. Eur. J. Nucl. Med. 1999, 26, 699.

Geldof, A. A.; Slotman, B. J. Cancer Lett. 1996, 101, 233.

Rezaee, M.; Sanche, L.; Hunting, D. J. Radiat. Res. 2013, 179, 323.

Hassan, M. I.; Sultana, N.; Hamdan, S. "Bioactivity Assessment of Poly(ϵ-caprolactone)/Hydroxyapatite Electrospun Fibers for Bone Tissue Engineering Application" J. Nanomater. 2014, 6.

We claim:

1. A film, electrospun fabric or bandage comprising a polymer-embedded iron garnet nanoparticle or iron garnet particle comprising one, or any combination of, activatable nuclide selected from lanthanum-139, praseodymium-141, samarium-152, dysprosium-164, holmium-165, rhenium-185 and/or rhenium-187 and, optionally, a radiosensitizer, said film, electrospun fabric or bandage emitting relatively uniform radiation across the surface area of said film, electrospun fabric or bandage after activation.

2. The film, electrospun fabric or bandage according to claim 1, wherein said film, electrospun fabric or bandage has relatively uniform distribution of said nanoparticle or particle within said film, electrospun fabric or bandage.

3. The film, electrospun fabric or bandage according to claim 1, wherein said electrospun fabric comprises polymers selected from acrylonitriles, vinylimidazole, butyl acrylate, isoprene, butadiene, caprolactam and combinations thereof.

4. The film, electrospun fabric or bandage according to claim 1, said film, electrospun fabric or bandage further comprising a wound healing agent or radiosensitizer.

5. The film, electrospun fabric or bandage according to claim 4, wherein said wound healing agent is selected from antibiotics, anti-microbial agents, dialkylcarbamoylchloride, povidone-iodine, silver, growth factors, nitrous oxide and combinations thereof and the radiosensitizer is platinum, ruthenium, palladium, iron, cobalt, nickel, copper, rhodium, gold, silver, nitrous oxide, and/or boron.

6. The film, electrospun fabric or bandage according to claim 5, wherein said wound healing agent is selected from epidermal growth factor (EGF), platelet derived growth factor (PDGF), fibroblast growth factor (FGF), transforming growth factor (TGF), insulin-like growth factor (IGF), human growth hormone, granulocyte-macrophage colony-stimulating factor (GM-CSF) and combinations thereof.

7. A method of treating a skin disease or condition comprising the application of an activated film, electrospun fabric or bandage according to claim 1 to the skin of a subject having a skin disease or condition selected from psoriasis, skin cancer, melanoma, Merkel cell carcinoma, or squamous cell carcinoma.

8. The method according to claim 7, wherein said film, electrospun fabric or bandage has relatively uniform distribution of said nanoparticle or particle within said film, electrospun fabric or bandage.

9. The method according to claim 7, wherein said electrospun fabric comprises polymers selected from acrylonitriles, vinylimidazole, butyl acrylate, isoprene, butadiene, caprolactam and combinations thereof.

10. The method according to claim 7, wherein the film, electrospun fabric or bandage further comprises a wound healing agent or a radiosensitizer.

11. The method according to claim 10, wherein said wound healing agent is selected from antibiotics, anti-microbial agents, dialkylcarbamoylchloride, povidone-iodine, silver, growth factors, nitrous oxide and combinations thereof and the radiosensitizer is platinum, ruthenium, palladium, iron, cobalt, nickel, copper, rhodium, gold, silver, nitrous oxide, and/or boron.

12. The method according to claim 10, wherein said wound healing agent is selected from epidermal growth factor (EGF), platelet derived growth factor (PDGF), fibroblast growth factor (FGF), transforming growth factor, insulin-like growth factor, human growth hormone, granulocyte-macrophage colony-stimulating factor (GM-CSF) and combinations thereof.

* * * * *

UNITED STATES PATENT AND TRADEMARK OFFICE
CERTIFICATE OF CORRECTION

PATENT NO. : 9,808,543 B2
APPLICATION NO. : 14/600738
DATED : November 7, 2017
INVENTOR(S) : Anthony J. Di Pasqua et al.

It is certified that error appears in the above-identified patent and that said Letters Patent is hereby corrected as shown below:

In the Specification

Column 21,
Line 21, "$D_{hkl} =$/B cos θ" should read --$D_{hkl} = k\lambda$ /B cosθ--.

Signed and Sealed this
Twenty-fifth Day of September, 2018

Andrei Iancu
*Director of the United States Patent and Trademark Office*